United States Patent
Badawi et al.

(10) Patent No.: US 12,310,891 B2
(45) Date of Patent: May 27, 2025

(54) DEVICES AND METHODS FOR INTRAOCULAR TISSUE MANIPULATION

(71) Applicant: Sight Sciences, Inc., Menlo Park, CA (US)

(72) Inventors: David Y. Badawi, Glenview, IL (US); Paul Badawi, Atherton, CA (US); Daniel O'Keeffe, San Francisco, CA (US)

(73) Assignee: SIGHT SCIENCES, INC., Menlo Park, CA (US)

( * ) Notice: Subject to any disclaimer, the term of this patent is extended or adjusted under 35 U.S.C. 154(b) by 0 days.

(21) Appl. No.: 18/535,984

(22) Filed: Dec. 11, 2023

(65) Prior Publication Data
US 2024/0358546 A1 Oct. 31, 2024

Related U.S. Application Data

(63) Continuation of application No. 18/122,109, filed on Mar. 15, 2023, now Pat. No. 11,877,954.
(Continued)

(51) Int. Cl.
*A61F 9/007* (2006.01)
*A61B 17/32* (2006.01)

(52) U.S. Cl.
CPC ...... *A61F 9/00772* (2013.01); *A61F 9/00781* (2013.01); *A61B 2017/320044* (2013.01)

(58) Field of Classification Search
CPC .. A61F 9/007; A61F 9/00736; A61F 9/00772; A61F 9/00781; A61B 2017/320044
See application file for complete search history.

(56) References Cited

U.S. PATENT DOCUMENTS

| 2,130,949 A | 9/1938 | Wharton |
| 3,776,238 A | 12/1973 | Peyman et al. |

(Continued)

FOREIGN PATENT DOCUMENTS

| WO | WO-93/06800 A1 | 4/1993 |
| WO | WO-01/78631 A2 | 10/2001 |

(Continued)

OTHER PUBLICATIONS

First Commercial Sale of SION™ on Aug. 8, 2022 (Document Unavailable).
(Continued)

*Primary Examiner* — Kathleen S Holwerda
(74) *Attorney, Agent, or Firm* — Cooley LLP

(57) ABSTRACT

Provided herein are methods and devices for grasping and/or tearing trabecular meshwork of an eye of a subject. The devices may include a shaft and a tissue grabber coupled to the shaft. The tissue grabber may include an elongate lower foot configured to be inserted into Schlemm's canal, and a groove configured to grasp a portion of the trabecular meshwork. The methods may include: advancing a tissue grabber to Schlemm's canal of the eye, wherein the tissue gripper comprises a lower foot and a tissue grabbing region; advancing a tip of the lower foot through the trabecular meshwork and into Schlemm's canal; and advancing the lower foot within and relative to Schlemm's canal, wherein as the lower foot is advanced, a portion of the trabecular enters the tissue gripping region, is torn from surrounding tissue, and is collected within the tissue gripping region.

44 Claims, 37 Drawing Sheets

Related U.S. Application Data

(60) Provisional application No. 63/392,971, filed on Jul. 28, 2022, provisional application No. 63/320,643, filed on Mar. 16, 2022.

(56) References Cited

U.S. PATENT DOCUMENTS

| | | |
|---|---|---|
| 3,882,872 A | 5/1975 | Douvas et al. |
| 4,011,869 A | 3/1977 | Seiler |
| 4,111,207 A | 9/1978 | Seiler |
| 4,373,530 A | 2/1983 | Kilejian |
| 4,428,748 A | 1/1984 | Peyman et al. |
| 4,501,274 A | 2/1985 | Skjaerpe |
| 4,559,942 A | 12/1985 | Eisenberg |
| 4,577,629 A | 3/1986 | Martinez |
| 4,649,919 A | 3/1987 | Thimsen et al. |
| 4,682,597 A | 7/1987 | Myers |
| 4,900,300 A | 2/1990 | Lee |
| 5,042,008 A | 8/1991 | Iwasa et al. |
| 5,163,433 A | 11/1992 | Kagawa et al. |
| 5,217,476 A | 6/1993 | Wishinsky |
| 5,222,959 A | 6/1993 | Anis |
| 5,224,950 A | 7/1993 | Prywes |
| 5,258,002 A | 11/1993 | Jeffers et al. |
| 5,342,370 A | 8/1994 | Simon et al. |
| 5,364,409 A | 11/1994 | Kuwabara et al. |
| 5,431,671 A | 7/1995 | Nallakrishnan |
| 5,478,338 A | 12/1995 | Reynard |
| 5,487,747 A | 1/1996 | Stagmann et al. |
| 5,558,637 A | 9/1996 | Allonen et al. |
| 5,569,283 A | 10/1996 | Green et al. |
| 5,620,453 A | 4/1997 | Nallakrishnan |
| 5,674,233 A | 10/1997 | Dybbs |
| 5,713,915 A | 2/1998 | Van Heugten et al. |
| 5,718,708 A | 2/1998 | Webb |
| 5,817,115 A | 10/1998 | Nigam |
| 5,865,831 A | 2/1999 | Cozean et al. |
| 6,013,049 A | 1/2000 | Rockley et al. |
| 6,139,559 A | 10/2000 | Nordan et al. |
| 6,213,997 B1 | 4/2001 | Hood et al. |
| 6,241,721 B1 | 6/2001 | Cozean et al. |
| 6,251,103 B1 | 6/2001 | Berlin |
| 6,264,668 B1 | 7/2001 | Prywes |
| 6,388,043 B1 | 5/2002 | Langer et al. |
| 6,428,501 B1 | 8/2002 | Reynard |
| 6,497,712 B1 | 12/2002 | Feaster |
| 6,503,262 B1 | 1/2003 | Edens |
| 6,720,402 B2 | 4/2004 | Langer et al. |
| 6,759,481 B2 | 7/2004 | Tong |
| 6,979,328 B2 | 12/2005 | Baerveldt et al. |
| 7,374,566 B1 | 5/2008 | Schossau |
| 7,604,663 B1 | 10/2009 | Reimink et al. |
| 7,632,303 B1 | 12/2009 | Stalker et al. |
| 7,648,591 B2 | 1/2010 | Furst et al. |
| 7,785,321 B2 | 8/2010 | Baerveldt et al. |
| 7,883,519 B2 | 2/2011 | Oren et al. |
| 7,909,789 B2 | 3/2011 | Badawi et al. |
| 7,935,131 B2 | 5/2011 | Anthamatten et al. |
| 7,955,387 B2 | 6/2011 | Richter |
| 7,959,641 B2 | 6/2011 | Sorensen et al. |
| 8,038,923 B2 | 10/2011 | Berger et al. |
| 8,287,482 B2 | 10/2012 | Badawi et al. |
| 8,439,972 B2 | 5/2013 | Badawi et al. |
| 8,512,321 B2 | 8/2013 | Baerveldt et al. |
| 8,529,622 B2 | 9/2013 | Badawi et al. |
| 8,876,898 B2 | 11/2014 | Badawi et al. |
| 8,894,603 B2 | 11/2014 | Badawi et al. |
| 9,095,412 B2 | 8/2015 | Badawi et al. |
| 9,107,729 B2 | 8/2015 | Sorensen et al. |
| 9,216,109 B2 | 12/2015 | Badawi et al. |
| 9,226,850 B2 | 1/2016 | Baerveldt et al. |
| 9,358,155 B2 | 6/2016 | Sorensen et al. |
| 9,370,443 B2 | 6/2016 | Badawi et al. |
| 9,486,361 B2 | 11/2016 | Badawi et al. |
| 9,757,279 B2 | 9/2017 | Kahook |
| 9,820,885 B2 | 11/2017 | Sorensen et al. |
| 9,855,167 B2 | 1/2018 | Badawi et al. |
| 9,872,799 B2 | 1/2018 | Kahook |
| 9,895,258 B2 | 2/2018 | Badawi et al. |
| 9,999,544 B2 | 6/2018 | Baerveldt et al. |
| 10,085,885 B2 | 10/2018 | Baerveldt et al. |
| 10,123,905 B2 | 11/2018 | Mittelstein et al. |
| 10,179,066 B2 | 1/2019 | Badawi et al. |
| 10,213,342 B2 | 2/2019 | Kahook et al. |
| 10,299,958 B2 | 5/2019 | Badawi et al. |
| 10,314,742 B2 | 6/2019 | Badawi et al. |
| 10,327,947 B2 | 6/2019 | Kahook |
| 10,398,597 B2 | 9/2019 | Badawi et al. |
| 10,406,030 B2 | 9/2019 | Badawi et al. |
| 10,653,558 B2 | 5/2020 | Kahook et al. |
| 10,682,254 B2 | 6/2020 | Kahook |
| 10,744,033 B2 | 8/2020 | Baerveldt et al. |
| 10,765,556 B1 | 9/2020 | Tarabishy |
| 10,779,991 B2 | 9/2020 | Kahook et al. |
| 10,786,391 B2 | 9/2020 | Kahook |
| 10,857,027 B2 | 12/2020 | Badawi et al. |
| 10,888,453 B2 | 1/2021 | Badawi et al. |
| 10,888,460 B2 | 1/2021 | Sorensen et al. |
| 10,905,591 B1 | 2/2021 | Ianchulev |
| 10,945,885 B2 | 3/2021 | Kahook |
| 10,987,248 B2 | 4/2021 | Mittelstein et al. |
| 11,090,188 B2 | 8/2021 | Badawi et al. |
| 11,110,008 B2 | 9/2021 | Kahook |
| 11,116,660 B2 | 9/2021 | Badawi et al. |
| 11,166,847 B2 | 11/2021 | Badawi et al. |
| 11,291,584 B2 | 4/2022 | Sorensen et al. |
| 11,344,447 B2 | 5/2022 | Badawi et al. |
| 11,364,148 B2 | 6/2022 | Kahook et al. |
| 11,389,327 B2 | 7/2022 | Badawi et al. |
| 11,389,328 B2 | 7/2022 | Badawi et al. |
| 11,419,886 B2 | 8/2022 | Badawi et al. |
| 11,471,324 B2 | 10/2022 | Badawi et al. |
| 11,504,270 B1 | 11/2022 | Badawi et al. |
| 11,554,134 B2 | 1/2023 | Badawi et al. |
| 11,617,679 B2 | 4/2023 | Badawi et al. |
| 11,857,460 B2 | 1/2024 | Badawi et al. |
| 11,865,041 B2 | 1/2024 | Badawi et al. |
| 11,872,158 B2 | 1/2024 | Badawi et al. |
| 11,877,954 B2 | 1/2024 | Badawi et al. |
| 11,925,657 B2 | 3/2024 | Badawi et al. |
| 11,951,037 B2 | 4/2024 | Badawi et al. |
| 12,127,973 B2 | 10/2024 | Badawi et al. |
| 12,127,974 B2 | 10/2024 | Badawi et al. |
| 2001/0029386 A1 | 10/2001 | Matsutani et al. |
| 2002/0026205 A1 | 2/2002 | Matsutani et al. |
| 2002/0111608 A1 | 8/2002 | Baerveldt et al. |
| 2003/0208217 A1 | 11/2003 | Dan |
| 2005/0015104 A1 | 1/2005 | Morawski et al. |
| 2005/0070941 A1 | 3/2005 | Isogimi |
| 2005/0113644 A1 | 5/2005 | Obenchain et al. |
| 2005/0216019 A1 | 9/2005 | Eckman |
| 2005/0245953 A1 | 11/2005 | Cote |
| 2006/0015128 A1 | 1/2006 | Fard |
| 2006/0149194 A1 | 7/2006 | Conston et al. |
| 2006/0241580 A1 | 10/2006 | Mittelstein et al. |
| 2006/0271074 A1 | 11/2006 | Ewers et al. |
| 2007/0073275 A1 | 3/2007 | Conston et al. |
| 2007/0100363 A1 | 5/2007 | Dollar et al. |
| 2009/0137992 A1* | 5/2009 | Nallakrishnan ..... A61F 9/00781 604/294 |
| 2009/0248141 A1 | 10/2009 | Shandas et al. |
| 2009/0287233 A1* | 11/2009 | Huculak ............ A61F 9/00763 606/167 |
| 2009/0306689 A1 | 12/2009 | Welty et al. |
| 2010/0152609 A1 | 6/2010 | Zwolinski et al. |
| 2010/0268175 A1 | 10/2010 | Lunsford et al. |
| 2011/0077626 A1 | 3/2011 | Baerveldt et al. |
| 2011/0202049 A1 | 8/2011 | Jia et al. |
| 2011/0230877 A1 | 9/2011 | Huculak et al. |
| 2012/0083727 A1 | 4/2012 | Barnett |
| 2012/0089165 A1 | 4/2012 | Saxler et al. |
| 2012/0191120 A1 | 7/2012 | Linsi |
| 2012/0239056 A1 | 9/2012 | Dijkman et al. |

(56) References Cited

U.S. PATENT DOCUMENTS

| | | |
|---|---|---|
| 2013/0253402 A1* | 9/2013 | Badawi .................. A61F 9/007 604/8 |
| 2014/0030273 A1 | 1/2014 | Verploegen et al. |
| 2014/0121697 A1 | 5/2014 | Scheller et al. |
| 2015/0051699 A1 | 2/2015 | Badawi et al. |
| 2016/0100980 A1 | 4/2016 | Badawi et al. |
| 2017/0202707 A1 | 7/2017 | Badawi et al. |
| 2020/0107961 A1 | 4/2020 | Kahook et al. |
| 2020/0121503 A1 | 4/2020 | Badawi et al. |
| 2020/0306081 A1 | 10/2020 | Kahook |
| 2020/0306085 A1 | 10/2020 | Mittelstein et al. |
| 2020/0330273 A1 | 10/2020 | Baerveldt et al. |
| 2021/0000648 A1* | 1/2021 | Nallakrishnan .......... A61H 5/00 |
| 2021/0022920 A1* | 1/2021 | Ianchulev ........... A61F 9/00781 |
| 2021/0386584 A1 | 12/2021 | Badawi et al. |
| 2021/0393439 A1 | 12/2021 | Kahook |
| 2022/0160668 A1 | 5/2022 | Badawi et al. |
| 2022/0168146 A1 | 6/2022 | Badawi et al. |
| 2022/0265472 A1 | 8/2022 | Kahook et al. |
| 2022/0280339 A1 | 9/2022 | Badawi et al. |
| 2022/0354695 A1 | 11/2022 | Badawi et al. |
| 2022/0378612 A1 | 12/2022 | Badawi et al. |
| 2023/0098330 A1 | 3/2023 | Pournaras et al. |
| 2023/0181355 A1 | 6/2023 | Badawi et al. |
| 2023/0233371 A1 | 7/2023 | Badawi et al. |
| 2023/0233372 A1 | 7/2023 | Badawi et al. |
| 2023/0277373 A1 | 9/2023 | Badawi et al. |
| 2023/0293347 A1 | 9/2023 | Badawi et al. |
| 2024/0173251 A1 | 5/2024 | Badawi et al. |
| 2024/0225894 A1 | 7/2024 | Needleman et al. |
| 2024/0293257 A1 | 9/2024 | Badawi et al. |
| 2024/0366424 A1 | 11/2024 | Badawi et al. |
| 2024/0415860 A1 | 12/2024 | Badawi et al. |

FOREIGN PATENT DOCUMENTS

| | | |
|---|---|---|
| WO | WO-01/78631 A3 | 10/2001 |
| WO | WO-03/045290 A1 | 6/2003 |
| WO | WO-2004/093761 A1 | 11/2004 |
| WO | WO-2004/110501 A2 | 12/2004 |
| WO | WO-2004/110501 A3 | 12/2004 |
| WO | WO-2009/140185 A1 | 11/2009 |
| WO | WO-2011/030081 A1 | 3/2011 |
| WO | WO-2012/044952 A2 | 4/2012 |
| WO | WO-2012/044952 A3 | 4/2012 |
| WO | WO-2012/137186 A1 | 10/2012 |
| WO | WO-2013/163034 A1 | 10/2013 |
| WO | WO-2017/112893 A1 | 6/2017 |
| WO | WO-2019/083903 A1 | 5/2019 |
| WO | WO-2019/200336 A1 | 10/2019 |

OTHER PUBLICATIONS

International Search Report mailed on Aug. 30, 2023, for PCT Application No. PCT/US2023/0015327, filed on Mar. 15, 2023, 4 pages.

Jacobi, P.C. et al. (1997). "Technique of goniocurettage: a potential treatment for advanced chronic open angle glaucoma," Br. J. Ophthalmol. 81:302-307.

Non-Final Office Action mailed on Jun. 1, 2023, for U.S. Appl. No. 18/122,109, filed Mar. 15, 2023, 11 pages.

Notice of Allowance mailed on Sep. 27, 2023, for U.S. Appl. No. 18/122,109, filed Mar. 15, 2023, 8 pages.

Quintana, M. (1984). "Gonioscopic trabeculotomy. First results," Second European Glaucoma Symposium, Documenta Ophthalmologica Proceedings Series 43, pp. 265-271.

Sight Sciences, Inc. (Aug. 23, 2022). "Sight Sciences introduces the SION™ surgical instrument—The first bladeless device used in goniotomy," Press Release, Menlo Park, California, 3 total pages.

SION™ Brochure Accessible Aug. 2022. Sight Sciences, Inc., 4 total pages.

Written Opinion of the International Searching Authority mailed on Aug. 30, 2023, for PCT Application No. PCT/US2023/0015327, filed on Mar. 15, 2023, 14 pages.

Non-Final Office Action mailed on Apr. 14, 2025, for U.S. Appl. No. 18/122,108, filed on Mar. 15, 2023, 16 pages.

* cited by examiner

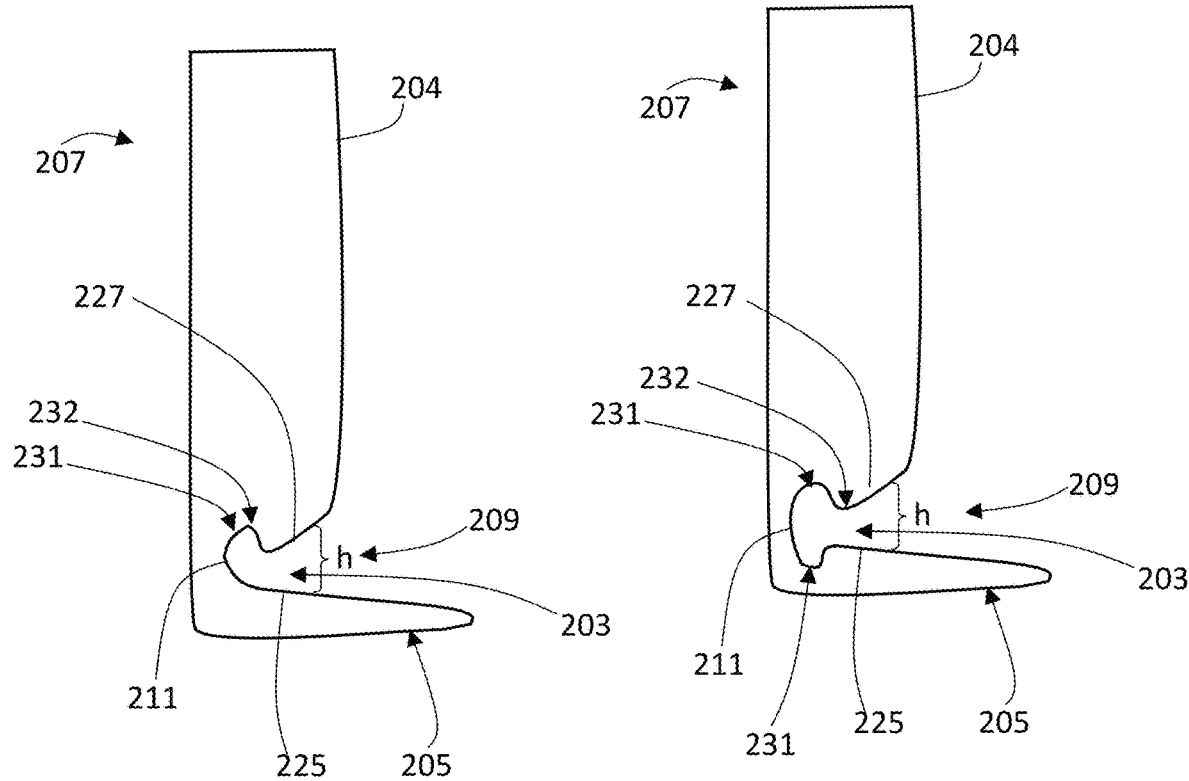
*FIG. 7A*  *FIG. 7B*

FIG. 14A  FIG. 14B  FIG. 14C

DEVICES AND METHODS FOR INTRAOCULAR TISSUE MANIPULATION

CROSS-REFERENCE TO RELATED APPLICATIONS

This application is a continuation of U.S. patent application Ser. No. 18/122,109, filed Mar. 15, 2023, which claims priority to U.S. Provisional Patent Application No. 63/320,643, filed Mar. 16, 2022, and U.S. Provisional Patent Application No. 63/392,971, filed Jul. 28, 2022, the contents of each of which is hereby incorporated in its entirety by this reference.

TECHNICAL FIELD

Described here are bladeless devices and methods for manipulating or tearing tissue, including, for example, manipulating or tearing intraocular tissue such as trabecular meshwork.

BACKGROUND

Glaucoma is a potentially blinding disease that affects over 60 million people worldwide, or about 1-2% of the population. Typically, glaucoma is characterized by elevated intraocular pressure. Increased pressure in the eye can cause irreversible damage to the optic nerve which can lead to loss of vision and even progress to blindness if left untreated. Consistent reduction of intraocular pressure can slow down or stop progressive loss of vision associated with glaucoma.

Increased intraocular pressure is generally caused by sub-optimal efflux or drainage of fluid (aqueous humor) from the eye. Aqueous humor or fluid is a clear, colorless fluid that is continuously replenished in the eye. Aqueous humor is produced by the ciliary body, and then ultimately exits the eye primarily through the trabecular meshwork. The trabecular meshwork extends circumferentially around the eye at the anterior chamber angle, or drainage angle, which is formed at the intersection between the peripheral iris or iris root, the anterior sclera or scleral spur and the peripheral cornea. The trabecular meshwork feeds outwardly into Schlemm's canal, a narrow circumferential passageway generally surrounding the exterior border of the trabecular meshwork. Positioned around and radially extending from Schlemm's canal are aqueous veins or collector channels that receive drained fluid. The net drainage or efflux of aqueous humor can be reduced as a result of decreased facility of outflow, decreased outflow through the trabecular meshwork and canal of Schlemm drainage apparatus, increased episcleral venous pressure, or possibly, increased production of aqueous humor. Flow out of the eye can also be restricted by blockages or constriction in the trabecular meshwork and/or Schlemm's canal and its collector channels.

Glaucoma, pre-glaucoma, and ocular hypertension currently can be treated by reducing intraocular pressure using one or more modalities, including medication, incisional surgery, laser surgery, cryosurgery, and other forms of surgery. In general, medications or medical therapy are the first lines of therapy. Should medical therapy fail, not be tolerated, or not be possible, other forms of therapy may be added or substitute to medical therapy. For example, laser therapy to the eye in the form of trabeculoplasty, cycloablation (endoscopic or transscleral) may be performed. In more advanced cases or under some circumstances, incisional surgery can be considered. Trabeculectomy (surgical removal or ablation of trabecular meshwork), valves, or shunts can be used to help control intraocular pressure. Recently, minimally invasive glaucoma surgery ("MIGS") has become a popular surgical approach to the treatment of glaucoma. Various technologies are being employed to reduce intraocular pressure while reducing exposure to surgical risks posed by more invasive treatments like trabeculectomy or valve placement. While surgical therapy of glaucoma was traditionally reserved as a last line of therapy in the United States, the advent of MIGS types of procedures allows for surgery to be considered earlier and in a safer fashion. In 2017, nearly 175,000 surgical procedures were performed. The surgeries included over 20,000 trabeculectomies, 20,000 glaucoma drainage implants, and over 130,000 MIGS procedures.

One target of MIGS surgery is the trabecular meshwork. The trabecular meshwork has been historically viewed as the region of highest resistance to aqueous outflow. For example, a standard incisional surgical procedure to reduce intraocular pressure is trabeculectomy, or filtration surgery. A trabeculectomy procedure may be referred to in the art as a trabeculotomy, ab interno trabeculotomy, goniotomy, or excisional goniotomy. This procedure involves creating a new drainage site for aqueous humor. By way of example, instead of naturally draining through the trabecular meshwork, a new drainage pathway is created by removing a portion of sclera and/or trabecular meshwork at the drainage angle. This creates an opening or passage between the anterior chamber and the subconjunctival space that is drained by conjunctival blood vessels and lymphatics. The new opening may be covered with sclera and/or conjunctiva to create a new reservoir called a bleb into which aqueous humor can drain. However, traditional trabeculectomy, especially ab externo trabeculectomy, procedures carry both short- and long-term risks. These risks include blockage of the surgically created opening through scarring or other mechanisms, hypotony or abnormally low intraocular pressure, expulsive hemorrhage, hyphemia, intraocular infection or endophthalmitis, shallow anterior chamber angle, macular hypotony, choroidal exudation, suprachoroidal hemorrhage, and others. These complications may arise, by way of example, from incidental or unintended damaged made to surrounding tissue caused by extraneous incisions made by sharp cutting surfaces or electrogenic and/or thermogenic damage caused by cautery mechanisms that are typically used to cut or destroy portions of the trabecular meshwork during trabeculectomy.

Accordingly, there is a need for an improved trabeculectomy or goniotomy devices and methods that induce less incidental trauma and damage to surrounding tissue.

BRIEF SUMMARY

Described herein are systems, devices, and methods of manipulating and tearing tissue such as intraocular tissue, by way of example and in some variations, for easily and reliably accessing Schlemm's canal and tearing or stripping off trabecular meshwork with minimal or reduced trauma.

In some variations, a bladeless device for tearing trabecular meshwork of an eye of a subject may comprise a shaft, and a tip coupled to the shaft, the tip comprising: an elongate lower foot configured to be inserted into Schlemm's canal; an elongate upper foot positioned proximally of the lower foot; and a groove formed between the lower foot and the upper foot and configured to grasp a portion of the trabecular meshwork.

In some variations, the groove may comprise a front opening and a closed back, and wherein the front opening is aligned with the tip of the upper foot. In some variations, the groove may comprise a first side and a second side, wherein the first and second sides are open. In some variations, the groove may comprise an upper grabbing surface that is coextensive with at least a portion of a plantar surface of the upper foot and a lower grabbing surface that is coextensive with at least a portion of a dorsal surface of the lower foot. In some variations, a height of the groove may decrease along a central longitudinal axis of the upper foot from a tip of the upper foot toward the shaft. In some variations, the closed back of the groove may be rounded. In some variations, a radius of curvature of the closed back of the groove is at least 10 microns, at least 15 microns, at least 20 microns, about 10 microns, about 15 microns, or about 20 microns. In some variations, the closed back of the groove may be atraumatic. In some variations, all surfaces and corners of the tissue grabber may be atraumatic. In some variations, all surfaces and corners of the tissue grabber may be atraumatic except for the tip of the lower foot.

In some variations, the tip may comprise a tissue collection opening located at a surface of the groove, which may comprise one or more of the upper groove surface, the lower groove surface, and the closed back of the groove. Optionally, tissue collection opening may be an indentation formed on a surface of the groove which may comprise one or more of the upper groove surface, the lower groove surface, and the closed back of the groove. Optionally, the tissue collection opening may be a window through the lower foot, the upper foot, or a closed back of the groove In some variations, the tissue grabber may comprise a roughened surface. Optionally, the roughened surface may be located on a surface of the groove, which may comprise one or more of the upper groove surface, the lower groove surface, and the closed back. In some variations, all surfaces of the tissue grabber may be electropolished except for the roughened surface, which is left unpolished. In some variations, the roughened surface may comprise a coating applied to one or more of the upper groove surface, the lower groove surface, and the closed back, and wherein the coating comprises granules, optionally diamond dust. In some variations, the roughened surface may comprise an array of micron-scale indentations.

In some variations, tissue grabber may comprise one or more protrusions formed on one or more of the upper groove surface, the lower groove surface, and the closed back. In some variations, the protrusions may be in the shape of teeth, spikes, or barbs.

In some variations, a length of the lower foot may be greater than a length of the upper foot. In some variations, the device may be configured such that at least a tip of the lower foot is visible through the trabecular meshwork when the lower foot is positioned within Schlemm's canal.

In some variations, a maximum width of the upper foot may be greater than a maximum width of the lower foot. In some variations, the maximum width of the upper foot may exceed a width of Schlemm's canal. In some variations, the device may be configured such that the upper foot presses on a scleral spur, the trabecular meshwork, and Schwalbe's line of the eye when the lower foot is positioned within Schlemm's canal.

In some variations, the shaft and the tissue grabber may be integral. In some variations, the shaft and the tissue grabber may be formed separately and attached using one or more of connectors, bonding, and welding. In some variations, the shaft and the tissue grabber may be formed of a metal, a rigid polymer, or a composite.

In some variations, the device may be configured to tear a second, different portion of the trabecular meshwork when the lower foot is positioned within, and advanced relative to, Schlemm's canal.

In some variations, a device for grasping trabecular meshwork of an eye of a subject may comprise a shaft extending along a longitudinal axis and comprising a distal end, and a tissue grabber positioned at the distal end of the shaft, the tissue grabber comprising: a lower foot configured to be inserted into Schlemm's canal, the lower foot comprising a central longitudinal axis that is transverse to the longitudinal axis of the shaft; an upper foot positioned proximally of the lower foot and configured to be positioned over the trabecular meshwork, the upper foot comprising a second central longitudinal axis; and a groove formed between the lower foot and the upper foot and configured to grab a portion of the trabecular meshwork. In some variations, the first and second central longitudinal axes may be about parallel. In some variations, the groove may comprise a variable height. In some variations, the lower foot may be longer than the upper foot. In some variations, the upper foot may be wider than the lower foot.

In some variations, a device for grasping trabecular meshwork of an eye of a subject may comprise a shaft extending along a longitudinal axis and a tissue grabber positioned at a distal end of the shaft, the tissue grabber comprising: a foot comprising a central longitudinal axis that is transverse to the longitudinal axis of the shaft, the foot being configured to be inserted into Schlemm's canal; a proximal portion connected to the shaft and to the foot; and a grabbing surface comprising a surface on the proximal portion and a dorsal surface of the foot. In some variations, the grabbing surface may be configured to have a higher coefficient of friction compared to remaining surfaces of the tissue grabber. In some variations, the coefficient of friction may be a static coefficient of friction with respect to a tissue contacting the grabbing surface. In some variations, the other surfaces of the tissue grabber may be electropolished and the grabbing surface may not be electropolished. In some variations, the grabbing surface is treated with a coating comprising granules. In some variations, the grabbing surface comprises protrusions that are optionally in the shape of teeth, spikes, or barbs.

In some variations, a bladeless device for tearing trabecular meshwork of an eye of a subject may comprise a shaft comprising a distal end and a bladeless tip coupled to the distal end of the shaft, the tip comprising: an elongate lower foot configured to be inserted into Schlemm's canal, the lower foot comprising a central longitudinal axis that is transverse to a longitudinal axis of the shaft; an elongate upper foot positioned proximally of the lower foot and configured to be positioned over the trabecular meshwork; and a groove formed between the lower foot and the upper foot and configured to grasp a portion of the trabecular meshwork. In some variations, the groove has variable height. Optionally, the height of the groove decreases along a central longitudinal axis of the upper foot from a tip of the upper foot toward the shaft. In some variations, the lower foot may be longer than the upper foot. In some variations, the upper foot may be wider than the lower foot.

In some variations, a bladeless device for tearing trabecular meshwork of an eye of a subject may comprise a shaft comprising a distal end, and a tip coupled to the distal end of the shaft, the tip comprising: an elongate lower foot configured to be inserted into Schlemm's canal, the lower foot comprising a central longitudinal axis that is transverse to a longitudinal axis of the shaft; an elongate upper foot positioned proximally of the lower foot and configured to be positioned over the trabecular meshwork; and a groove formed between the lower foot and the upper foot and configured to grasp a portion of, and tear without cutting, the trabecular meshwork. In some variations, the groove has variable height. Optionally, the height of the groove decreases along a central longitudinal axis of the upper foot from a tip of the upper foot toward the shaft. In some variations, the lower foot may be longer than the upper foot. In some variations, the upper foot may be wider than the lower foot.

In some variations, a method of tearing trabecular meshwork of an eye of a subject may comprise: advancing a tissue grabber at a distal end of a shaft to Schlemm's canal of the eye, wherein the tissue grabber comprises a lower foot and a groove; advancing a tip of the lower foot through the trabecular meshwork and into Schlemm's canal; and advancing the lower foot within and relative to Schlemm's canal, wherein as the lower foot is advanced, a first central portion of the trabecular meshwork becomes trapped in the groove and a second, lateral portion of the trabecular meshwork is detached from surrounding tissue. In some variations, portion of the trabecular meshwork may be detached from Schwalbe's line and the scleral spur. In some variations, the method comprises withdrawing the tip from Schlemm's canal, thereby withdrawing the detached portion of the trabecular meshwork along with the tissue grabber.

In some variations, as the lower foot is advanced further within Schlemm's canal, a detached portion of the trabecular may form a ribbon trailing the first portion of the trabecular meshwork trapped in the groove. In some variations, the method may comprise rotating the tip along a longitudinal axis of the shaft before withdrawing the tip from the eye, thereby wrapping the detached portion of the trabecular meshwork around the shaft.

In some variations, the subject may be suffering from high intraocular pressure, optionally caused by glaucoma.

BRIEF DESCRIPTION OF THE DRAWINGS

FIGS. 7A-7E show variations of a tissue grabber.

FIGS. 14A-14E show steps of a tearing goniotomy procedure performed with a tissue manipulation and/or tissue tearing device.

DETAILED DESCRIPTION

Figure 1:
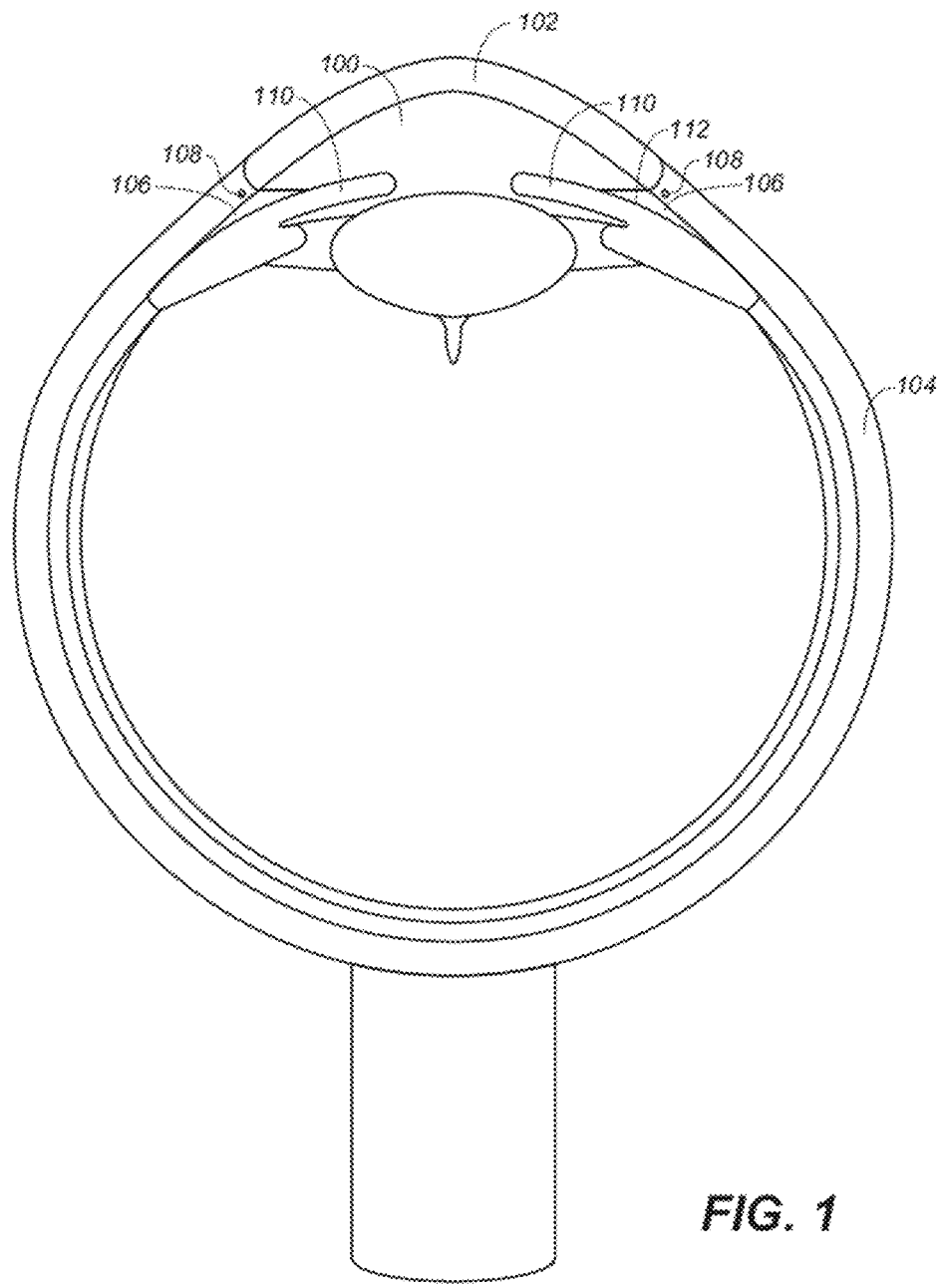
FIG. 1 shows a stylized, cross-sectional view of the eye.

The following description, for purposes of explanation, uses specific nomenclature to provide a thorough understanding of the invention. The foregoing descriptions of specific variations of the invention are presented for purposes of illustration and description. They are not intended to be exhaustive or to limit the invention to the precise forms disclosed; obviously, many modifications and variations are possible in view of the teachings disclosed herein.

As used herein, "treat" or "treating" a disease or condition may mean to reduce, alleviate, and/or eliminate one or more symptoms of the disease or condition. For instance, a method of treating glaucoma disclosed herein may result in the reduction of one or more symptoms of glaucoma, by way of example, high intraocular pressure.

Described herein are devices and methods for manipulating, grabbing, trapping, tearing, pulling, stripping, and/or removing portions of intraocular tissue, such as, for example, trabecular meshwork. Removal of the trabecular meshwork, which may be referred to in the art as trabeculotomy, ab interno trabeculotomy, trabeculectomy, ab interno trabeculectomy, goniotomy, or excisional goniotomy may be performed in accordance with the method described herein, using variations of the devices described herein, to improve flow through the trabeculocanalicular outflow pathway and reduce intraocular pressure, thereby treating conditions of the eye, such as high intraocular pressure caused by glaucoma.

In some variations, the devices and methods described herein may be used to grab and trap tissue (e.g., trabecular meshwork), and to tear tissue (e.g., trabecular meshwork and/or surrounding tissue) facilitating removal of a portion of the tissue (e.g., trabecular meshwork) from the eye. The devices and methods described herein may sever, separate, or otherwise disassociate tissue, such as a portion of the trabecular meshwork, from surrounding tissue, such as Schwalbe's ring and/or the scleral spur, without the use of knives, blades, or other sharpened edges or structures. As such, variations of devices described herein may be referred to as bladeless devices, or bladeless goniotomy devices, and may confer safety and efficacy advantages over bladed goniotomy devices.

The devices and methods described herein may provide several advantages as compared to conventional goniotomy devices and techniques. While conventional goniotomy devices or trabectomes (excisional goniotomy devices) utilize one or more blades (typically two) or energy (e.g., electrodes) to cut or ablate the trabecular meshwork, the devices and methods described herein utilize atraumatic surfaces to grip, trap, and ultimately tear the trabecular meshwork with pulling force instead of cutting or ablating it. The bladeless devices and methods described herein result in an unexpectedly easy, effective, and low trauma goniotomy procedure. Conventional techniques cut or ablate the meshwork as the goniotomy devices come into contact with the tissue. By contrast, certain variations of the devices and methods described herein may allow for lateral portions of the trabecular meshwork (such as the roots) to be avulsed or stripped through an indirect application of pulling forces on the tissue that occurs behind the device, that results, unexpectedly, in both a more gentle and more thorough removal of larger segments of the unwanted tissue. In addition, whereas conventional goniotomy devices require a second, separate tool such as forceps to remove the tissue cut by the trabectome, the devices and methods described herein advantageously allow for both the disassociation and removal of tissue to be performed using a single device by atraumatically holding, or grabbing, tissue in advance of tearing it.

To better understand the systems and methods described here, it may be useful to explain some of the basic eye anatomy. FIG. 1 is a stylized depiction of a normal human eye. The anterior chamber 100 is shown as bounded on its anterior surface by the cornea 102. The cornea is connected on its periphery to the sclera 104, which is a tough fibrous tissue forming the protective white shell of the eye. Trabecular meshwork 106 is located on the outer periphery of the anterior chamber 100 and extends 360 degrees circumferentially around the anterior chamber. Located on the outer peripheral surface of the trabecular meshwork 106 is Schlemm's canal 108. Schlemm's canal 108 extends 360 degrees circumferentially around the meshwork 106. At the apex formed between the iris 110, meshwork 106, and sclera 104, is the anterior chamber angle 112.

Devices described herein may generally comprise a shaft and a tissue grabber (which may also be referred to as a tissue grabbing tip, and in variations in which devices are utilized to tear tissue, a tissue tearing tip) positioned at a distal end of shaft. The tissue grabber may comprise a tissue grabbing region comprising a groove, mouth, crevice, cavity, indentation, gap, open space, notch, or other feature that is configured to receive and grab a portion of tissue. The tissue grabber may be a rigid, static object or component with no moving, motorized, or articulated parts. In some variations, the tissue grabber (or optionally the tissue grabber and the shaft or portion thereof) may be formed as an integral object by way of example out of metal through laser machining or EDM (electrical discharge machining). The tissue grabber may be configured to be atraumatic and devoid of cutting edges such as blades or other sharpened edges, so that the portion of tissue that enters the tissue grabbing region is not cut by the tissue grabber, but rather becomes stuck therein or thereon. As such, when the tissue grabber is advanced or otherwise moved, the tissue caught in the tissue grabbing region is advanced or moved with the tissue grabber. In variations in which the devices described herein are utilized to tear tissue, advancement of the tissue grabber (or tissue tearing tip) relative to surrounding tissue may result in stretching the surrounding tissue and ultimately, tearing the surrounding tissue, thereby facilitating removal of the tissue positioned in or on the tissue grabber.

In variations in which the devices described herein are used to access and remove portions of the trabecular meshwork, the devices described herein may be advanced to Schlemm's canal (e.g., ab interno or ab externo) and at least a portion of the tissue grabber may enter Schlemm's canal. The tissue grabbing region may grip, grab, or otherwise hold a portion of the trabecular meshwork while the tissue grabber is advanced relative to the canal. As the tissue grabber is advanced, the nearby portions of the trabecular meshwork not positioned within the tissue grabbing region (e.g., outside of the tissue grabber, adjacent to the tissue grabber) may be stretched and eventually torn and detached from surrounding tissue. As the tissue grabber is further advanced through the canal, additional sections of the trabecular meshwork may be torn and separated from surrounding tissue, and these additional sections may wholly or partially be gathered or collected within or on the tissue grabber (e.g., within the tissue grabbing region). Regardless of whether these additional sections of trabecular meshwork themselves remain within or on the tissue grabber, they may remain attached to the portion of the trabecular meshwork that is stuck or otherwise positioned within or on the tissue grabber. These additional sections of trabecular meshwork may form a trailing portion of tissue as this portion of the separated trabecular meshwork may trail the portion positioned within or on the tissue grabber but may be otherwise free of attachment to tissue. The portion of the trabecular meshwork positioned within or on the tissue grabber, and the trailing portion, if present, may be removed from the eye utilizing the devices described herein, thereby improving flow through the trabeculocanalicular outflow. While the devices and methods described herein advantageously allow for removal of undesired tissue (e.g., trabecular meshwork) from the eye without the need for additional tools, it should be appreciated that forceps or other tissue graspers may be used instead of, or in addition to, using the devices described herein to remove the undesired tissue once it has been separated from surrounding tissue. Additionally, while described above for use in tearing and removing a portion of the trabecular meshwork, it should be appreciated that the devices of the present disclosure may be used to manipulate, tear, and/or remove any intraocular tissue in any appropriate surgical procedure, and are not limited to use in trabeculectomies or goniotomies.

Devices

The devices described herein may generally include a handle configured to be held in a hand of a user, a shaft extending along a longitudinal axis and having a proximal end connected to the handle, and a tissue grabber comprising a tissue grabbing region located at a distal end of the shaft. In some variations, the handle and the shaft may be integral, such that the handle may simply be a portion of the shaft that is configured to be help in a hand of a user. Additionally or alternatively, in some variations, the tissue grabber and the shaft may be integral.

Figure 2A:
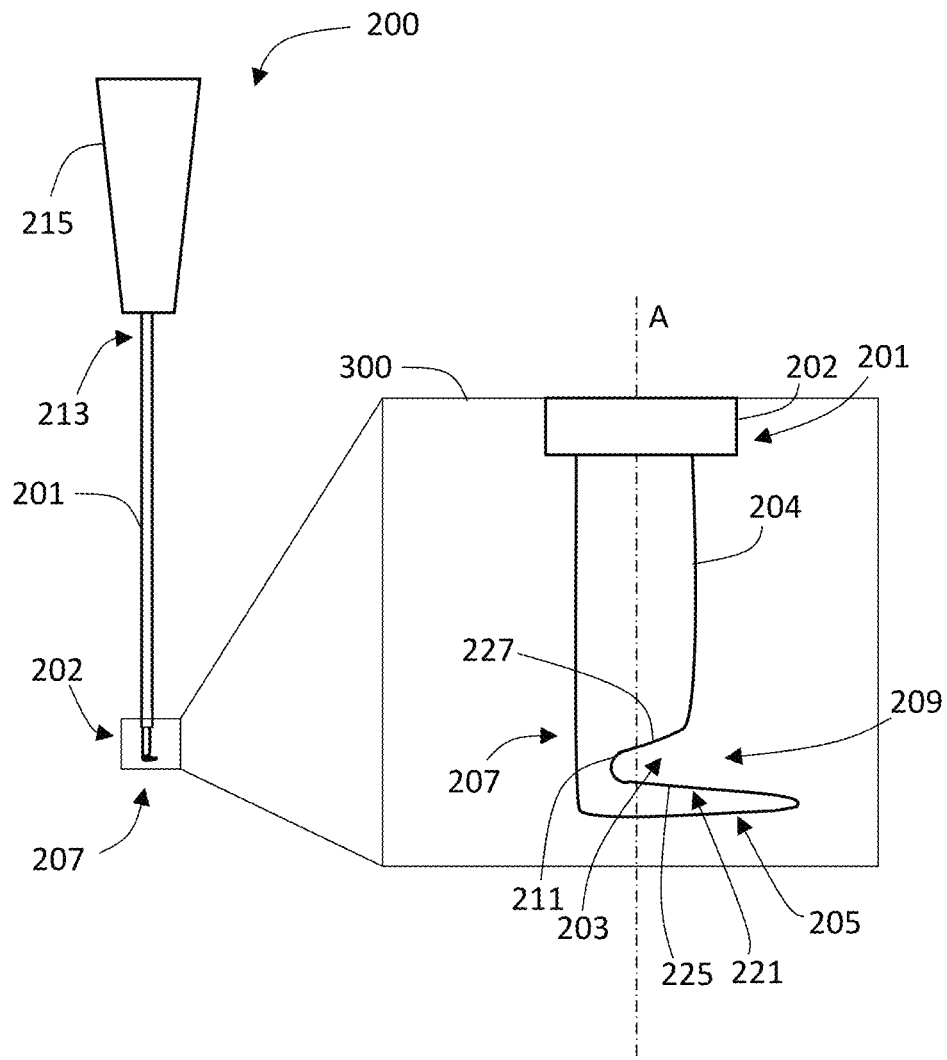
FIG. 2A depicts a variation of a tissue manipulation and/or tearing device.

FIG. 2A depicts an exemplary variation of a tissue manipulation and/or tearing device 200. As shown there, the tissue manipulation and/or tearing device 200 may comprise a shaft 201 and a tissue grabber 207 positioned at or otherwise coupled to a distal portion 202 of the shaft 201. The proximal end 213 of the shaft 201 may be connected to a handle 215, which may have any shape and form suitable to be held in a hand of a user using the device.

Inset 300 depicts a magnified view of the tissue grabber 207. The tissue grabber 207 may comprise a proximal portion 204, a guide foot 205 coupled to the proximal portion 204 and configured to be inserted into Schlemm's canal, and a tissue grabbing region 203 formed between the guide foot 205 and the proximal portion 204. The tissue grabber 207 may be a rigid, static object or component with no moving, motorized, or articulated parts. In some variations, the tissue grabber 207 may be formed as an integral object by way of example through laser machining or EDM (electrical discharge machining). The tissue grabber 207 may comprise any material suitable for surgical use, such as a metal, for example, stainless steel, nitinol, titanium, or the like. The tissue grabbing region 203 may provide an opening where tissue (such as a trabecular meshwork) may be inserted for pulling and removal through tearing, stripping, ripping, and/or avulsion. The proximal portion 204 may function as an intermediary component to connect directly or indirectly the rest of the tissue grabber 207 to the distal portion 202 of the shaft 201. The proximal portion 204 may have a length of between about 5 mm and about 0.5 mm along its longitudinal axis, which may be coextensive and/or parallel with the longitudinal axis of the shaft 201. As used herein, "about" may refer to a value within ±5% of the recited value. In some variations, the shape and/or width of the proximal portion 204 may be the same as the shaft 201, in which case the proximal portion 204 may appear to be coextensive with the distal end 202 of the shaft 201. In some variations, the width of the proximal portion 204 may be less than that of the shaft 201, which may allow the shaft to be relatively sturdy while allowing the tissue grabber 207 to be dimensioned for accessing tissues of relatively small dimensions, such as the trabecular meshwork and Schlemm's canal. In some variations, the width of the proximal portion 204 may be between about 50% and about 2% of the width of the shaft, or about 50%, about 40%, about 30%, about 20%, about 10%, about 5%, or about 2% of the width of the shaft. In some variations, the proximal portion 204 of the tissue grabber 207 may be integrally formed with a distal portion 202 of the shaft. In other variations, the shaft 201 and the tissue grabber 207 may be formed separately and the proximal portion 204 of the tissue grabber may be fixedly or removably attached to the distal portion 202 of the shaft using any suitable technique, such as, for example, welding, soldering, bonding, riveting, connectors (e.g., snap-fit connectors, threaded connectors), and the like.

The tissue grabbing region 203 may comprise an upper grabbing surface 227 and a lower grabbing surface 225 that connect at a closed back 211, and may comprise a front opening 209. In certain variations, the tissue grabbing region 203 may comprise a first side and a second side, wherein the first and second sides are open. The tissue grabber 207 may be configured to receive, trap, hold, or otherwise maintain a portion of tissue (e.g., the trabecular meshwork) within or on the tissue grabbing region 203. When used to perform a trabeculectomy or goniotomy, the front opening 209 may be configured to receive trabecular meshwork therethrough, with the upper grabbing surface 227 placed above the trabecular meshwork and the lower grabbing surface placed inside Schlemm's canal and therefore, under the trabecular network. Lower grabbing surface 225 may be coextensive with a portion of a dorsal surface 221 of guide foot 205.

The devices described herein may generally be configured for single-handed manipulation and for control by a single operator, and may include features useful for easily accessing, manipulating, and/or removing ocular tissue with minimal trauma. As such, proximal end 213 of shaft 201 may be connected to a handle 215, which may have any shape and form suitable configured to be held in a hand of a user using the device.

Shaft

Figure 2B:
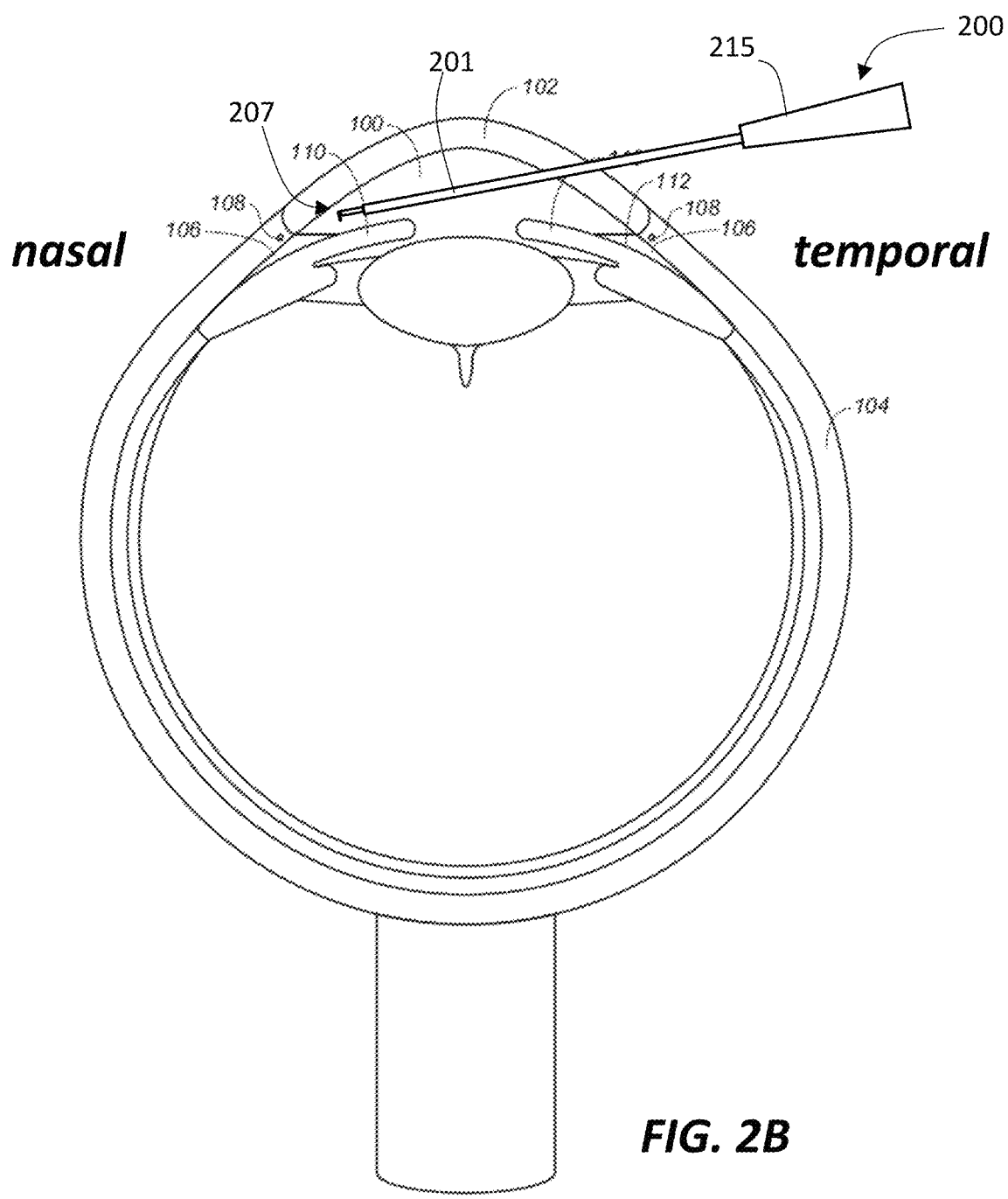
FIG. 2B shows a variation of a tissue manipulation and/or tearing device inserted into an anterior chamber of an eye.
Figure 3A:
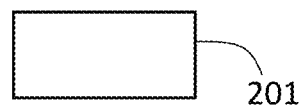
FIGS. 3A-3F show cross-sectional views of variations of a shaft of a tissue manipulation and/or tearing device.
Figure 3B:
Figure 3C:
Figure 3D:
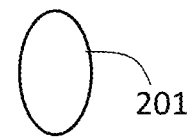
Figure 3E:
Figure 3F:
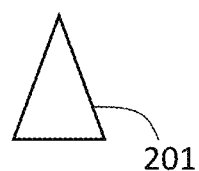

As noted above, the shaft 201 may couple the tissue grabber to the handle, or may otherwise provide a handle for the user, and may allow a user to access intraocular spaces, such as Schlemm's canal, with the tissue grabber while the handle remains outside the eye, as depicted in FIG. 2B. For example, in some variations, the shaft 201 may have a length along a longitudinal axis A configured to allow the tissue grabber 207 to access and be inserted into a particular tissue structure, e.g. Schlemm's canal 108, while the handle 215 remains outside of a subject/patient's eye for manipulation by a user. In some variations, the shaft may have a length between about 0.5 cm and about 15 cm, between about 2 cm and about 10 cm, between about 3 cm and about 5 cm, between about 3 cm and about 10 cm, between about 4 cm and about 10 cm, between about 10 cm and about 15 cm, about 0.5 cm, about 1 cm, about 2 cm, about 3 cm, about 4 cm, about 5 cm, about 6 cm, about 8 cm, about 10 cm, about 12 cm, and about 15 cm. The shaft 201 may comprise any material suitable for surgical use, such as a rigid polymer, a composite, or a metal, for example, stainless steel, nitinol, titanium, or the like.

The shaft 201 may have any cross-sectional shape suitable for insertion into the anterior chamber. For example, as depicted in FIGS. 3A-3F, the cross-sectional shape of the shaft may be rectangular, square, circular, oval, trapezoidal, or triangular.

The shaft 201 may be sized for intraocular access, such as ab interno or ab externo entry into the anterior chamber 100. For example, the maximum cross-sectional width of shaft 201 may be between about 250 microns and about 1000 microns, between about 250 microns and about 1500 microns, between about 250 microns and about 2000 microns, between about 300 microns and about 800 microns, between about 300 microns and about 600 microns, about 250 microns, about 300 microns, about 350 microns, about 400 microns, about 450 microns, about 500 microns, about 550 microns, about 600 microns, about 650 microns, about 700 microns, about 750 microns, about 800 microns, about 850 microns, about 900 microns, about 950 microns, about 1000 microns, about 1500 microns, and about 2000 microns.

In some variations, surface of the shaft 201 may be polished or electropolished. In some variations, surface of the shaft 201 may be coated with a coating, such as a polymer coating or a ceramic coating.

Figure 15:
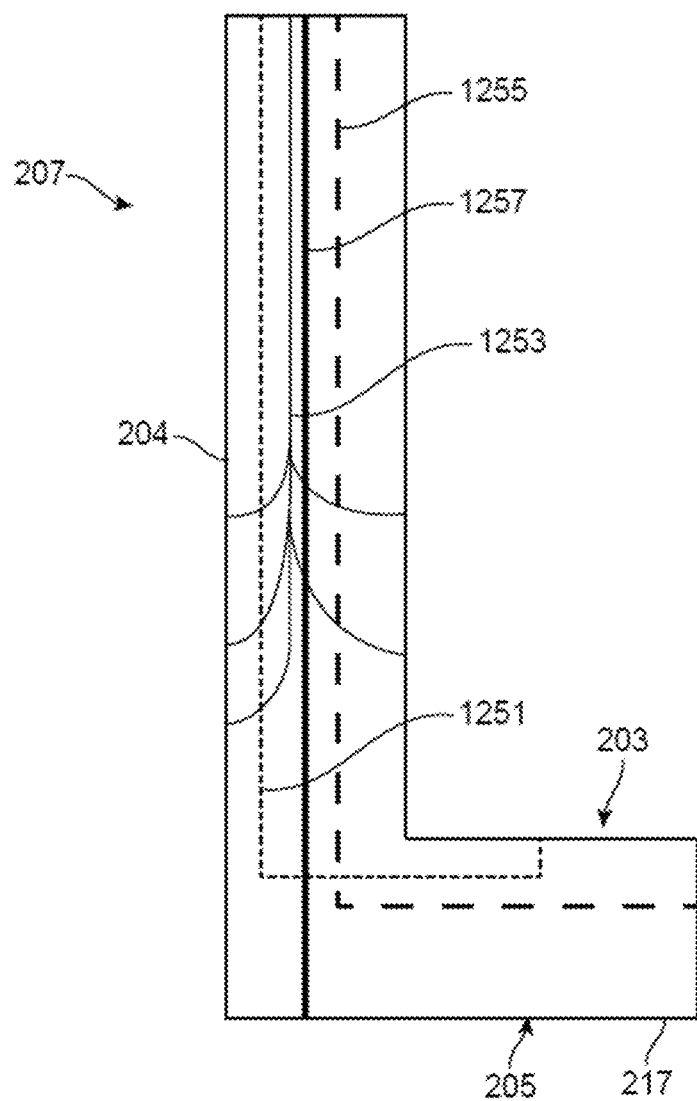
FIG. 15 depicts a variation of a tissue grabber comprising one or more lumens.

In some variations, the shaft 201 may be solid, while in other variations the shaft 201 and optionally the tissue grabber 207 or portions thereof such as proximal portion 204, may comprise one or more lumens therethrough, which may be used by way of example for application of suction, ejection of a fluid such as saline, viscoelastic, and/or formulation comprising a pharmaceutical or therapeutic agent, or providing a pathway for an optical fiber. The one or more lumens may comprise a lumen within the shaft 201 and parts of tissue grabber 207. Several examples of such lumens are shown in FIG. 15. In some variations, the tissue grabber 207 comprises a lumen 1255 that traverses the length of the shaft 201, the proximal portion 204 and the guide foot 205 and opens at a port on the tip 217 of the guide foot. In some variations, the tissue grabber 207 comprises a lumen 1253 that opens at one or more ports on a surface of the proximal portion 204. In some variations, the tissue grabber 207 comprises a lumen 1257 that traverses the length of the shaft 201 and the proximal portion 204 to open at a port on the distal end of the proximal portion 204. In some variations, the tissue grabber 207 comprises a lumen 1251 that traverses the length of the shaft 201, the proximal portion 204 and a portion of the guide foot 205 to open at a port on the dorsal surface of the guide foot 205.

Figure 16:
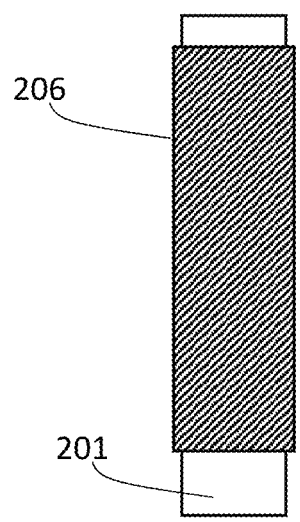
FIG. 16 shows a variation of a shaft of a tissue manipulation and/or tearing device including a sleeve.

Additionally or alternatively, as schematically depicted in FIG. 16, the tissue manipulation and/or tearing devices described herein may further comprise a sleeve 206 positioned around the shaft 201. In some variations, the sleeve may be configured to protect the tissue grabber 207 prior to its use. In some variations, the sleeve 206 may be configured to provide an interstitial space between the shaft 201 and the sleeve, to provide a conduit for suction or a fluid such as saline and/or viscoelastic. The sleeve may comprise any material suitable for surgical instrumentation, such as stainless steel, nitinol, titanium, or the like. Alternatively, the sleeve may comprise a flexible material such as a flexible polymer, rubber, silicone, or the like.

Tissue Grabber

The devices described herein generally comprise a tissue grabber (also referred to as a tissue grabbing tip or a tissue tearing tip) configured to grip and/or trap tissue. As shown in FIG. 2A, the tissue grabber 207 may be located at or near the distal end 202 of the shaft 201 and may comprise a tissue grabbing region 203 that is configured to receive and grab a portion of the trabecular meshwork, one or more elongate feet, and a proximal portion 204 that connects the rest of the tissue grabber 207 to the distal end of the shaft 201. The proximal portion 204 may have a length of between about 0.5 mm and about 3 mm, about 0.5 mm, about 1 mm, about 2 mm, or about 3 mm. In some variations, the tissue grabber 207 may comprise a guide foot 205 that may be configured to be inserted into Schlemm's canal. In some variations, the tissue grabber may comprise a tissue grabbing region and a guide foot, while in other variations, the tissue grabber may comprise a lower guide foot, an upper foot, and a tissue grabbing region located between the lower guide foot and the upper foot. In some variations, the tissue grabber 207, at the tissue grabbing region 203, may comprise one or a combination of two or more tissue grabbing mechanisms such as a variable height of the tissue grabbing region, tissue collection openings (which may be windows or indentations), and tissue grabbing protrusions.

Conventional goniotomy devices typically comprise a tissue cutting component to cut or ablate an approaching portion of the trabecular meshwork, by way of example a blade, a groove that ends in a sharp corner designed to pinch-cut a piece of trabecular meshwork pressed therein, an electrogenic and/or thermogenic ablation mechanism such as an electrode or an optical fiber connected to a light or laser source, or a high-pressure nozzle to release saline for mechanical ablation. By contrast, in some variations, the surfaces of the tissue grabber 207 may be free of any tissue cutting components. As such, the tissue grabber 207 in some variations may be bladeless, and may lack any tissue cutting components, such as, for example, sharp edges or corners, or other features configured to cut tissue (e.g., blades or grooves forming a cutting edge). In some variations, all surfaces surrounding the tissue grabbing region 203 (e.g., portions of surfaces of the guide foot, upper foot, distal end of the shaft), may have rounded or otherwise atraumatic edges.

Tissue Grabbing Region

Figure 4A:
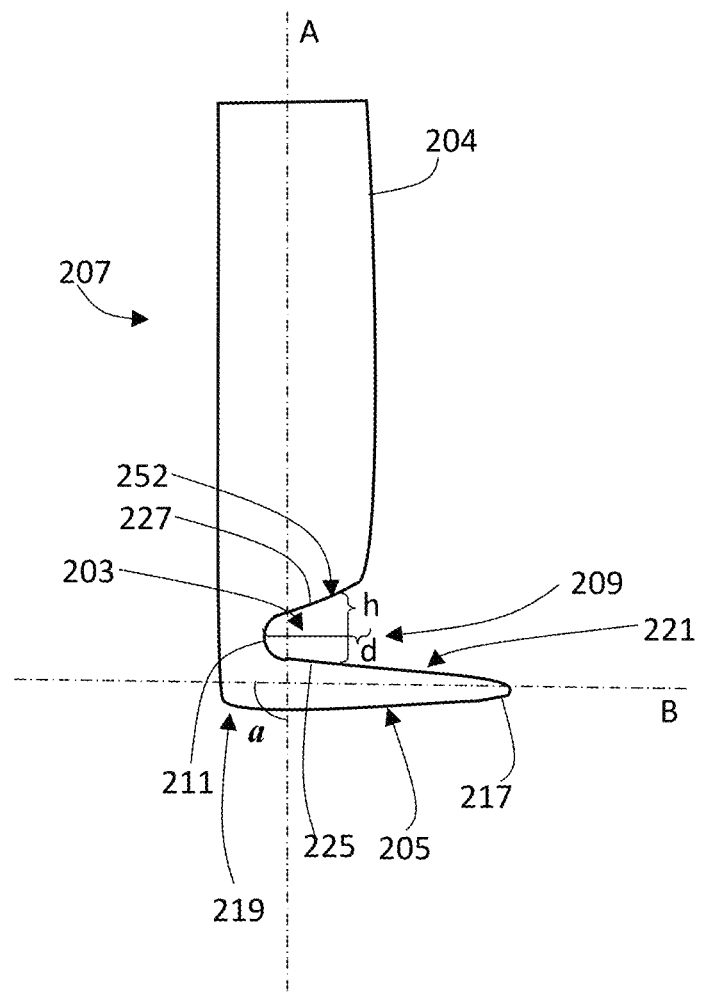
FIGS. 4A-4G show variations of a tissue grabber.

In some variations, as shown in FIG. 4A, the tissue grabbing region 203 may be a partially enclosed region of space bounded by one or more tissue grabbing surfaces and may comprise an opening 209 configured to receive tissue, such as trabecular meshwork, therethrough. The tissue grabbing region 203 may be bounded by an upper tissue grabbing surface 227 and a lower tissue grabbing surface 225 that connect at a closed back 211. The tissue grabbing region 203 may comprise a groove, mouth, crevice, cavity, indentation, gap, open space, or notch configured to receive, grip, trap and/or collect tissue therein. The tissue grabbing region 203 may provide an opening where tissue (such as a trabecular meshwork) may be inserted for pulling and removal through tearing, stripping, ripping, and/or avulsion. In this manner, the tissue grabber 207 may be configured to receive, trap, hold, or otherwise maintain a portion of tissue (e.g., trabecular meshwork) within or on the tissue grabbing region 203. When used in a trabeculectomy, the upper tissue grabbing surface 227 may be configured to be positioned above the trabecular meshwork and the lower tissue grabbing surface 225 may be configured to be positioned in Schlemm's canal and thus below the trabecular meshwork.

In some variations, the lower grabbing surface 225 may be coextensive with a portion of the upper or the dorsal surface 221 of the guide foot 205. In some variations, the upper grabbing surface 227 may be coextensive with an indented surface 252 of the proximal portion 204 of the tissue grabber 207, as shown in FIGS. 2A, 4A-4F, and 7A-7E. In other variations shown and described herein below, the upper grabbing surface may be coextensive with an un-indented surface of the proximal portion (for example as shown in FIGS. 9A-9J) or a plantar surface of an upper foot located above guide foot 205 (for example as shown in FIGS. 12A-12B, 13, and 14A-14E).

The tissue grabber 207 may be configured so that, as guide foot 205 is advanced through Schlemm's canal, at least a portion of the trabecular meshwork gets fed through opening 209 into tissue grabbing region 203. In certain variations, the tissue grabbing region 203 may comprise a first side and a second side, wherein the first and second sides are open, so that an initially intact trabecular meshwork may be fed into the tissue grabbing region. The diameter of Schlemm's canal in an adult human is typically about 50 microns to 250 microns. It may be advantageous for the respective widths of the upper and lower grabbing surfaces 225, 227 be selected to ensure that, during use of the tissue manipulation and/or tearing device 200, the lower grabbing surface 225 of the tissue grabbing region 203 is placed inside Schlemm's canal and thus under the trabecular meshwork, while the upper grabbing surface 227 does not enter Schlemm's canal and remains over the trabecular meshwork. In some variations, the width of the lower grabbing surface 225 may be about or less than the diameter of Schlemm's canal, and the width of the upper grabbing surface 227 may be about to less than the width of the trabecular meshwork. In some variations, the upper grabbing surface 227 may be wider than the lower grabbing surface 225.

In certain variations, the ratio between the width of the upper grabbing surface 227 and the lower grabbing surface 225 may be between 1.2:1 and 5:1, including all values and sub-ranges therebetween. For example, the ratio between the width of the upper grabbing surface 227 and the lower grabbing surface 225 may be between 1.2:1 and 2:1, about 1.2:1, about 1.3:1, about 1.4:1, about 1.5:1, about 1.6:1, about 1.7:1, about 1.8:1, about 1.9:1, about 2:1, about 2.2:1, about 2.4:1, about 2.6:1, about 2.8:1, about 3:1, about 3.5:1, about 4:1, about 4.5:1, or about 5:1.

As noted herein, the lower grabbing surface 225 may be coextensive with a portion of the upper or dorsal surface 221 of the guide foot 205, in which case the width of lower grabbing surface may be determined by the width of guide foot 205, and the guide foot may be configured to fit inside Schlemm's canal. For example, in some variations, the width of the lower grabbing surface 225 and/or the guide foot 205 is between 50 microns and 300 microns, or any range or value therebetween, between about 50 microns and about 250 microns, between about 100 and about 130 microns, between about 200 and about 250 microns, about 100 microns, about 120 microns, about 140 microns, about 160 microns, about 180 microns, about 190 microns, about 200 microns, about 210 microns, or about 220 microns.

In some variations, the width of the upper grabbing surface 227 may exceed the diameter of Schlemm's canal and/or to be sufficiently wide to press on a scleral spur, the trabecular meshwork, and Schwalbe's line of the eye during use. The width of upper grabbing surface 227 may be determined by the width of proximal portion 204, or upper foot 251 as described herein below. The width of upper grabbing surface 227 may be between 200 microns and 1000 microns, or any range or value therebetween, between 600 microns and 1000 microns, between 500 and 900 microns, between 400 microns and 800 microns, between 200 microns and 400 microns, between 250 microns 600 microns, about 200 microns, about 250 microns, about 300 microns, about 350 microns, about 400 microns, about 500 microns, about 600 microns, about 700 microns, about 800 microns or and about 900 microns.

The tissue grabbing region 203 may have a depth d configured to provide sufficient volume for the torn and/or stuck trabecular tissue to be collected therein. A depth d of the tissue grabbing region 203 may be determined by a distance between the closed back 211 and the front opening 209. The depth of the tissue grabbing region 203 may be between about 50 microns and about 400 microns, including all values and sub-ranges therebetween. For example, the depth of the tissue grabbing region 203 may be about 50 microns, about 75 microns, about 100 microns, about 125 microns, about 150 microns, about 175 microns, about 200 microns, about 225 microns, about 250 microns, about 275 microns, about 300 microns, about 325 microns, about 350 microns, about 375 microns, or about 400 microns.

Figure 6A:
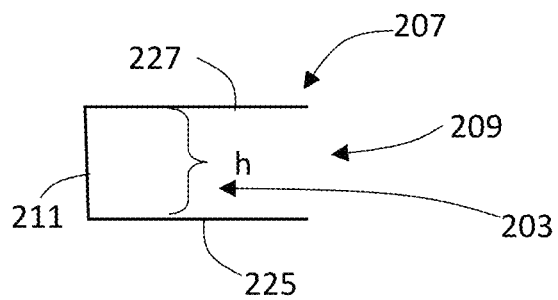
FIGS. 6A-6D show cross-sectional views of variations of a tissue grabbing region having a front opening and bounded by an upper grabbing surface, a lower grabbing surface, and a closed back.
Figure 6B:
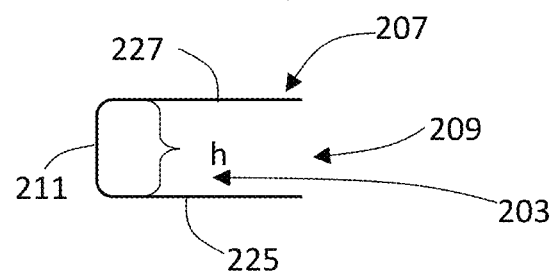

The tissue grabbing region 203 may have a height h that is sufficient to allow entry of tissue therein, and in some variations, to grip, trap, or otherwise contain tissue therein. The height h may be determined based on a distance between the upper grabbing surface 227 and the lower grabbing surface 225. In some variations, the height h may be measured along a line parallel to the longitudinal axis A (shown by way of example in FIG. 4A). In some variations, the height may be measured along a line (height line $L_h$) that is perpendicular to a line (bisecting line $L_b$) bisecting the angle f between the upper and lower grabbing surfaces (shown by way of example in FIG. 6C). The height h may be constant or variable. In some variations, the upper grabbing surface 227 and the lower grabbing surface 225 may be oriented to be about parallel to one another, and the height h of tissue grabbing region 203 may be constant (see FIGS. 6A-6B). In other variations, the upper surface 227 and the lower grabbing surface 225 may be oriented at an angle f relative to one another, and the height h of tissue grabbing region 203 may be variable (see FIGS. 6C-6D). In these variations, the height h of the tissue grabbing region 203 may vary along a central longitudinal axis of the guide foot B. For example, as shown in FIG. 4A, the height h of the tissue grabbing region 203 may decrease along the longitudinal axis B from a tip of the guide foot toward the shaft. In these variations. the tissue grabbing region 203 may have a maximum height at the front opening 209, a minimum height at the closed back 211 and the height h may decrease from the front opening 209 towards the closed back 211. The height h may decrease gradually, as depicted in FIG. 4A, or it may decrease in a stepwise fashion (not shown). The open front 209 may have a height configured to allow tissue, such as the trabecular meshwork, to enter the tissue grabbing region with relative ease. For example, in certain variations, the open front 209 may have a height of between about 100 microns and about 70 microns, including all values and sub-ranges therein. In some instances, the open front 209 may have a height of about 90 microns, about 80 microns, or about 70 microns. The closed back 211, may be shaped not as a sharp corner, but rather as a rounded or otherwise atraumatic surface. In some variations, the closed back 211 may have a rounded surface with a radius of curvature being no less than about 10 microns, no less than about 15 microns, or no less than 20 microns. The closed back 211 may have a minimum height that is less than the height at the open front, and small enough to grab and hold tissue, but is nevertheless sufficiently large to prevent the tissue from being pinch-cut by the closed back 211. In some variations, the closed back 211 may have a minimum height between about 20 microns and about 40 microns, including all values and sub-ranges therein. In some instances, the height h of the tissue grabbing region 203 at closed back 211 may be about 20 microns, about 30 microns, or about 40 microns. In some instances, the height h of the tissue grabbing region 203 at closed back 211 may be the height of between about 3 to about 6 blood cells, or about 4 blood cells. The ratio between the maximum height at the front opening and the minimum height at the closed back may be between about 5:1 and about 1.75:1, including all ratios and subranges therein. For example, in some variations, the ratio between the maximum height at front opening and the minimum height at the closed back may be about 5:1, about 4:1, about 3:1, about 2:1, or about 1.75:1. In some variations, the minimum height at the closed back may be between about 70% and about 10%, or any value or subrange therebetween, of the maximum height at the front opening. In some variations, the minimum height at the closed back may be between about 70% and about 10%, between about 60% and about 30%, between about 60% and about 40%, about 20%, about 30%, about 40%, about 50%, about 60% or about 70% of the maximum height at the front opening.

Figure 6C:
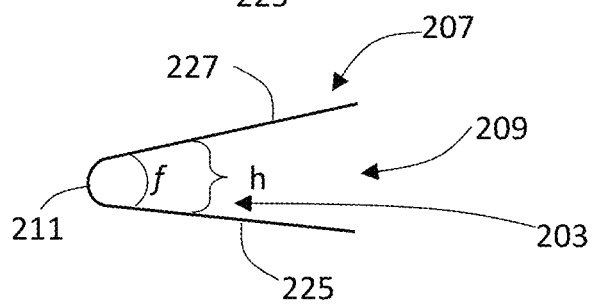
Figure 6D:
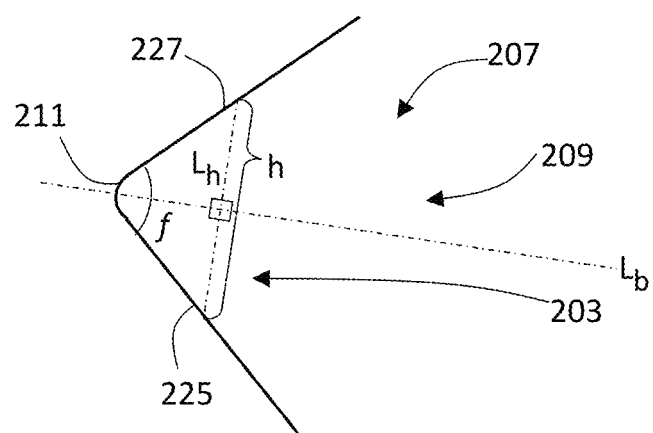

The degree of variability of the height h of the tissue grabbing region may be based on an angle of orientation f between the upper grabbing surface 227 and the lower grabbing surface 225. By way of example, the tissue grabbing region 203 as shown in FIG. 6C has an angle of orientation f of about 30 degrees, and the tissue grabbing region 203 as shown in FIG. 6D has an angle of orientation f of about 90 degrees. In some variations, the angle of orientation f between the upper grabbing surface 227 and the lower grabbing surface 225 may be between about 5 degrees and about 140 degrees, including all value and sub-ranges therein. For example, the angle between the upper grabbing surface 227 and the lower grabbing surface 225 may be between about 5 degrees and about 45 degrees, between about 10 degrees and about 30 degrees, less than about 90 degrees, less than about 45 degrees, between about 60 degrees and about 90 degrees, between about 60 degrees and about 140 degrees, about 20 degrees, about 30 degrees, about 40 degrees, about 50 degrees, about 60 degrees, about 70 degrees, about 80 degrees, about 90 degrees, about 100 degrees, about 120 degrees, or about 140 degrees.

Tissue Grabbing Mechanisms

The tissue grabber 207 may be configured to have tissue, (e.g., at least a portion of the trabecular meshwork) fed into or otherwise received in the tissue grabbing region 203. The tissue received in the tissue grabbing region 203 may then become stuck and collected therein, such that the tissue grabber 207 may be used to "grab" onto and manipulate tissue. The tissue grabber 207 (e.g., the tissue grabbing region 203) may be configured so that the tissue (e.g., trabecular meshwork) received in the tissue grabbing region 203 is not easily dislodged therefrom. The tissue grabber 207 may include one or more tissue grabbing mechanisms, as described below, that may work alone or in combination to achieve this result.

Variable Height of Tissue Grabbing Region

In some variations, the tissue grabbing region 203 may be configured to compress tissue that is directed therein. The compression of the tissue may be accomplished by having the height h of the tissue grabbing region be variable so that tissue grabbing region 203 narrows as the tissue grabber is advanced relative to the tissue (see for example FIGS. 6C-6D and 4A-4F). As the tissue grabber is advanced relative to the tissue, the height h of the tissue grabbing region 203 becomes less than the thickness of the tissue, thereby compressing the tissue. The tissue, due to being compressed by the narrowing tissue grabbing region 203 as the tissue is advanced towards closed back 211, may advantageously get stuck therein due to the compression. The trabecular meshwork in an adult human eye is typically between about 50 microns and 100 microns, and is a porous, compressible tissue. As such, by way of example where the trabecular meshwork enters a tissue grabbing region 203 having a height of about 80 microns at the front opening 209 and a height of about 30 microns at the closed back 211, the trabecular meshwork may become compressed and stuck within the tissue grabbing region 203 as the tissue approaches the closed back.

Tissue Collection Opening

The tissue grabber 207 may optionally comprise a tissue collection opening, which may be configured to receive a portion of tissue compressed into tissue grabbing region 203 and get the tissue further stuck within the tissue grabbing region 203. The tissue collection opening may be positioned on any of, including all, of the surfaces of the tissue grabbing region 203, the upper grabbing surface 227, the lower grabbing surface 225, and the closed back 211. The tissue collection opening may take a variety of forms, including, for example, an indention or a window. In some variations, the tissue grabber 207 may comprise a plurality (e.g., two, three, four, five or more) tissue collection openings positioned on various surfaces of the tissue grabbing region 203. Additionally or alternatively, the devices described herein may comprise a tissue collection opening positioned on another portion of the tissue grabber 207, such as, for example, the proximal portion, a portion of one or more feet outside the tissue grabbing region 203, and/or on the proximal portion 204 of the tissue grabber 207.

In some variations, the tissue collection opening may be an indentation formed on a portion of the surfaces of the tissue grabbing region 203, such as the upper grabbing surface 227, the lower grabbing surface 225, and/or the closed back 211. The indentation may be a closed indentation shaped as a blind ending cavity on one of the surfaces of the tissue grabbing region 203. Alternatively, an open indentation that has the same width as one of the surfaces of the tissue grabbing region 203 and effectively creates discontinuous increase in height h of the tissue grabbing region 203 at or near closed back 211. By way of example, FIG. 7A shows an embodiment of tissue grabber 207 comprising a tissue collection opening 231. The tissue collection opening 231 is shaped as an open indentation in the upper grabbing surface 227. With the tissue collection opening 231, the height h of the tissue grabbing region 203 initially decreases from the front opening 209 towards the closed back 211, and then increases again in the region most proximate or adjacent to the closed back 211. Thus, in some variations, the height h of the tissue grabbing region may still be variable but may decrease from the front opening 209 to a location between the front opening and the closed back 211, at which point it may again increase. In these variations, the tissue grabber and in particular, the tissue grabbing region may include a neck, or narrowed region 232. In some variations, the neck or narrowed region 232 may have the minimum height for the tissue grabbing region. The increased height provided by the tissue collection opening 231 may provide additional space within the tissue grabber for the tissue being directed therein to be collected and trapped, while the neck or narrowed region may still allow for effectively gripping tissue.

FIG. 7B shows another variation of a tissue grabber comprising a tissue collection opening. In this variation, the tissue grabber comprises two tissue collection openings 231, one in each of the upper grabbing surface 227 and the lower grabbing surface 225. Here, both of the tissue collection openings 231 are in the form of an indentation. Here, the height h of the tissue grabbing region also initially decreases from the front opening 209 towards the closed back 211, but due to the additional space provided by the tissue collection openings 231, the height h of the tissue grabbing region narrows at neck 232. However, past the neck 232 and proximate or adjacent to the closed back 211, the height h may be greater than the height h at the front opening 209. In other variations, the height may initially decrease from the front opening 209 towards the closed back 211, but may again increase such that the height h at the closed back 211 may be about equal to the height h at the front opening, or may remain less than the height h at the front opening but may be greater than the height h at the neck or narrowed portion. The indentation may provide an added height of between about 20 microns and about 100 microns at the closed back 211 compared to the height at the next. The indentation 231 may have, by way of example, a circular shape, an oval shape, a rectangular shape, or a square shape.

Figure 7C:
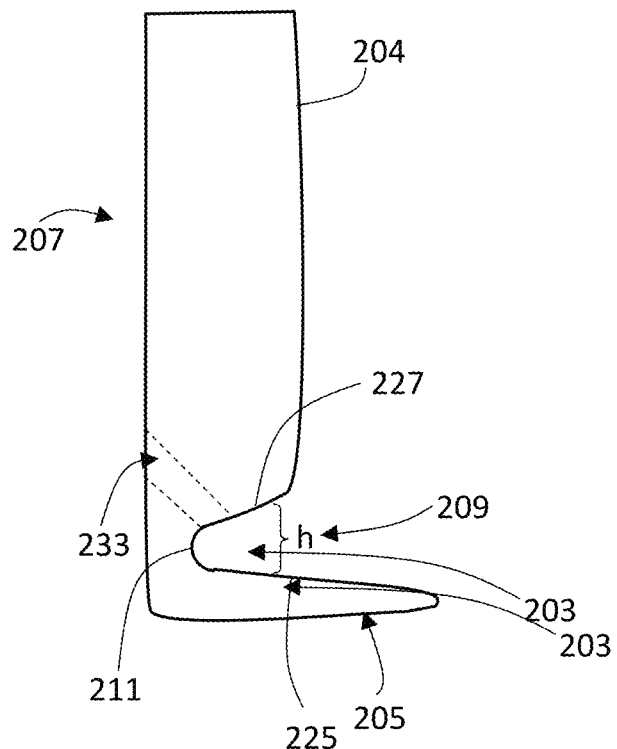
Figure 7D:
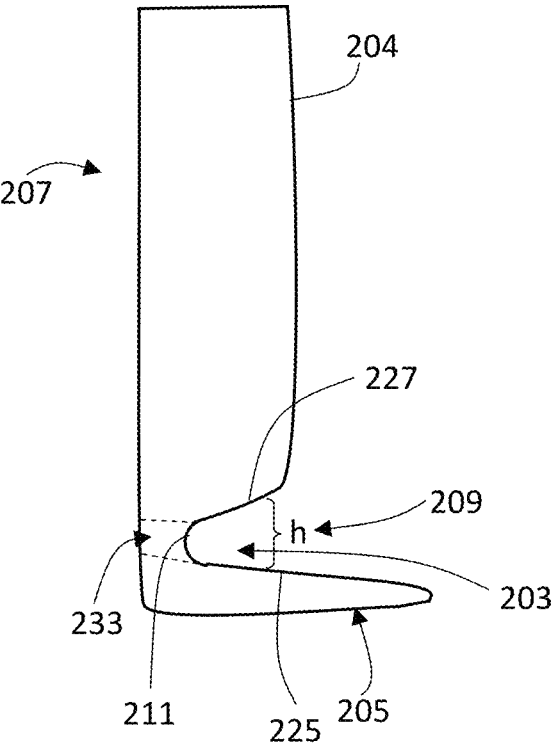
Figure 7E:
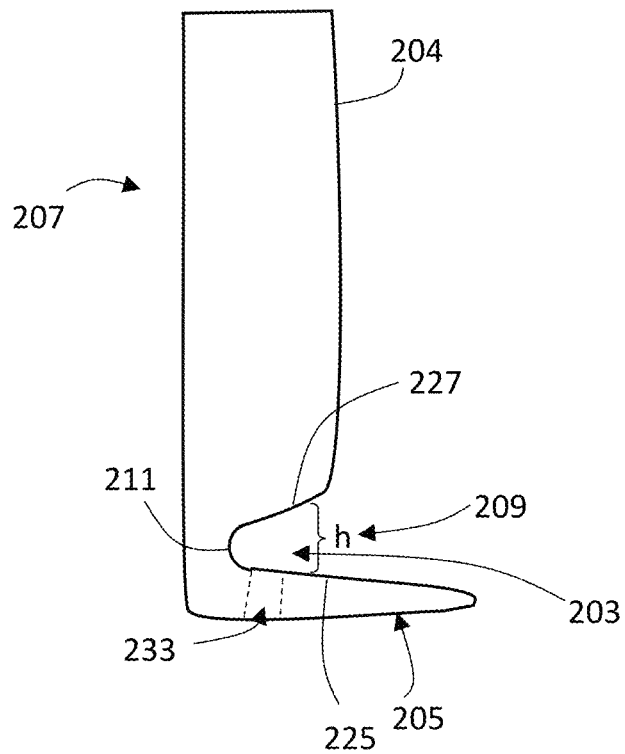

In some variations, the tissue collection opening may be a window or through hole formed within a portion of tissue grabber that opens into tissue grabbing region and traverses a portion of the tissue grabber 207. These windows provide additional space within the tissue grabber to collect and trap tissue. The windows may traverse any portion of the tissue grabber, such as, for example, the proximal portion, the closed back, the guide foot, and/or the upper foot. By way of example, FIGS. 7C-7E show variations of a tissue grabber 207 comprising a tissue collection opening 233 in the form of a window. In these variations, the windows create an opening in upper grabbing surface 227 and traverse a proximal portion of the tissue grabber (FIG. 7C), create an opening in the surface of the closed back 211 and traverse a portion of the tissue grabber adjacent to the closed back 211 (FIG. 7D), or create an opening in the lower grabbing surface 225 and traverse the guide foot 205 (FIG. 7E). In some variations, tissue grabber 207 may comprise a plurality of windows with openings at different sections within tissue grabber 207 and/or that traverse different sections of the tissue grabber 207 In some variations, the devices described herein may comprise a tissue collection opening in the form of a window through the shaft (e.g., at a distal portion of the shaft). In some variations, the surfaces of tissue grabbing region 203 may comprise one or more indentations as well as one or more windows in combination, as tissue collection openings.

Tissue collection openings in the form of windows may comprise an opening shaped as a square, a rectangle, a circle, an oval, or any other appropriate shape. The area of the opening of window may be between about 0.01 mm$^2$ and about 0.1 mm$^2$, about 0.01 mm$^2$, about 0.02 mm$^2$, about 0.03 mm$^2$, about 0.04 mm$^2$, about 0.05 mm$^2$, about 0.06 mm$^2$, about 0.07 mm$^2$, about 0.08 mm$^2$, about 0.09 mm$^2$, or about 0.1 mm$^2$.

Gripping Protrusions

In some variations, the tissue grabber may comprise one or more gripping protrusions on one or more surfaces of the tissue grabber to assist in grabbing, manipulating and/or tearing (by virtue of the ability to better hold the tissue received therein) tissue. The gripping protrusions may be formed on, coupled to, or otherwise located on a variety of surfaces on the tissue grabber, such as, for example, one or more of the upper grabbing surface, the lower grabbing surface, the closed back, the upper or the dorsal surface of the guide foot, and the lower or plantar surface of the upper foot. In some variations, the gripping protrusions may be formed on the dorsal surface of the guide foot, at or near the at a tip of the guide foot. In some variations, the devices described herein may additionally or alternatively comprise gripping protrusions on the shaft, such as, for example, on a distal portion of shaft (e.g., aligned with and proximal to the guide foot).

Figure 8A:
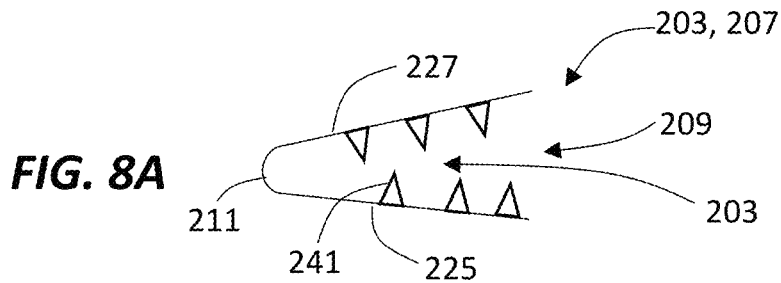
FIGS. 8A-8E depict cross-sectional views of a tissue grabbing region with different variations of gripping projections on the upper grabbing surface and the lower grabbing surface.
Figure 8B:
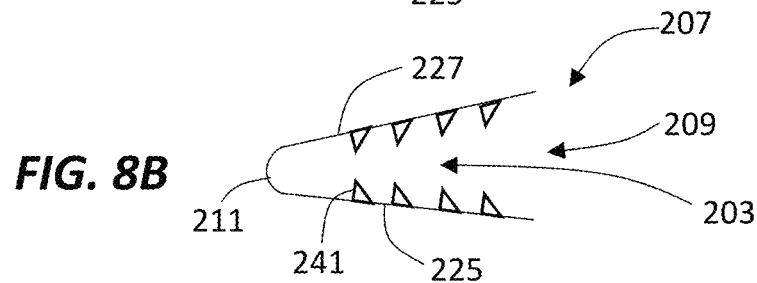
Figure 8C:
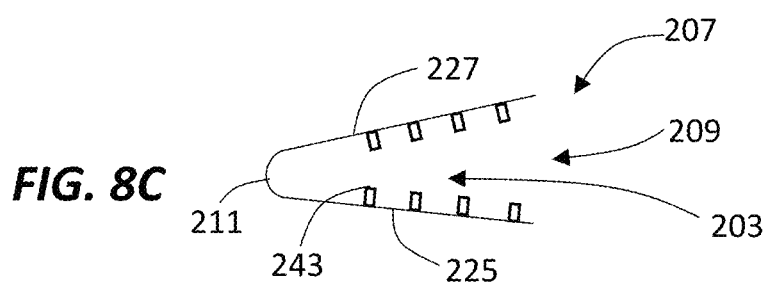
Figure 8D:
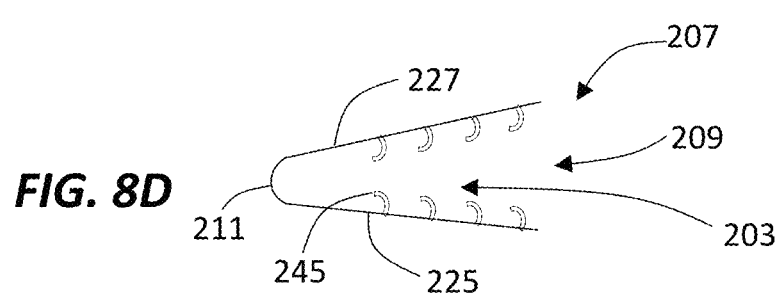

Reference is made to FIGS. 8A-8C, which show variations of a tissue grabber 207 comprising various types of gripping protrusions. In some variations, upper grabbing surface 227 and/or lower grabbing surface 225 may comprise gripping protrusions that function to improve the ability of tissue grabber 207 to grasp tissue (e.g., the trabecular meshwork) directed into the tissue grabbing region 203. The protrusions may be triangular protrusions or teeth 241 (FIGS. 8A-8B), which may be straight (FIG. 8A) or directed inwards towards the closed back 211, straight spikes 243 (FIG. 8C), or curved barbs 245 (FIG. 8D), in which the barbs are optionally directed inwards towards the closed back 211. The protrusions may be made on the surface by way of, for example, laser machining or EDM (electrical discharge machining). In some variations, the protrusions may have a length of between about 10 microns and about 90 microns, between about 10 microns and about 50 microns, about 10 microns, about 20 microns, about 30 microns, about 40 microns, about 50 microns, about 60 microns, about 70 microns, about 80 microns, or 90 microns.

Figure 8E:
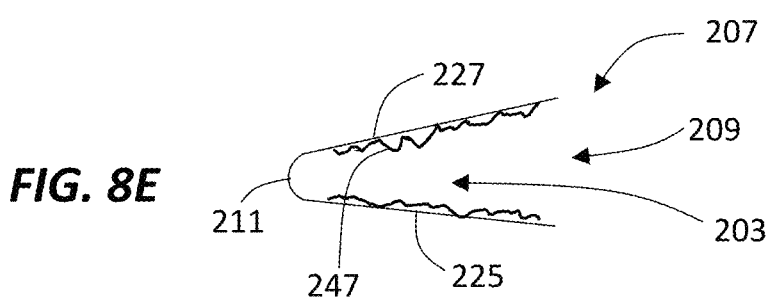
Figure 18A:
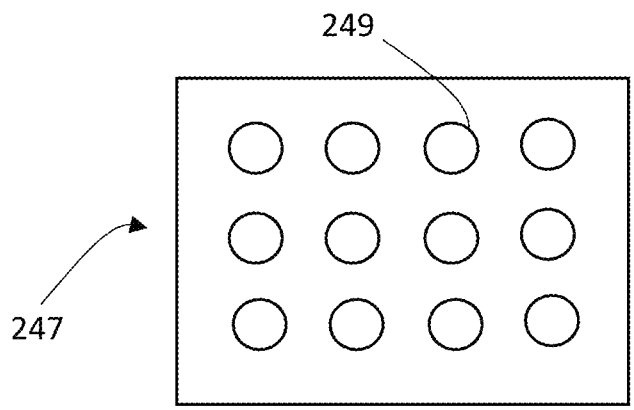
FIGS. 18A-18C show examples of roughened surfaces, each surface comprising a plurality of microcraters.
Figure 18B:
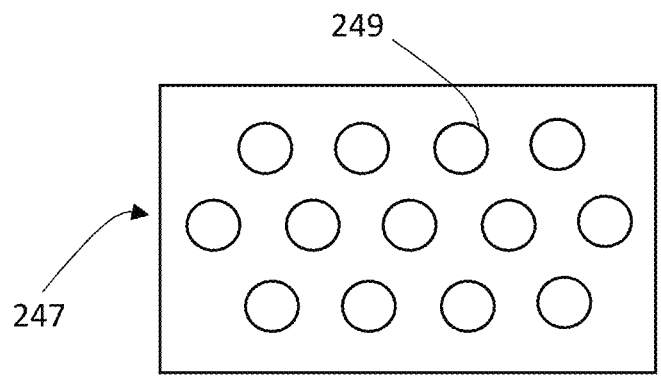
Figure 18C:
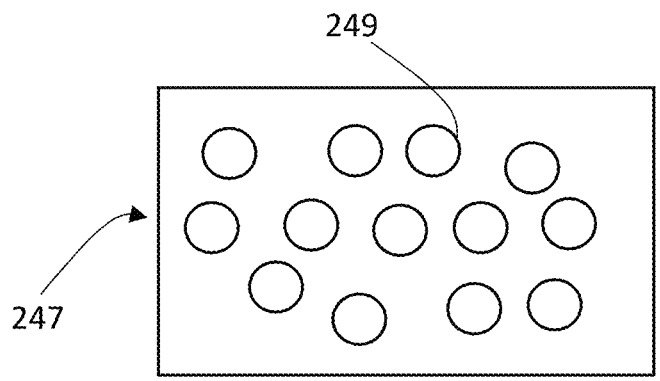

In some variations, the gripping protrusions may be in the form of a roughened surface and any portion of the tissue grabber, by way of example an upper or dorsal surface of a guide foot, a lower or plantar surface of a upper foot, or a surface of a tissue grabbing region such as an upper grabbing surface, a lower grabbing surface, or a closed back, may have a roughened surface. In some variations, as shown by way of example in FIG. 8E, the upper tissue grabbing surface 227, the lower tissue grabbing surface 225, the closed back 211, the upper or dorsal surface of the guide foot, and/or the lower or plantar surface of the upper foot may include a roughened surface 247. In some variations, as shown in by way of example in FIGS. 23A-23B a dorsal surface 1921 of a guide foot 1905, at or adjacent a tip 1917 of the guide foot may be a roughened surface. The roughened surface may be formed in a variety of ways. The surfaces of surgical instruments are typically electropolished to reduce friction imposed on surrounding tissue during a procedure, and in some variations, the roughened surface 247 may be prepared by way of refraining from electropolishing a desired portion of the tissue grabber, such as, for example, surfaces of the tissue grabbing region 203. By way of example, the surface of the guide foot 205 may be electropolished, with the exception of a portion of the upper or dorsal surface 221, such as, for example, a portion that is coextensive with lower grabbing surface 225. Through the lack of electropolishing, this portion of the surface is left with a comparatively higher coefficient of friction. In some variations, the material out of which tissue grabber 207 and components thereof are produced may be selected for having a relatively high degree of intrinsic roughness, so that the lack of polishing of the lower gripping surface, the upper gripping surface and/or the closed back results in a roughened surface with a desire degree of roughness. In some variations, the roughened surface may be prepared through application of a coating that applies granules such as diamond dust on the desired portions of the surface. In some variations, the roughened surface 247 may be prepared by creating small micron-scale indentations, which may be referred to herein as microcraters on desired portions of the surface. The microcraters may have any appropriate shape, such as a circular or irregular shape, and have an average diameter of between about 5 microns and about 75 microns, between about 10 microns and about 60 microns, between about 12 microns and about 50 microns, between about 20 microns and about 30 microns, about 15 microns, about 20 microns, about 25 microns, and about 30 microns. The microcraters may have other shapes, such as square, rectangular, hexagonal, or octagonal shapes. In some variations, the microcraters may be arranged on the surface in a regular pattern or an irregular pattern. The regular pattern may be a rectangular grid or a hexagonal grid. In some variations, the microcraters may be arranged on the surface with the distance between the respective centers of adjacent microcraters being between about 1.5× and about 4× of the microcrater diameter, between about 2× and about 3× of the microcrater diameter, about 1.5× of the microcrater diameter, about 2× of the microcrater diameter, about 2.5× of the microcrater diameter, or about 3× of the microcrater diameter. The microcraters may be created through, by way of example, targeted application of femtosecond laser pulses on the desired portions of the surface. The microcraters may have any suitable geometry and the geometry of the microcraters need not be uniform throughout the entire roughened surface. FIGS. 18A-18C show examples of roughened surfaces 247 comprising a plurality of microcraters 294. FIG. 18A shows a roughened surface comprising a plurality of microcraters arranged in a rectangular grid, FIG. 18B shows a roughened surface comprising a plurality of microcraters arranged in a hexagonal grid, and FIG. 18C shows a roughened surface comprising a plurality of microcraters arranged in an irregular pattern. While each of FIGS. 18A-C show microcraters having uniform size and shape throughout the roughened surface, they need not be, as those figures are merely for illustrative purposes. The roughened surface may provide a higher coefficient of friction with respect to tissue contacting the surface compared to other surfaces of tissue grabber 207. In some variations, the roughened surface may provide a static coefficient of friction of between about 0.4 and about 0.8 with respect to tissue contacting the roughened surface.

Reference is made to FIGS. 9A-9J, which show alternative configurations of a tissue grabber 267 in which the tissue grabbing region does not include a groove, mouth, gap, or other open space. In these variations, the upper grabbing surface 287 may be coextensive with a surface of the proximal portion 264 of the tissue grabber 267 and the lower grabbing surface 285 may be coextensive with a portion of the upper or dorsal surface of the guide foot 265. In the variations of tissue grabber 267 shown in FIGS. 9A-9G, the angle between upper the upper grabbing surface 287 and the lower grabbing surface 285 may be the same as or similar to the angle between the longitudinal axis A of the shaft (not shown) and the longitudinal axis B of the guide foot 265.

Figure 9A:
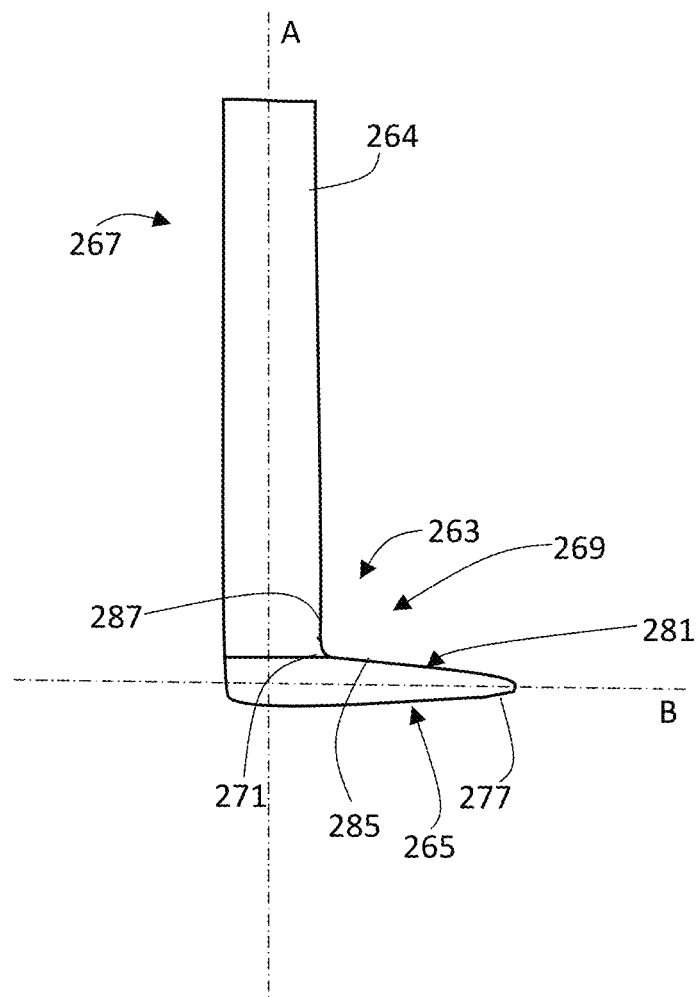
FIGS. 9A-9J show alternative variations of a tissue grabber in which the upper grabbing surface is perpendicular to the lower grabbing surface.
Figure 9B:
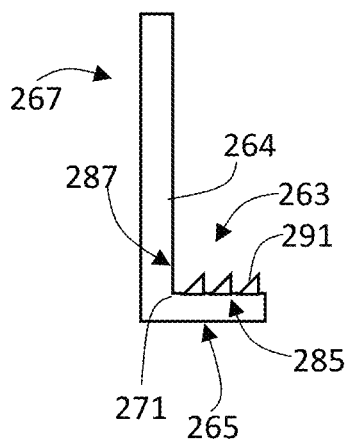
Figure 9C:
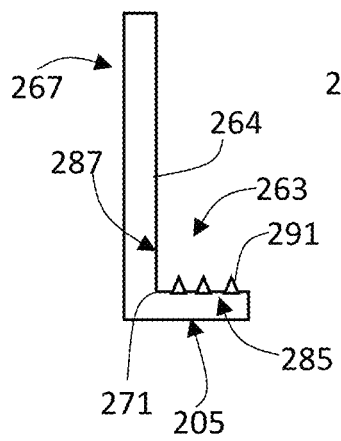
Figure 9D:
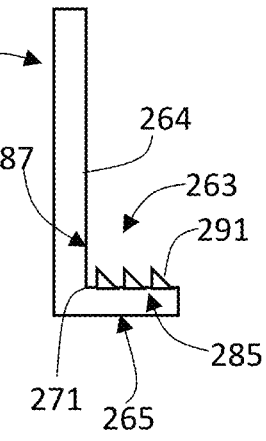
Figure 9E:
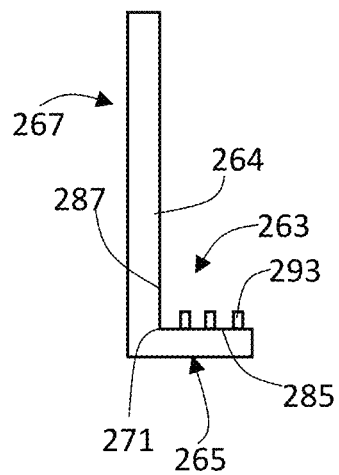
Figure 9F:
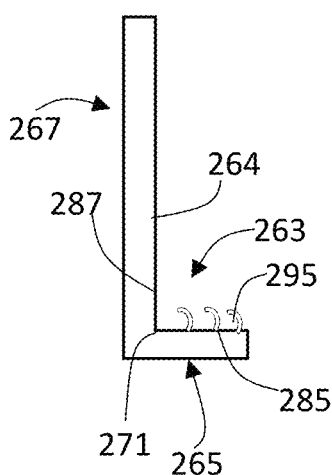
Figure 9G:
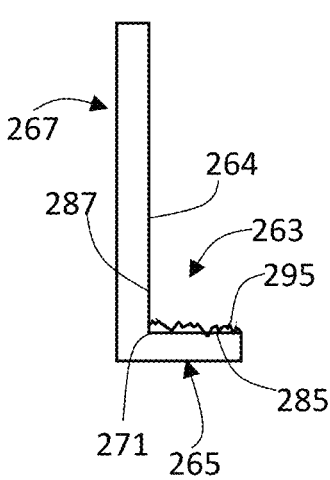

FIG. 9A depicts a variation of a tissue grabber 267 comprising a proximal portion 264 and a guide foot 265, in which an upper grabbing surface 287 is coextensive with a front surface 265 of proximal portion 264. A tissue grabbing region 263 with a closed back 271 may be formed between the upper grabbing surface 287 and a lower grabbing surface 285 that is coextensive with a dorsal surface 281 of the guide foot 265. The guide foot 265 may be configured, by way of example by having the tip 277 be tapered, to be able to be advanced atraumatically through Schlemm's canal. Tissue grabber 267 may comprise various means to collect or trap tissue that enters into tissue grabbing region 263, such as gripping protrusions (variations of which are shown by way of example in FIGS. 9B-9H), or one or more tissue collection openings (shown in for example in FIG. 19), which may be configured to receive a portion of tissue compressed into tissue grabbing region 263 and get the tissue further stuck within the tissue grabbing region.

FIGS. 9B-9H depict variations of gripping protrusions on tissue grabber 267 with the tissue grabbing region 263. In these variations, the upper grabbing surface 287 and/or lower grabbing surface 285 may comprise protrusions, by way of example triangular protrusions or teeth 291 (FIGS. 9B-9D), spikes 293 (FIG. 9E), or barbs 295 (FIG. 9F), similar to those described above with respect to FIGS. 8A-8D. In some variations, the gripping protrusions on the upper grabbing surface 287 and/or the lower grabbing surface 285 may be in the form of a roughened surface 297 (FIG. 9G), similar to that described above with respect to FIG. 8E. While the gripping protrusions in FIGS. 9B-9G are only depicted on the lower grabbing surface 285 (i.e., not upper grabbing surface 287), in other variations, the grasping protrusions may be located on the upper grabbing surface 287, or on both the upper grabbing surface and the lower grabbing surface.

Figure 9H:
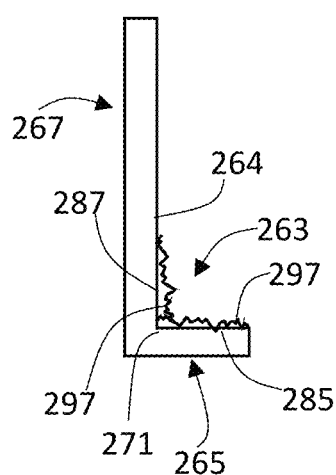
Figures 9I, 9J:
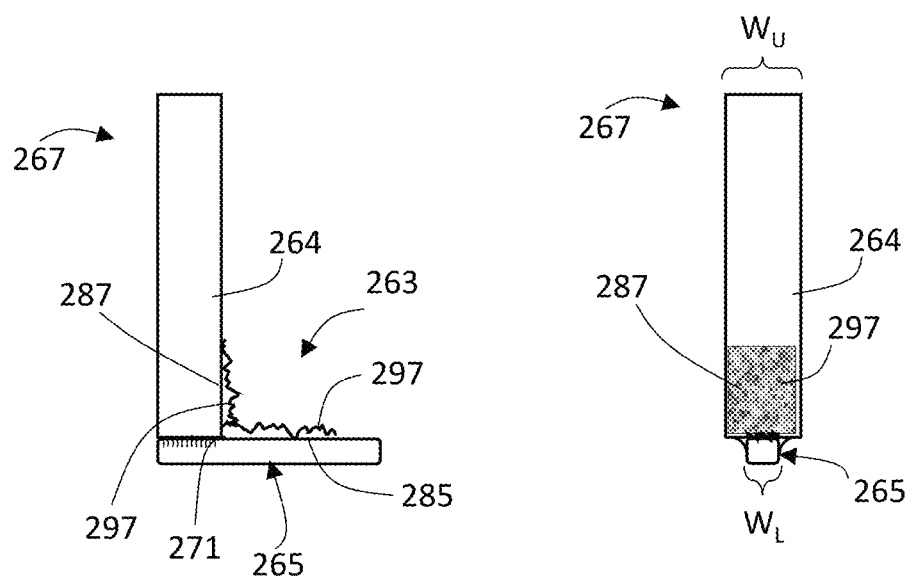

FIGS. 9H-9I show exemplary variations of the tissue grabber comprising gripping protrusions on both the lower and the upper grabbing surfaces. In this variation, the upper grabbing surface 287 of the tissue grabber 267 may comprise a roughened surface 297, and the roughened surface 297 and the upper grabbing surface 287 may be coextensive with a surface of proximal portion 264. The lower grabbing surface 285 may additionally comprise a roughened surface 297, which may be coextensive with the upper or dorsal surface of the guide foot 265. In some variations, a width Wu upper grabbing surface 287 may be wider than a width WL of the lower grabbing surface 285. As shown in FIG. 9J, which is a front view of the tissue grabber 267 shown in FIG. 9I, in a case where upper grabbing surface 287 is coextensive with a surface of the proximal portion 264 and the lower grabbing surface 285 is coextensive with a portion of the upper or dorsal surface of the guide foot 205, Wu may be the width of the proximal portion 264, and WL may be the width of the corresponding portion of guide foot 265.

Figure 19:
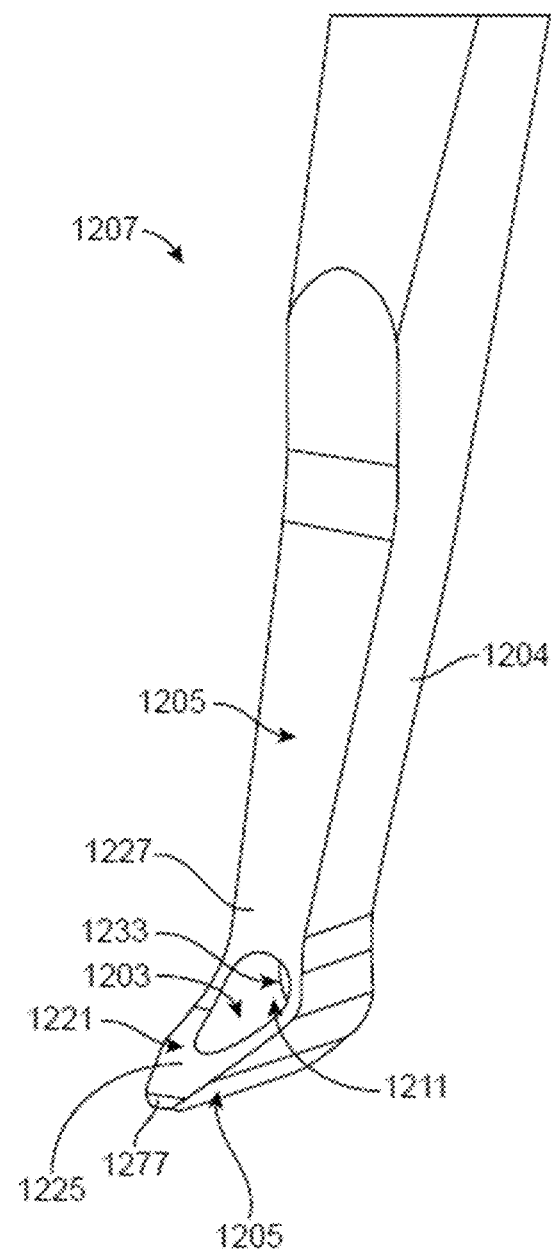
FIG. 19 shows an exemplary tissue grabber.

The tissue collection opening may be positioned on any of, including all, of the surfaces of the tissue grabbing region, the upper grabbing surface, the lower grabbing surface, and the closed back. The tissue collection opening may take a variety of forms, including, for example, an indention or a window. FIG. 19 shows a further variation of tissue grabber 1207. As with the variations shown in FIGS. 9A-9J, tissue grabber 1207 comprises a proximal portion 1204 and a guide foot 1205, in which an upper grabbing surface 1227 is coextensive with a front surface 1205 of proximal portion 1204 and a lower grabbing surface 1225 that is coextensive with a dorsal surface 1221 of the guide foot 1205. The tissue grabber 1207 may comprise a tissue grabbing region 1203 with a closed back 1211 formed between the upper grabbing surface 1227 and the lower grabbing surface 1225. The tissue grabber 1207 may comprise one or more tissue collection openings 1233. The tissue collection opening 1233 may be configured as a window that forms an opening in the surface of the closed back 1211 and continues as a through-hole traversing a portion of the proximal portion 1204 adjacent to the closed back 1211. As tissue is placed into tissue grabbing region 1203, some of the tissue may be pressed into the tissue collection opening 1233 to get the tissue further stuck within the tissue grabbing region 1203. A tapered shape of guide foot 1205 with an atraumatic, narrowed tip 1277 may help guide the tissue into tissue collection opening 1233.

Guide Foot

As mentioned above, the tissue grabber may comprise a guide foot configured to help guide the movement of the tissue manipulation and/or tearing device, as the device is moved relative to the surrounding tissue. The guide foot generally is shaped as an elongate structure that extends transversely to the longitudinal axis of the shaft and/or the proximal portion of the tissue grabber, and may comprise a heel at one end (which may be referred to as the back end), and a tip at the opposite end (which may be referred to as the front end). In some variations, the guide foot 205 and the proximal portion may be integral and be shaped or formed out of a common material. As shown in FIG. 4A, the guide foot 205 may be coupled to, or otherwise positioned at, the proximal portion 204 of tissue grabber 207 and may be configured to be inserted into Schlemm's canal. The guide foot 205 may comprise a heel 219 at one end, and a tip 217 at the opposite end. For example, the guide foot may be configured such that, when the guide foot 205 is inserted into the canal, the trabecular meshwork rests on or otherwise contacts the top or dorsal surface 221 of the guide foot 205.

The guide foot 205 may be configured, by way of example by having the tip 217 be tapered, to be able to be advanced atraumatically through Schlemm's canal.

The guide foot 205 may have an elongate structure and may extend relative to the proximal portion 204 of the tissue grabber 207 and/or the distal portion 202 of the shaft 201. For example, the guide foot 205 may have a central longitudinal axis B that is transverse to the longitudinal axis A of the proximal portion 204 of the tissue grabber 207 and/or the distal portion 202 (or entirety) of the shaft 201. The guide foot 205 may extend relative to the proximal portion 204 of the tissue grabber 207 and/or the distal portion 202 of the shaft at any angle suitable for entry into, and advancement through, a tissue passageway, such as, for example, Schlemm's canal. For example, a guide foot angle a formed between the central longitudinal axis B of the guide foot 205 and the longitudinal axis A of the proximal portion 204 of the tissue grabber and/or the distal portion 202 (or entirety) of the shaft 201 may be between about 80 degrees and about 140 degrees, including any values and sub-ranges therein. In some variations, the guide foot angle a may be between about 85 degrees and 95 degrees, about 80 and about 100 degrees, about 80 degrees and about 95 degrees, about 90 degrees and about 100 degrees, about 90 degrees and about 120 degrees, about 100 degrees and about 130 degrees, and about 120 degrees and about 140 degrees. For instance, in some variations, the guide foot angle may be about 82 degrees, about 85 degrees, about 87 degrees, about 90 degrees, about 92 degrees, about 95 degrees, about 97 degrees, about 100 degrees, about 102 degrees, about 105 degrees, about 107 degrees, about 110 degrees, about 112 degrees, about 115 degrees, about 117 degrees, about 120 degrees, about 122 degrees, about 125 degrees, about 127 degrees, about 130 degrees, about 132 degrees, or about 135 degrees.

The guide foot 205 may be sized so that it is appropriate for insertion into, and use within, an intraocular space. In variations where the guide foot 205 provides the lower grabbing surface 225, the guide foot is long enough and wide enough to provide a surface that is sufficiently large to grab tissue. When the tissue manipulation and/or tearing device 200 is used to perform a goniotomy, the length of guide foot 205 may be long enough to securely position the tissue grabbing region 203 at the trabecular meshwork when the guide foot is inserted into the canal, but not too long so as to obstruct access into the eye or to make the guide foot too fragile to risk breakage during use. The guide foot 205 may have a length that is sufficiently short to be able spin or rotate the device along the longitudinal axis A of the proximal portion 204 of the tissue grabber 207 and/or the distal portion 202 of the shaft 201 at least about 90 degrees, at least about 180 degrees, at least about 360 degrees, at least about 720 degrees, between about 5 degrees and about 180 degrees, or about 180 degrees within the anterior chamber of the eye without inadvertently striking intraocular tissue. By way of example, the length of the guide foot 205 may be between about 200 microns and 1000 microns, including all values and sub-ranges therein, as measured from the tip 217 of the guide foot to the closed back 211. For instance, the length of the guide foot 205 may be, between about 300 microns and about 1000 microns, between about 400 microns and about 1000 microns, between about 300 microns and about 800 microns, or between about 500 microns and about 800 microns. Optionally, the length of the guide foot 205 may be about 200 microns, about 300 microns, about 400 microns, about 500 microns, about 600 microns, about 700 microns, about 800 microns, about 900 microns, or about 1000 microns.

In variations where the guide foot 205 provides the lower grabbing surface 225, the width of the guide foot 205 may be determined to allow the guide foot to provide a sufficiently wide lower grabbing surface 225. In variations in which the devices described herein are used for trabeculotomies, and thus the guide foot 205 is inserted into Schlemm's canal, the guide foot may be sufficiently narrow to make the guide foot readily insertable inside Schlemm's canal. The width of the guide foot 205 may be configured so that the guide foot is not loose inside and deflect within the canal, but also not too wide so that the guide foot will not tear or causing undue trauma to the canal. Optionally, the cross-sectional width of the guide foot may be between 50 microns and 300 microns, or any sub-range or value therebetween, between 50 microns and 250 microns, between 100 and 130 microns, between 200 microns and 250 microns, about 100 microns, about 120 microns, about 140 microns, about 160 microns, about 180 microns, about 190 microns, about 200 microns, about 210 microns, or about 220 microns.

Figure 5A:
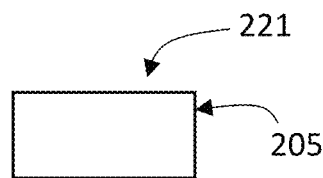
FIGS. 5A-5F depict cross-sectional views of variations of a guide foot of a tissue grabber.
Figure 5B:
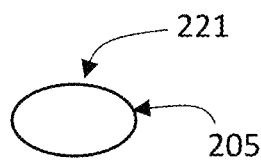
Figure 5C:
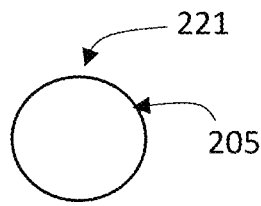
Figure 5D:
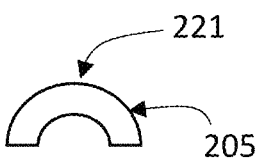
Figure 5E:
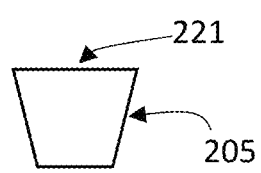
Figure 5F:
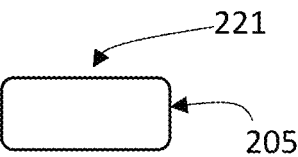

The cross-sectional shape of the guide foot 205 having a dorsal surface 221 may be any shape suitable for insertion into an intraocular space such as Schlemm's canal, and may be, by way of example, rectangular, oval, circular, arched, or trapezoidal, as shown in FIGS. 5A-5E. In some variations, one or more, or optionally all, corners present in the guide foot may be rounded or otherwise atraumatic to prevent inadvertent damage to, or cutting of, tissue. By way of example, FIG. 5F shows a rectangular cross-sectional shape for the guide foot 205 with all corners rounded. The radius of curvature of the rounded corners may be between about 1 micron and about 10 microns, between about 1 micron and about 5 microns, or between about 2 microns and about 4 microns, about 2 microns, about 4 microns, about 6 microns, about 8 microns, and about 10 microns.

The guide foot 205 may have a variable thickness or a constant thickness. For example, in some variations, the guide foot may have a first thickness at the tip 217 and a second, different thickness at the heel 219. In these variations, the first thickness may be less than the second thickness such that the guide foot 205 is thinner at the tip 217 than at the heel 219. In some variations, the thickness of the guide foot 205 may vary along a longitudinal axis B of the guide foot between the tip 217 and the heel 219. For example, the thickness may gradually change between the tip 217 and the heel 219 such that the guide foot 205 appears to be tapered (e.g., it has an angled top or dorsal surface). As another example, the guide foot 205 may comprise one or more steps or protrusions, which may increase the thickness along the longitudinal axis B of the guide foot from the tip 217 toward the heel 219, In some instances, utilizing a guide foot 205 with a narrower tip may assist a user in creating the initial puncture (goniopuncture) in the trabecular meshwork to enter Schlemm's canal, and may also serve to ease advancement of the guide foot through the canal once entered. In other variations, the guide foot 205 may have a constant thickness between the heel 219 and the tip 217. Put another way, the guide foot 205 need not have an angled top or dorsal surface.

In some variations, the tip 217 of the guide foot 205 may be rounded, as shown in FIG. 4A. The rounded tip 217 may have a radius of curvature between about 1 micron and about 10 microns, between about 1 micron and about 5 microns, or between about 2 microns and about 4 microns. In some variations, the radius of curvature of the rounded tip may be about 2 microns, about 4 microns, about 6 microns, about 8 microns, or about 10 microns. While, utilizing a guide foot 205 with a rounded tip may assist in preventing unintended trauma to ocular tissue, in some variations, the tip 217 of the guide foot 205 may not be rounded. For example, in some variations, the tip 217 of the guide foot 205 may comprise a sharpened tip. In some variations, the guide foot 205 may comprise angled lateral surfaces that intersect to form a sharpened tip. In these variations, the sharpened tip is intended to be used to assist in creating the initial puncture (goniopuncture) to enter the canal, not to cut tissue for performing a trabeculotomy. In some instances, the devices described herein may be entirely devoid of sharp edges or points, with the exception of a sharpened tip 217 (see, e.g., FIG. 4G.)

In certain variations, configuring the lower grabbing surface 225 to be coextensive with a portion of dorsal surface 221 of guide foot 205, and configuring guide foot 205 to have a smoothly tapered shape, may advantageously ease the process of directing a tissue (e.g. the trabecular meshwork) resting on dorsal surface 221 of guide foot 205 into front opening 209 of a groove-shaped tissue grabbing region 203.

The guide foot 205, and the surfaces thereof, may have a variety of configurations. In some variations, the upper or dorsal surface and the lower or plantar surface may be parallel to one another or may be angled relative to one another. For example, as described with respect to FIG. 4A, the upper or dorsal surface of the guide foot 205 may be angled along the longitudinal axis B of the guide foot while the bottom or plantar surface remains flat, thus forming a guide foot 205 with a tapered shape along the longitudinal axis B. In some variations, the lower or plantar surface may also be angled, and the angle of the bottom or plantar surface may be the same as or different from the angle of the upper or dorsal surface of the guide foot relative to the central longitudinal axis of the guide foot. For example, the upper or dorsal surface of the guide foot 205 may have a taper angle of between about 2 degrees and about 30 degrees or any value or subrange therebetween, about 5 degrees, about 10 degrees, about 15 degrees, about 20 degrees, about 25 degrees, or about 30 degrees. The bottom or plantar surface may have a taper angle of about between about 2 degrees and about 30 degrees or any value or subrange therebetween, about 5 degrees, about 10 degrees, about 15 degrees, about 20 degrees, about 25 degrees, or about 30 degrees. In some variations, such as the variation depicted in FIG. 4B, the upper or dorsal surface 221 of the guide foot 205 may be perpendicular or about perpendicular to longitudinal axis A of shaft 201 and the lower or plantar surface of the guide foot may be angled. In other variations, such as the variation depicted in FIG. 4C, the upper and lower surfaces of the guide foot may be parallel or about parallel to one another.

Figures 4B, 4C, 4D:
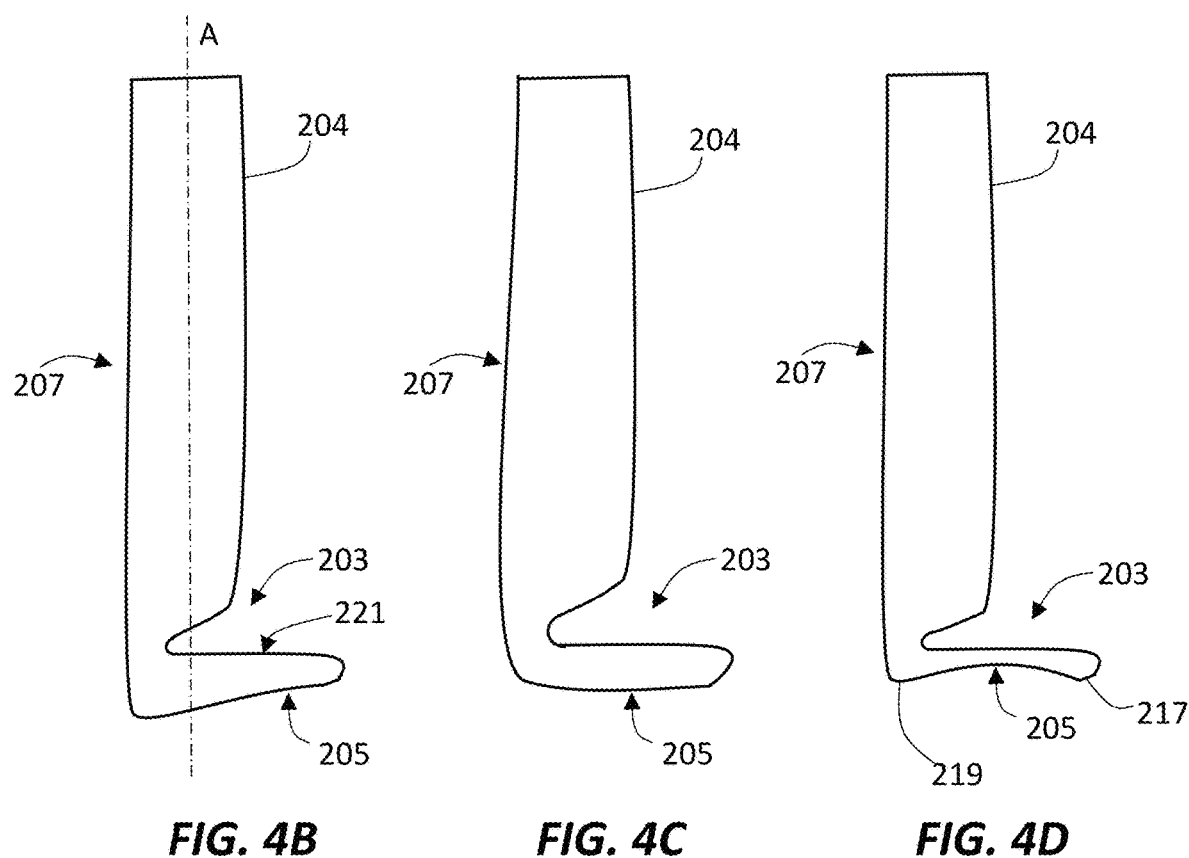

In some instances, one or more surfaces or a portion thereof of the guide foot 205 may have a curved configuration. For example, as depicted in FIG. 4D, in some variations, the lower or plantar surface may have a concave configuration and the upper or dorsal surface may have a linear configuration. In other variations, both the upper and the lower surfaces of the guide foot may have a concave configuration. In some variations, the lower surface of the guide foot may have a convex configuration. It should be appreciated that the upper and lower surfaces of the guide foot may have any configuration of curved and linear surfaces (e.g., both curved, both linear, bottom curved and top linear, top curved and bottom linear) allowing for entry into the intraocular space and atraumatic advancement of the guide foot within the eye (e.g., within Schlemm's canal).

Figures 4E, 4F:
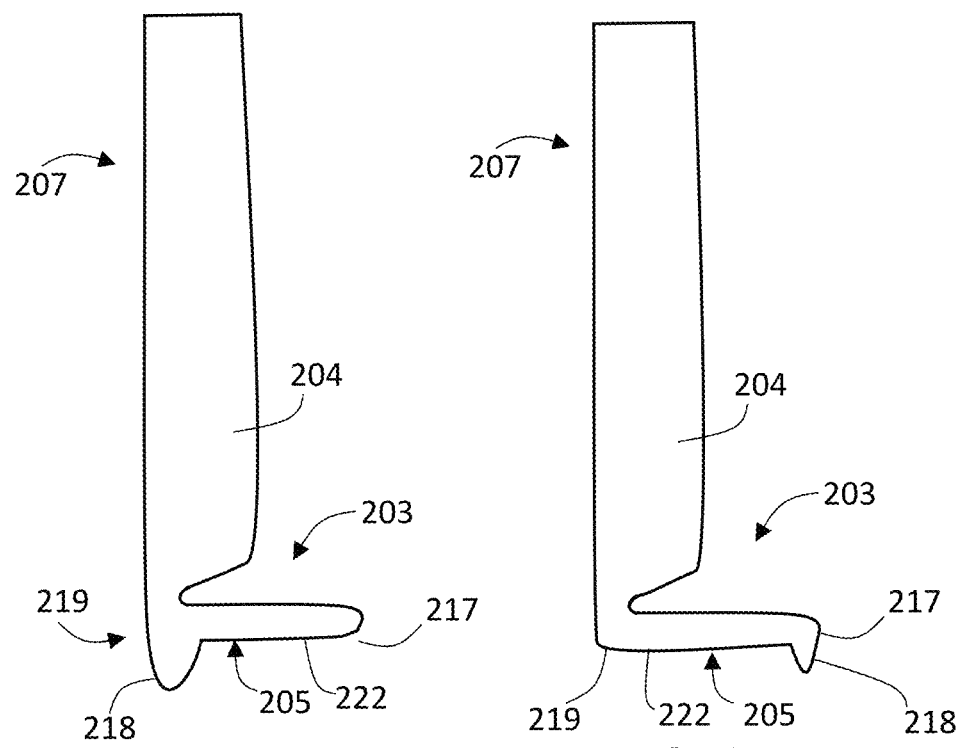
Figure 4G:
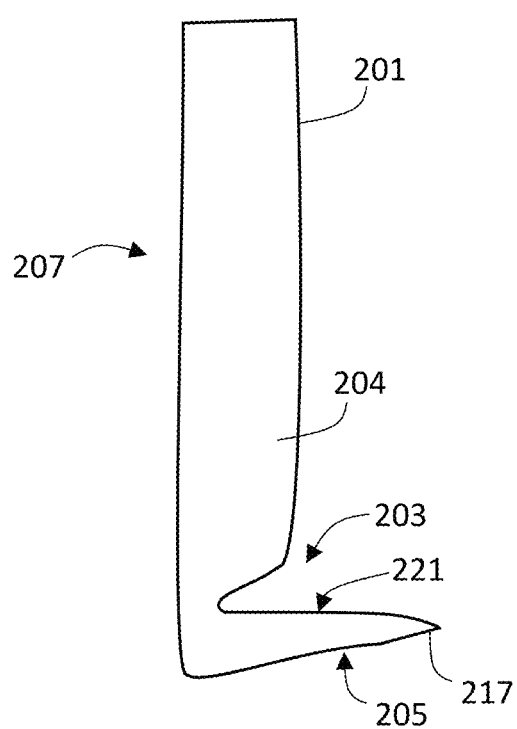

In some instances, the guide foot 205 may comprise on its plantar surface a structure to reduce friction between the plantar surface and tissue, for ease of advancing the tissue grabber 207 along tissue (by way of example a portion of Schlemm's canal). The friction-reducing structure may be a rounded protrusion 218. Reference is made to FIGS. 4E-4F. Guide foot 205 may comprise a rounded protrusion 218 on a plantar surface 222 of the guide foot. The rounded protrusion may be located, by way of example, at heel 219 (FIG. 4E), at tip 217 (FIG. 4F), or anywhere along the length of the guide foot 205. The rounded protrusion 218 may extend between about 5 microns and about 20 microns, between about 2 microns and 10 microns, about 2 microns, about 5 microns, about 10 microns, about 15 microns, or about 20 microns beyond the plantar surface 220 of the guide foot 205.

Upper Foot

In some variations, the tissue grabber may further comprise an upper foot configured to provide an upper grabbing surface. Similarly to the guide foot, the upper foot generally extends transversely to the longitudinal axis of the shaft and/or the proximal portion of the tissue grabber, and may comprise a tip at its end.

Figure 10:
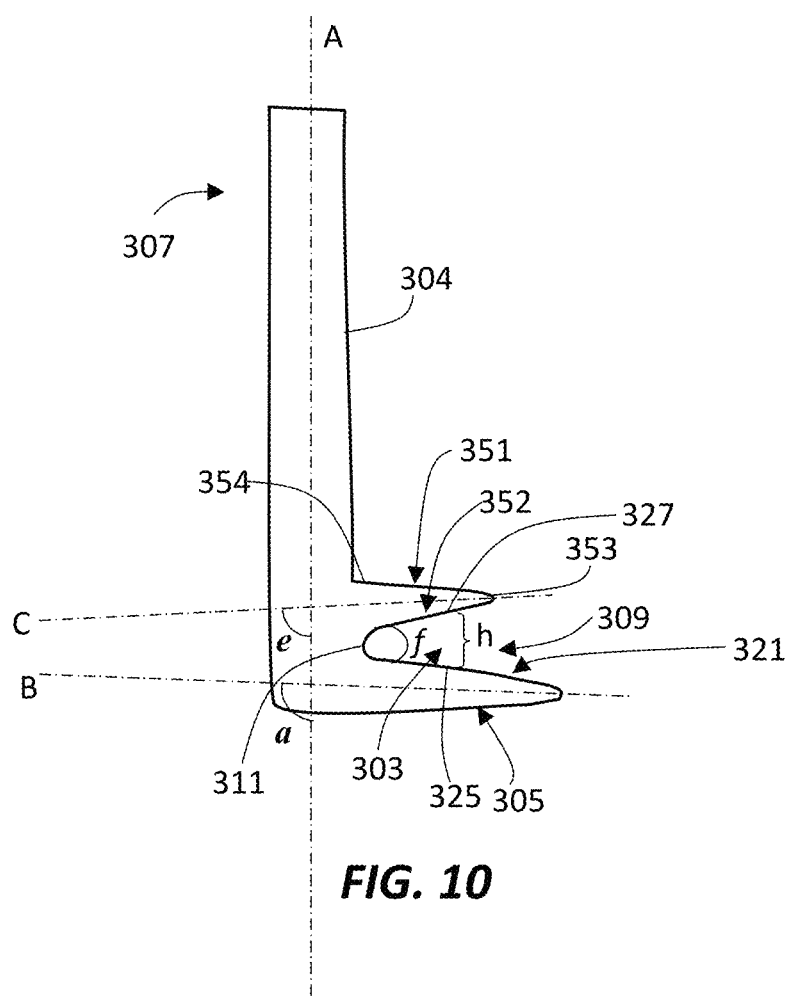
FIG. 10 schematically shows a tissue grabber in which a tissue grabbing region is located between an upper foot and a lower guide foot.

FIG. 10 shows a variation of a tissue grabber 307 that is similar to the tissue grabber 207 shown in FIG. 4A, with the exception that the tissue grabber 307 includes a second foot, an upper foot 351. The upper foot 351 may be positioned above, or proximal to the guide foot 305. In this variation, the tissue grabbing region 303 of the tissue grabber 307 is formed between the guide foot 205 and the upper foot 351. The tissue grabbing region 303 may provide an opening where tissue (such as a trabecular meshwork) may be inserted for pulling and removal through tearing, stripping, ripping, or avulsion. In this variation, the upper grabbing surface 327 of the tissue grabbing region 303 is coextensive with a lower or plantar surface 352 of the upper foot 351, and the lower grabbing surface 325 is coextensive with a portion of an upper or dorsal surface 321 of the guide foot 305. In some variations, the front opening 309 may be aligned with a tip 353 of the upper foot 351. The upper grabbing surface 327, with the exception of it being provided by the upper foot 351 and coextensive with the lower or plantar surface 352 of the upper foot, may have similar dimensions, orientations with respect to a lower grabbing surface, as well as additional features such as tissue collection openings and tissue grabbing mechanisms as the upper grabbing surface 227 as described above, by way of example with reference to any of FIGS. 2A, 4A-4G, 6A-6D, 7A-7E, and 8A-8E. The use of an upper foot 351 for providing the upper grabbing surface 327, as opposed to an indented portion of the proximal region 204 of the tissue grabber 207, may be advantageous in that a longer and/or wider upper grabbing surface may be provided, and that additional features such as the tissue collection opening or the tissue grabbing mechanisms could be added to the upper grabbing surface more easily, and/or without negatively affecting structural integrity of the tissue grabber. As such, it will be appreciated that all features that are described with respect to the upper grabbing surface 227 apply equally to the upper grabbing surface 327.

The upper foot 351 may be an elongate structure and may extend relative to the proximal portion 304 of the tissue grabber 307. For example, the upper foot 351 may have a central longitudinal axis C that is transverse to longitudinal axis A of proximate portion 304. The upper foot 351 may extend relative to the proximal portion 304 of the tissue grabber 307 and/or the shaft (not shown) at any angle suitable for advancement over a tissue, such as, for example, trabecular meshwork. An upper foot angle e formed between longitudinal axis C and longitudinal axis A may be between 80 degrees and 140 degrees, or any sub-range or value therein. Optionally the upper foot angle may be about 90 degrees, about 100 degrees, about 110 degrees, about 120 degrees, or about 135 degrees. In some variations, upper foot 351 and the proximal portion 304 may be integral and be shaped or formed out of a common material. This may be accomplished, for example, by laser machining, EDM (electrical discharge machining), etc. In some variations, upper foot 351 may be machined separately, then attached to proximal portion 304 through, by way of example, welding, soldering, bonding, riveting, etc.

Moreover, the upper foot 351 and the guide foot 305 may be positioned relative to one another to allow for the trapping of tissue, such as the trabecular meshwork, therebetween. In some variations, both the upper foot 351 and the guide foot 305 may extend directly from the proximal region 304 of the tissue grabber 307, as shown in FIG. 10. In other variations, the upper foot 351 may extend from the proximal region 304 of the tissue grabber 307 and the guide foot 305 may extend from the upper foot, optionally via a curved heel. In other variations, the guide foot 305 may extend from the proximal region 304 of tissue grabber 307 and the upper foot 351 may extend from the guide foot, optionally via a curved heel. In other variations, both the upper foot 351 and the guide foot 305 may extend from a common base that is connected to the proximal region 304 of the tissue grabber 307. In some variations, the longitudinal axis C of the upper foot 251 and the longitudinal axis B of the guide foot 205 may be within 20 degrees of each other, within 10 degrees of each other, within 5 degrees of each other, or about parallel to each other. Because, in some variations, the upper foot 351 provides the upper grabbing surface 327, and the guide foot 305 provides the lower grabbing surface, the orientation of the longitudinal axis C of the upper foot 251 with respect to the longitudinal axis B of the guide foot 205 contributes to the angle f between upper grabbing surface 327 and lower grabbing surface 325. In some variations where upper foot 351 or guide foot 305 are both not tapered, the angle f between upper grabbing surface 327 and lower grabbing surface 325 may be the same as the angle between the longitudinal axis C of the upper foot 351 and longitudinal axis B of the guide foot 205. However, in variations where one or both the upper foot 351 and the guide foot 305 are tapered, the angle f may be greater than the angle between the longitudinal axis C of the upper foot 251 and longitudinal axis B of guide foot 505. The length of upper foot 351 may be long enough to provide a sufficient upper grabbing surface 327 for tissue grabber 307. By way of example, the length of the upper foot 351 may be between about 50 microns and 500 microns as measured from the tip 353 of the upper foot to the closed back 311, including all values and sub-ranges therein. In some variations, the upper foot 351 may have a length between about 200 microns and about 500 microns, between about 100 microns and about 200 microns, between about 100 microns and about 300 microns, or between about 500 microns and about 800 microns. Optionally, the length of the upper foot 351 may be about 50 microns, about 60 microns, about 70 microns, about 80 microns, about 90 microns, about 100 microns, about 120 microns, about 140 microns, about 160 microns, about 180 microns, about 200 microns, about 250 microns, or about 300 microns.

Generally while in use, the tissue grabber 307 may be viewed by the user of the device from the proximal-to-distal direction, and it may be advantageous to have the tip 317 of guide foot 305 be visible and unobscured by the upper foot 351 so that a user can track the location of the device within the eye and more particularly, confirm the location of the guide foot 305 within Schlemm's canal. In some variations, the length of upper foot 351 may be configured to be less than the length of guide foot 305, which may allow a user to visualize the guide foot 205 when positioned within the canal without the upper foot 251 obscuring its view. The ratio between the length of guide foot 305 and the upper foot 351 may be between 3:1 and 1.2:1, including all ratio values and sub-ranges therein. For instance, in some variations, the ratio between the length of the guide foot 205 and the upper foot may be about 3:1, about 2.5:1, about 2:1, about 1.8:1, about 1.6:1, about 1.6:1, or about 1.2:1.

While the guide foot 305 may be configured for entry into Schlemm's canal, the upper foot 351 may be configured to remain outside of Schlemm's canal during use. For example, the width of upper foot 351 may be configured to prevent entry into Schlemm's canal. When in use, the desired positioning of the tissue grabber 307 is for the guide foot 305 to be within Schlemm's canal and for the upper foot 351 to be positioned above Schlemm's canal, while also touching and pressing on the trabecular meshwork. The upper foot may overlap Schwalbe's line and the scleral spur. As a result, a portion of the trabecular network is fed or otherwise received inside the tissue grabbing region 303. In certain variations, the tissue grabbing region 303 may comprise a first side and a second side, wherein the first and second sides are open, so that an initially intact trabecular meshwork may be fed into the tissue grabbing region. The tissue grabbing region 303 is delineated by the upper gripping surface 327 that is coextensive with the plantar surface 352 of the upper foot and by the lower gripping surface 325 that is coextensive with at least a portion of the dorsal surface 321 of the guide foot 305.

In some variations, the upper foot 351 may be wider than the guide foot 305. The difference in the respective widths allows for, by way of example, for the guide foot 305 to be inserted under the trabecular meshwork into Schlemm's canal, while upper foot 351 presses on and covers the trabecular network from above. As such, the difference in the respective widths of the two feet may improve the ease by which the tissue grabbing region 303 of tissue grabber 307 is correctly positioned with respect to the trabecular meshwork. The ratio between the width of the upper foot 351 and the width of the guide foot 305 may be between 1.2:1 and 5:1, including all values and sub-ranges therein, between 1.2:1 and 2:1, about 1.2:1, about 1.3:1, about 1.4:1, about 1.5:1, about 1.6:1, about 1.7:1, about 1.8:1, about 1.9:1, about 2:1, about 2.2:1, about 2.4:1, about 2.6:1, about 2.8:1, about 3:1, about 3.5:1, about 4:1, about 4.5:1, or about 5:1

Optionally, the plantar surface 352 of upper foot 351 may be configured to press on a scleral spur, the trabecular meshwork, and/or Schwalbe's line of the eye during use. The width of upper foot 351 may be between 200 microns and 1000 microns, or any range or value therebetween, between 600 microns and 1000 microns, between 500 and 900 microns, between 400 and 800 microns, about 300 microns, about 400 microns, about 500 microns, about 600 microns, about 700 microns, about 800 microns or and about 900 microns.

Figure 11A:
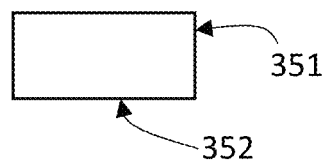
FIGS. 11A-11F depict cross-sectional views of variations of an upper foot of a tissue grabber.
Figure 11B:
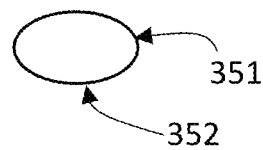
Figure 11C:
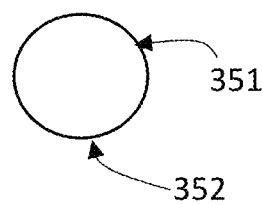
Figure 11D:
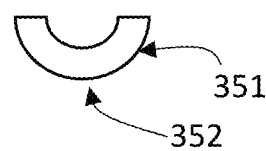
Figure 11E:
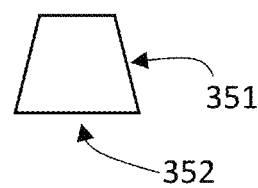
Figure 11F:
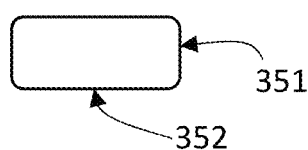

The cross-sectional shape of the upper foot 351 may be any suitable shape for insertion into an intraocular space, such as placement over the trabecular meshwork, and may be, by way of example, rectangular, oval, circular, arch, or trapezoidal, as shown in FIGS. 11A-11E. In some variations, one or more, or optionally all, corners present in the upper foot may be rounded to prevent inadvertent cutting of tissue. The radius of curvature of the rounded corners may be between about 1 micron and about 10 microns, between about 1 micron and about 5 microns, or between about 2 microns and about 4 microns, about 2 microns, about 4 microns, about 6 microns, about 8 microns, and about 10 microns. By way of example, FIG. 11F shows a rectangular cross-sectional shape for upper foot 351 with all corners rounded.

The upper foot 351 may have a variable or constant thickness. For example, in some variations, the upper foot may have a first thickness at the tip 352 and a second, different thickness at the base 354. In these variations, the first thickness may be less than the second thickness such that the upper foot 351 is thinner at the tip 353 than at the base 354. In some variations, the thickness of the upper foot 351 may vary along a longitudinal axis C of the upper foot between the tip 353 and the base 354. For example, the thickness may gradually change between the tip 353 and the base 354 such that the upper foot 351 appears to be tapered (e.g., it has an angled bottom or plantar surface). In other variations, the upper foot 351 may have a constant thickness between the base 354 and the tip 353. Put another way, the upper foot 351 need not have an angled bottom or plantar surface.

In some variations, the tip 353 of the upper foot 351 may be rounded, as shown in FIG. 10. The rounded tip 353 may have a radius of curvature between about 1 micron and about 10 microns, between about 1 micron and about 5 microns, or between about 2 microns and about 4 microns. In some variations, the radius of curvature of the rounded tip may be about 2 microns, about 4 microns, about 6 microns, about 8 microns, or about 10 microns. While, utilizing an upper foot 351 with a rounded tip may assist in preventing unintended trauma to ocular tissue, in some variations, the tip 353 of the upper foot 351 may not be rounded.

The upper foot 351, and the surfaces thereof, may have a variety of configurations. In some variations, the upper or dorsal surface and the lower or plantar surface may be parallel to one another or may be angled relative to one another. For example, as described with respect to FIG. 10, the upper or dorsal surface of the upper foot 351 may be angled along the longitudinal axis C of the upper foot while the bottom or plantar surface remains flat, thus forming the upper foot 351 with a tapered shape along the longitudinal axis C. In some variations, the lower or plantar surface may also be angled, and the angle of the bottom or plantar surface may be the same as or different from the angle of the upper or dorsal surface of the upper foot relative to the longitudinal axis of the upper foot. For example, the upper or dorsal surface of the upper foot 305 may have a taper angle of between about 2 degrees and about 30 degrees or any value or subrange therebetween, about 5 degrees, about 10 degrees, about 15 degrees, about 20 degrees, about 25 degrees, or about 30 degrees. The bottom or plantar surface may have a taper angle of about between about 2 degrees and about 30 degrees or any value or subrange therebetween, about 5 degrees, about 10 degrees, about 15 degrees, about 20 degrees, about 25 degrees, or about 30 degrees. In some variations the upper or dorsal surface 321 of the guide foot 305 may be perpendicular or about perpendicular to longitudinal axis A of proximal portion 304 and the lower or plantar surface of the guide foot may be angled. In other variations, such as the variation depicted in FIG. 4C, the upper and lower surfaces of the guide foot may be parallel or about parallel to one another.

In some instances, one or more surfaces or a portion thereof of upper foot 351 may have a curved configuration. For example, as depicted in FIG. 4D, in some variations, the lower or plantar surface may have a concave configuration and the upper or dorsal surface may have a linear configuration. In other variations, both the upper and the lower surfaces of the guide foot may have a concave configuration. In some variations, the lower surface of the guide foot may have a convex configuration. It should be appreciated that the upper and lower surfaces of the upper foot may have any configuration of curved and linear surfaces (e.g., both curved, both linear, bottom curved and top linear, top curved and bottom linear) allowing for entry into the intraocular space and atraumatic advancement of the guide foot within the eye (e.g., along the trabecular meshwork).

Figure 12A:
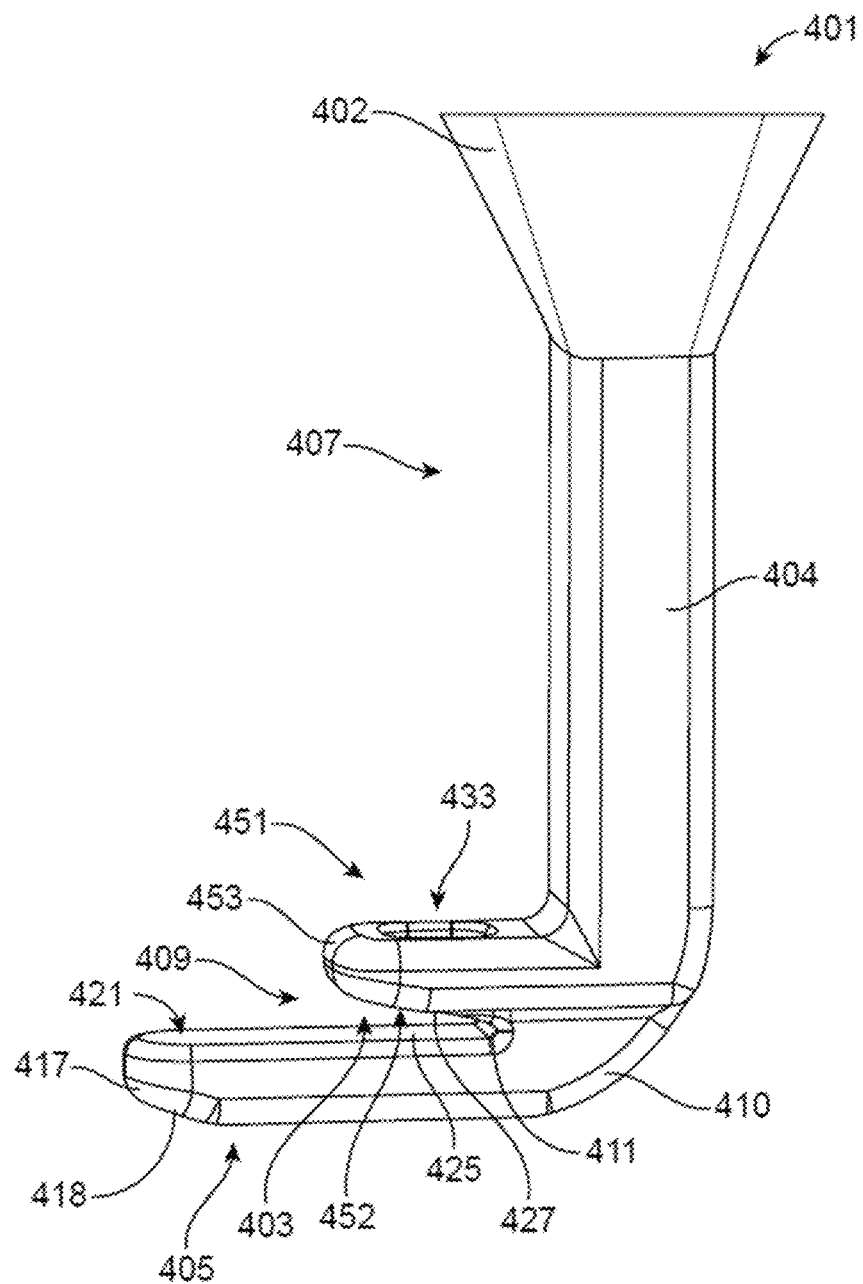
FIGS. 12A-12C show a side view and a front view, respectively, of a variation of a tissue grabber in which a tissue grabbing region is located between an upper foot and a lower guide foot.
Figure 12B:
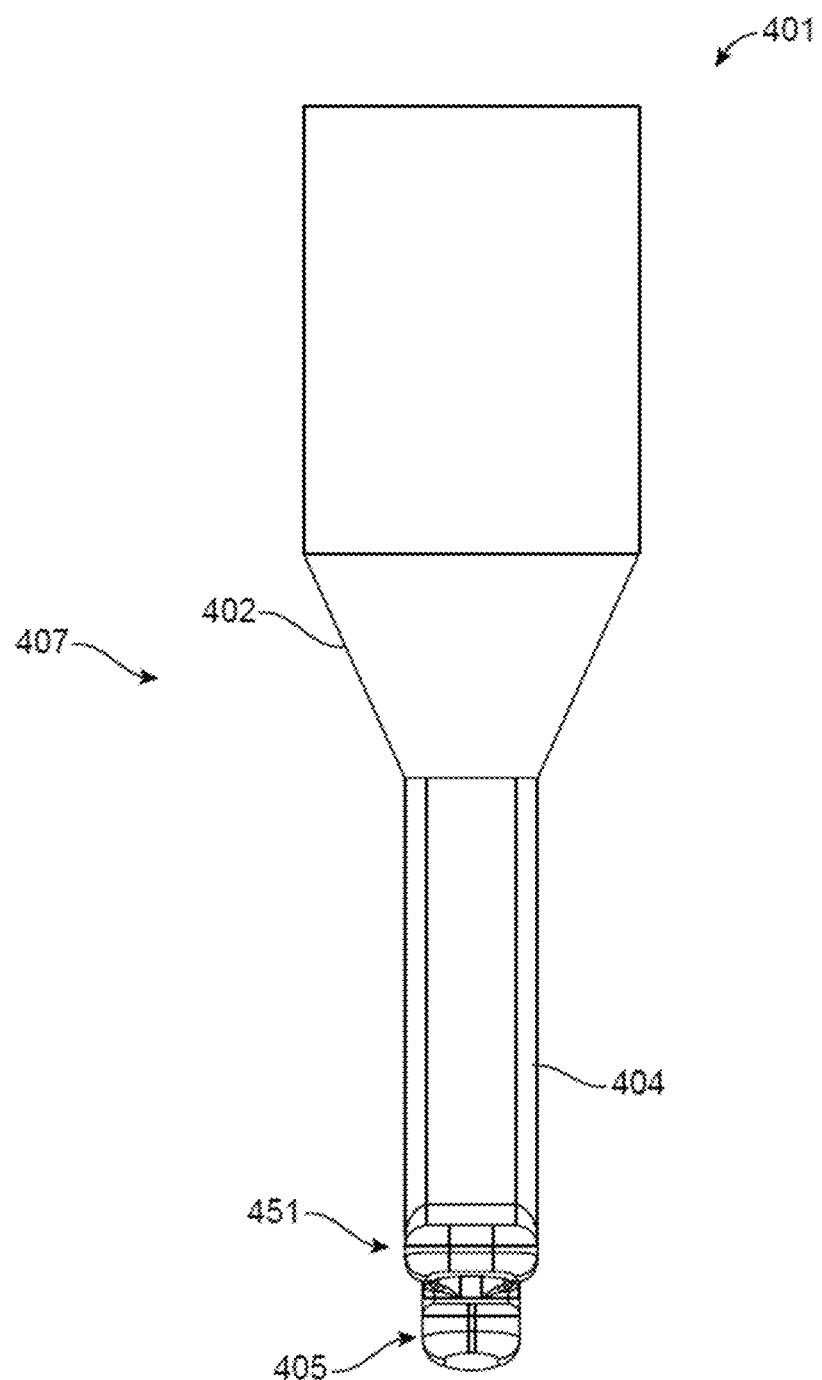

Reference is made to FIGS. 12A-12B, which show different views of an exemplary tissue grabber 407. FIG. 12A shows a side view of an exemplary tissue grabber 407. The tissue grabber may be coupled to or connectable to a distal end of a shaft, and comprises a proximal region 404, a guide foot 405, an upper foot 451, and a tissue grabbing region 403. In this variation, the guide foot 405 is longer than the upper foot 451. The plantar surface 452 of the upper foot 451 and the dorsal surface 421 of the guide foot 405 connect at the closed back 411, and form the tissue grabbing region 403 therebetween. The tissue grabbing region 403 comprises a front opening 409.

Figure 12C:
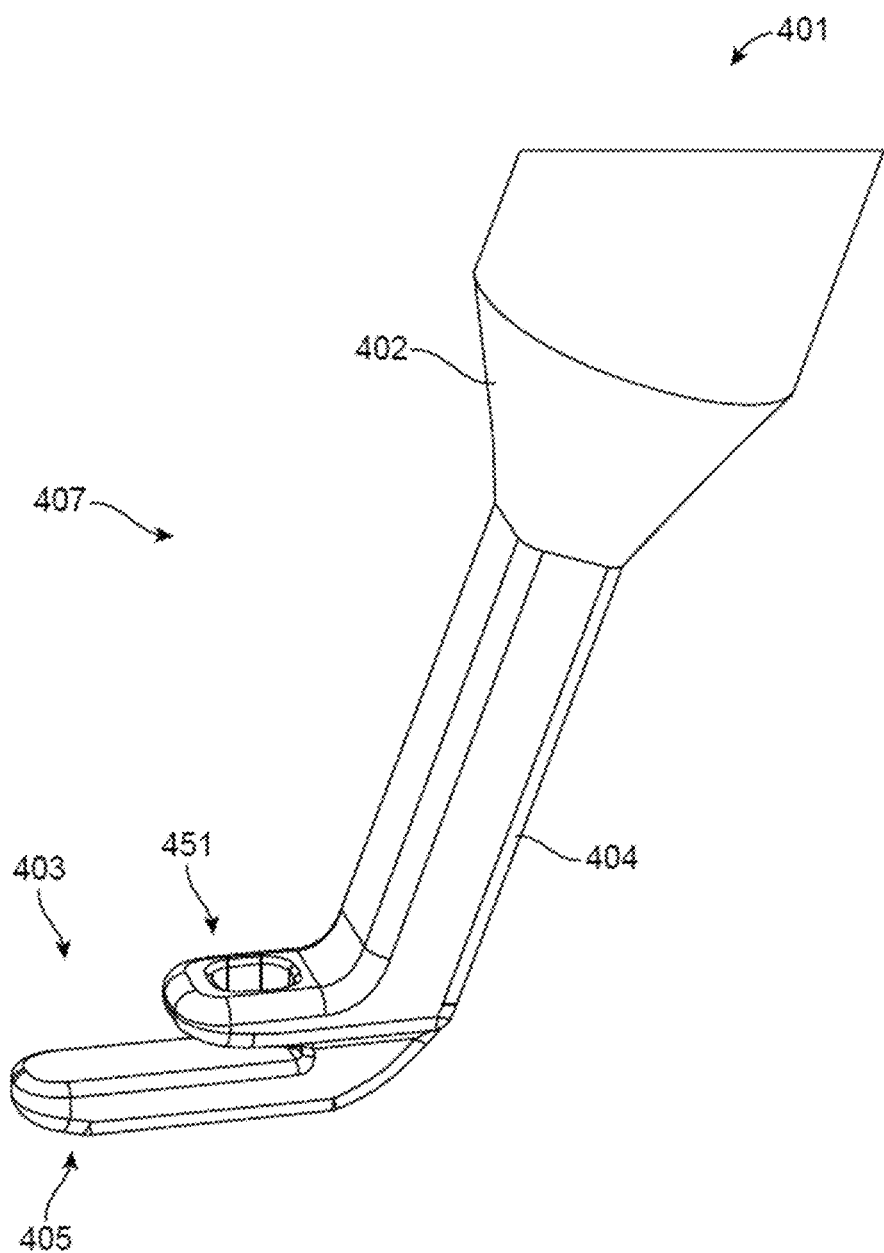

The tissue grabber 407 may comprise a proximal portion 404 that acts as an intermediary component to connect directly or indirectly the rest of the tissue grabber 407 to a distal portion of a shaft (not shown). For example, the tissue grabber may comprise an upper foot 451 that may extend proximal portion 404 and a guide foot 405 that may extend from a lower surface of the upper foot. The upper foot 451 may extend perpendicularly, or near perpendicularly, from the proximal portion 404, such that the longitudinal axis of the upper foot 451 may be perpendicular to, or near perpendicular to, the longitudinal axis of the shaft and/or proximal portion 404. The guide foot 405 may be coupled to the upper foot, for example, via a heel 410 of the guide foot 405, and the longitudinal axis of the guide foot 405 may be parallel or about parallel with the longitudinal axis of the upper foot 451 (such that the longitudinal axis of the guide foot 405 may be perpendicular to, or near perpendicular to, the longitudinal axis of the shaft and/or proximal portion 404). The radius of curvature of the heel may be between about 0.1 mm and about 1 mm, between about 0.2 mm and about 0.6 mm, about 0.1 mm, about 0.2 mm, about 0.4 mm, about 0.6 mm, about 0.8 mm, and about 1 mm. FIG. 12C shows a tissue grabber 407, in which the longitudinal axis of the upper foot 451 and the longitudinal axis of guide foot 405 are each oriented at an angle of about 110 degrees with respect to the longitudinal axis of the shaft 401 and/or the proximal portion 404.

The tissue grabbing region 403 may be a partially enclosed region of space bounded by one or more tissue grabbing surfaces and may comprise an opening 409 configured to receive tissue, such as trabecular meshwork, therethrough. The tissue grabbing region 403 may comprise an upper tissue grabbing surface 427 and a lower tissue grabbing surface 425 that connect at a closed back 411. The upper grabbing surface 427 may be coextensive with the plantar surface 452 of the upper foot and the lower gripping surface 425 may be coextensive with at least a portion of the dorsal surface 421 of the guide foot 405. In some variations, the front opening 409 may be aligned with a tip 453 of the upper foot 451. The tissue grabbing region 403 may be formed as a groove configured to receive, grip, trap and/or collect tissue therein. In this manner, the tissue grabber 407 may be configured to receive, trap, hold, or otherwise maintain a portion of tissue (e.g., trabecular meshwork) within or on the tissue grabbing region 403. When used in a goniotomy, the upper tissue grabbing surface 427 may be configured to be positioned above the trabecular meshwork and the lower tissue grabbing surface 425 may be configured to be positioned in Schlemm's canal and thus below the trabecular meshwork. The tissue grabbing region 403 may comprise one or a combination of two or more tissue grabbing mechanisms such as a variable height of the tissue grabbing region, tissue collection openings, and tissue grabbing protrusions as described herein above. As shown in FIG. 12A, the tissue grabbing region 403 comprises a variable height and a window 433 comprised in upper foot 451 that may function as a tissue collection opening.

The proximal portion 404 of the issue grabber 407 may couple to a shaft 401. In some variations, the width of the proximal portion 404 may be between about 30% and 70% of the width of the shaft. In some variations, a distal portion 402 of the shaft 40 may be tapered so that the width and/or the shape of the distal portion 402 transitions from the width and shape of the shaft 401 to the width and shape of the proximal portion 404 of the tissue grabber 407. In some variations, the proximal portion 404 may have an elongated shape, and may have a rectangular cross-section with rounded corners. The rounded corners may have a radius of curvature of between about 40 microns and about 60 microns, and all surfaces of the proximal portion may be electropolished. The proximal portion 404 may have a length of between about 0.5 mm and about 3 mm, by way of example about 2 mm. The proximal portion may have a width of between about 250 microns and about 400 microns, or between about 280 microns and about 320 microns. In some variations, the width of the proximal portion 404 may be the same as the width of the upper foot 451, and greater than the width of the guide foot 405.

The guide foot 405 may have a length of between about 550 microns and about 700 microns, or between about 620 microns and about 660 microns, as measured from the tip 417 and the closed back 411. The guide foot 405 may have and a width of about 200 microns and about 230, and may be sufficiently narrow such that it can readily enter Schlemm's canal when used in a goniotomy procedure. All corners of the guide foot 9 may be rounded, the rounded portions having a radius of curvature of between about 2 microns and about 100 microns. The tip 417 of the guide foot may be rounded, having radius of curvature of between about 30 microns and about 70 microns, and may have a tapering 418, at a tapering angle of between about 12 degrees and about 20 degrees with respect to the longitudinal axis on the guide foot 405. The entire surface of the guide foot 405 may be rounded and atraumatic. The upper foot 451 may have a length of between about 200 microns and about 400 microns, or between about 250 microns and about 350 microns, as measured from the tip 453 to the closed back 411, and a width of between about 250 microns and about 400 microns, or about 280 microns and about 320 microns. The upper foot may be sufficiently wide that that it cannot readily enter Schlemm's canal and rather presses on top of the trabecular meshwork when used in a goniotomy procedure. The width of the upper foot 451 may be the same as the width of the proximal portion 404. All corners of the upper foot 451 may be rounded, the rounded portions having a radius of curvature of between about 2 microns and about 100 microns. The upper foot 451 may be rounded, having a radius of curvature of between about 30 microns and about 70 microns and may be tapered, at a tapering angle of between about 8 degrees and about 15 degrees with respect to the longitudinal axis on the upper foot 451. The entire surface of the upper foot 9 may be rounded and atraumatic.

FIG. 12B shows a front view of the tissue manipulation and/or tear device 400 depicted in FIG. 12A. The difference in width between the two feet can clearly be seen in FIG. 12B. For example, as shown there, the upper foot 451 may be wider than the guide foot 405. The guide foot 405 may be configured to be inserted into Schlemm's canal. The upper foot 451 may be too wide to fit inside the canal. As such, when the device is used in a goniotomy, guide foot 405, but not the upper foot 451, may be inserted into Schlemm's canal of a subject's eye, and the upper foot may press on top of the trabecular meshwork when the device 400 is used in a goniotomy. As a result, a portion of the trabecular meshwork is fed into the tissue grabbing region 403, with the upper grabbing surface 427 above the trabecular meshwork and the lower grabbing surface 425 below the trabecular meshwork. In certain variations, the tissue grabbing region 403 may comprise a first side and a second side, wherein the first and second sides are open, so that an initially intact trabecular meshwork may be fed into the tissue grabbing region.

The height of the tissue grabbing region 403 may be variable so that the height decreases from the front opening 409 of the closed back 411 of the tissue grabbing region 403. The closed back may not end in a sharp corner, but rather may have a rounded, atraumatic shape, and all nearby corners and/or edges may be machined or polished to be rounded. In the context of the device being use for trabeculectomy, the trabecular meshwork fed into or received in the tissue grabbing region 403 may not encounter any sharp edges or cutting mechanisms.

In this variation, the height of the grabbing region 403 (in the form of a groove as shown in FIG. 10) at the front opening is about 70 microns. The closed back 411 has a rounded shape with a radius of curvature of about 15 microns, so that the height of the tissue grabbing region 403 at the closed back 411 is about 30 microns, which is the height of about 4 red blood cells. Therefore, the height of the closed back is about 43% of the height of the front opening. When the tissue grabber 407 is advanced along Schlemm's canal, the portion of trabecular meshwork that enters the tissue grabbing region 403 through the open front 409 becomes compressed as it approaches the closed back 411. Moreover, the upper foot 451 is sufficiently wide to cover Schwalbe's line and the scleral spur, thus preventing the compressed trabecular meshwork tissue from escaping from tissue grabbing region 403. Moreover, lateral portions (such as the roots) of the trabecular meshwork that enter the tissue grabbing region 403 gets pulled as the tissue grabber 407 is advanced, resulting in the lateral portions getting stretched and eventually torn or avulsed. As a result, as more of the trabecular meshwork gets pulled and detached from the eye, the detached tissue gets stuck within the tissue grabbing region 403.

During the goniotomy procedure, window 433 may serve as a release for the compressed trabecular meshwork that is being collected. Therefore, as the tissue grabber 407 is advanced along Schlemm's canal, and tissue grabbing region 403 continues to fill up with the detached, compressed trabecular meshwork tissue, some of the tissue gets forced into window 433, thereby further enmeshing the detached trabecular meshwork tissue within the tissue grabbing region 403.

Figure 22A:
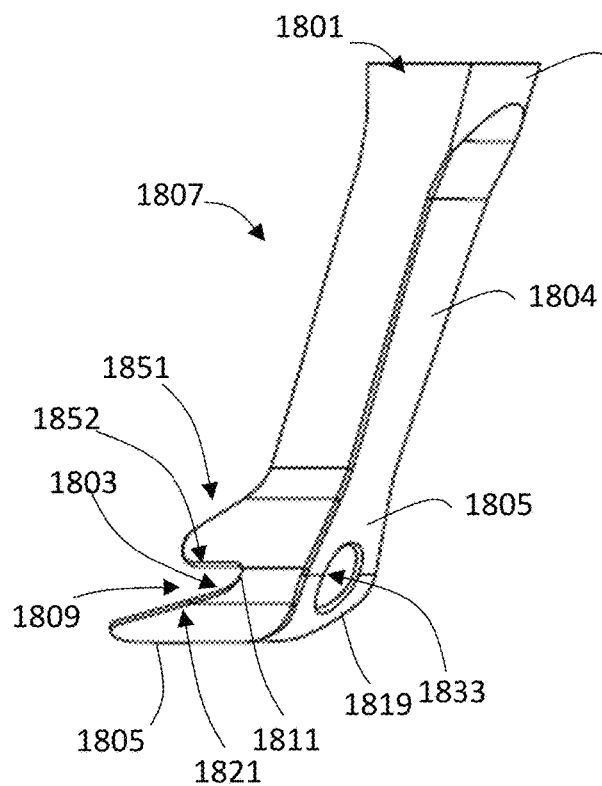
FIGS. 22A-22B shows multiple views of a variation of a tissue grabber.
Figure 22B:
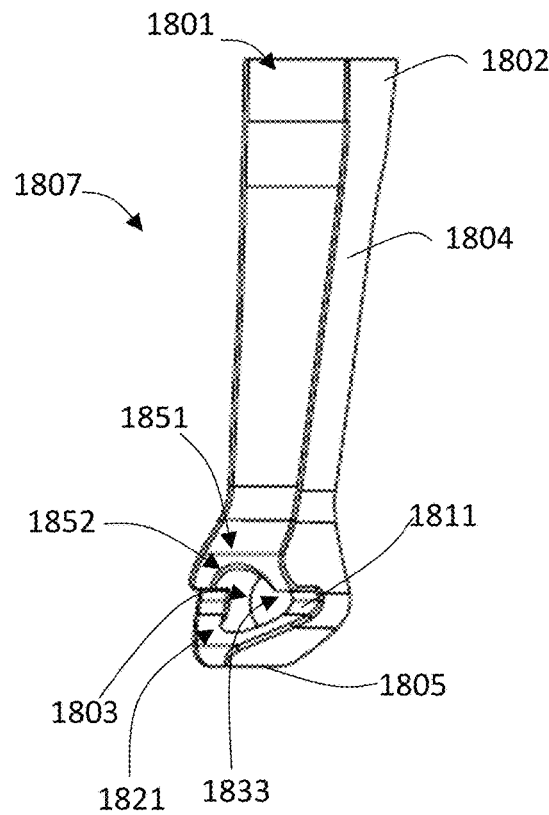

In some variations, the tissue grabbers described herein may comprise a window located at the back of the tissue grabbing region. One example is shown in FIG. 7D. In another example, FIGS. 22A-22B depict an exemplary tissue grabber 1807 comprising a window 1833 located at the back of the tissue grabbing region 1803. The tissue grabber 1807 may be fixedly or removably coupled to a distal end 1802 of a shaft 1801, and may comprise a proximal region 1804, a guide foot 1805, an upper foot 1851, and a tissue grabbing region 1803 formed between the plantar surface 1852 of the upper foot 1851 and the dorsal surface 1821 of the guide foot 1805. The tissue grabbing region 1803 may comprise a front opening 1809 as well as a window 1833 at the back of the tissue grabbing region. The window 1833 may be configured as a bore with a circular cross section that creates an opening between the closed back 211 portion of the tissue grabbing region 1803 and a portion of the back surface 1805 of the tissue grabber, optionally near the heel 1819. In some variations, as shown by way of example in FIGS. 22A-22B, the bore may extend through at least a portion of the upper foot 1851 and/or the guide foot 1805. During the goniotomy procedure, the window 1833 may serve as a tissue collection opening and may collect tissue (e.g., trabecular meshwork) entering through the front opening 1809. In some variations, the tissue may be compressed in the tissue grabbing region 1803 prior to collection in the window 1833. In some variations, the tapering of the guide foot 1805 may function to direct trabecular meshwork tissue into the tissue grabbing region 1803 and towards the window 1833. As the tissue grabber 1807 is advanced along Schlemm's canal and the tissue grabbing region 1803 fills with detached and/or compressed trabecular meshwork tissue, some of the tissue may be forced into or otherwise positioned within the window 1833.

Figure 12D:
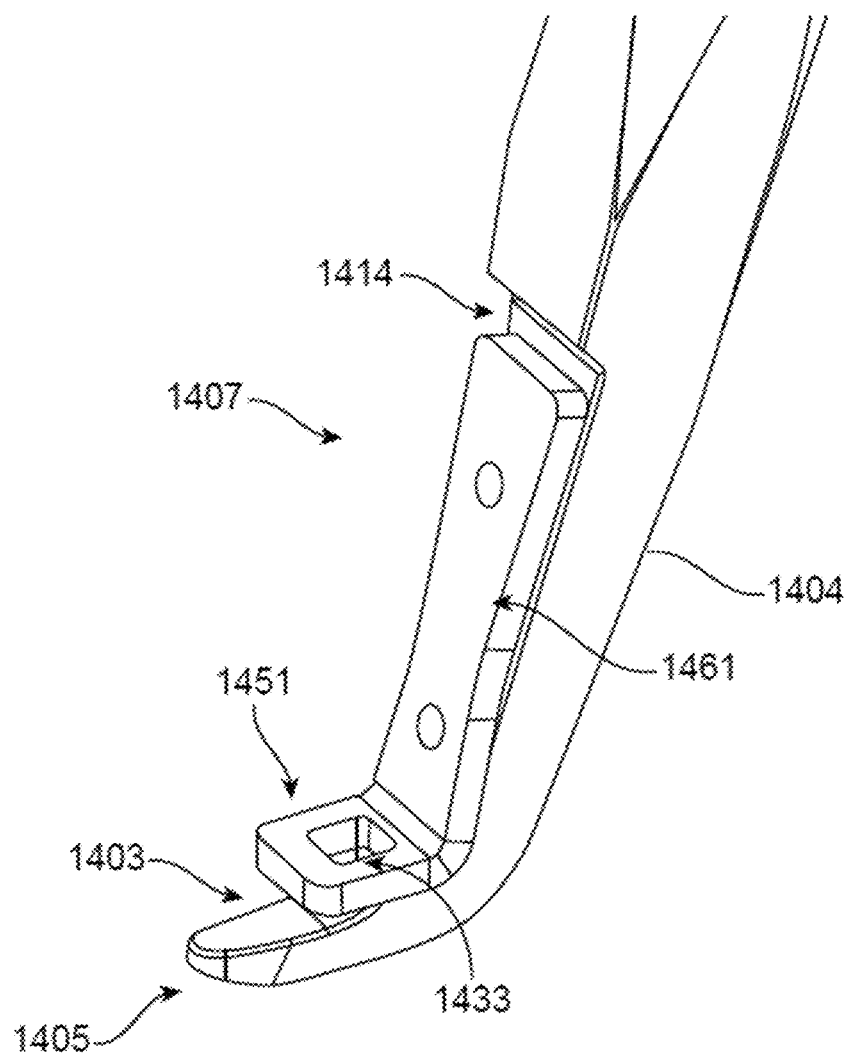
FIG. 12D shows a variation of a tissue grabber in which an upper foot is machined separately, then attached to a proximal portion of a tissue grabber.
Figure 12E:
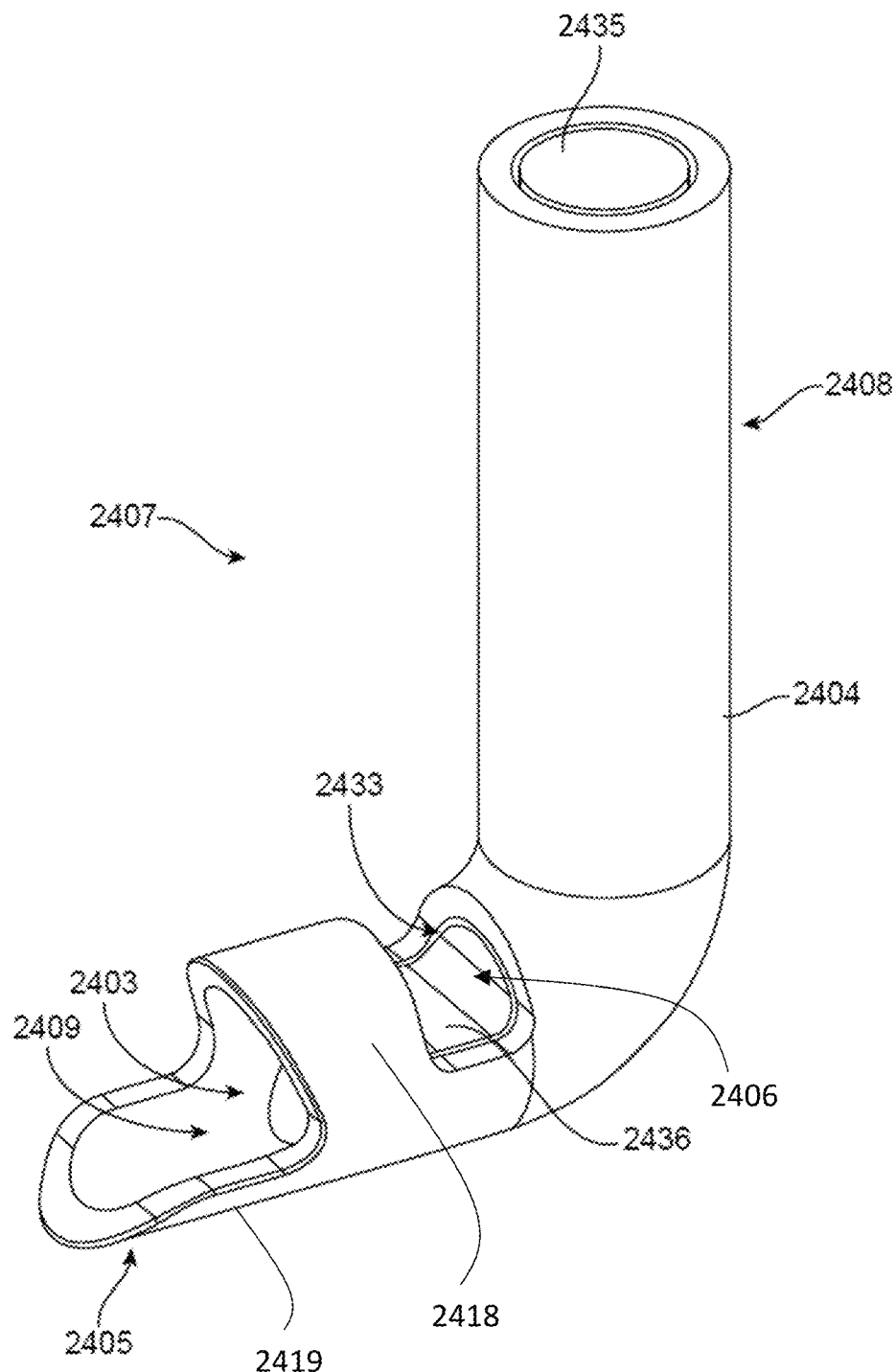
FIG. 12E shows a variation of a tissue grabber formed out of a tubular structure.

In some variations, the guide foot, the upper foot, and the proximal portion of a tissue grabber may be integral and be shaped or formed out of a common material. This may be accomplished, for example, by laser machining, by EDM (electrical discharge machining), or the like. Examples of an integral design of the tissue grabber is shown in, for example, FIGS. 12A-12C. In other variations, the guide foot and/or the upper foot of a tissue grabber may be machined separately, then attached to the proximal portion through, by way of example, welding, soldering, bonding, riveting, or the like. FIG. 12D shows an exemplary tissue grabber 1407 that similar to tissue grabber 407 shown in FIG. 12C, except that the upper foot and proximal portion of that variation are not integrally formed. In the variation shown in FIG. 12D, riveting is used to connect the upper foot 1451 and proximal portion 1404, though any suitable joining technique may be used. In some variations where a joining technique is used, the issue grabber 1407 may comprise an indentation 1414 to provide space for a connecting flange 1461. By using indentation and the connecting flange, the atraumatic shape of the device is preserved In some variations, the tissue grabbers described herein may be formed from a tubular structure. By way of example, FIG. 12E shows a tissue grabber 2407 comprising a tubular structure 2408. The tissue grabber 2407 may comprise a proximal region 2404, a guide foot 2405, a tissue grabbing region 2403 that has a front opening 2409. The tissue grabbing region 2403 may be coextensive with a channel, which may, in some variations, be a portion of a lumen of the tubular structure 2408, between the opening 2409 and the angled surface 2436, and at least partially bounded by sidewalls (e.g., distal sidewalls 2419 and/or a central sidewall 2418) of the tubular structure 2408. The sidewalls of the tubular structure 2408 may partially or wholly circumferentially surround the tissue grabbing region 2403. For example, the tubular structure 2408 may comprise distal sidewalls 2419 partially circumferentially enclosing a distal portion of the tissue grabbing region 2408 and a central sidewall 2418 fully circumferentially enclosing a proximal portion of the tissue grabbing region 2408. Put differently, the distal sidewalls _____ of the tubular structure 2408 may form a semi-circular or semi-elliptical cross-section while the central sidewalls _____ may form a circular or elliptical cross-section. In this manner, at least a portion of the tissue grabbing region 2403 may be partially (e.g., the portion defined by the distal sidewalls) or fully (e.g., the portion defined by the central sidewall) enclosed on its sides (in comparison, the tissue grabbing region 403 of tissue grabber 407 shown in FIG. 12A may be bounded by the upper tissue grabbing surface 427 and the lower tissue grabbing surface 245, but is open on the sides).

The tubular structure 2408 need not be perfectly cylindrical in geometry and may or may not have a lumen entirely therethrough. For example, in some variations, the tubular structure 2408 may comprise a lumen and a solid inner core 2435 positioned within the lumen to, for example, help provide structural support. In other variations, the tubular structure 2408 may not have a lumen therethrough and the channel or opening may be formed at the distal end of the tubular structure 2408 between the central sidewall 2418 and the distal sidewall 2419, thus forming the tissue grabbing region 2403. In these variations, the tissue grabber 2407 may still comprise a solid inner core, but the inner core may be integrally formed with the tubular structure 2408. The solid inner core may be made of any suitable material, for example stainless steel. Forming the tissue grabber from a tubular structure may be accomplished in any suitable manner, such as for example, by laser machining, by EDM, or the like, and may have the benefit of, for example, lower cost construction, the natural "mouth" profile of the open end of the tube acting as a trap, and the sides of the tube forming non-parallel walls. The tubular structure 2408 may be made out of any suitable material, such as nitinol, stainless steel, titanium, and the like.

In some variations of tissue grabbers comprising a tissue collection opening, the closed back of the tissue grabber opposite the front opening may be configured as an angled surface that directs trabecular meshwork tissue from the tissue grabbing region into the tissue collection opening. As shown in FIG. 12E, in some variations, the tissue grabber 2407 may comprise a window 2433 in a portion of the tubular structure 2408, with the window being in communication with the channel or lumen of the tubular structure 2408. In some variations, the tissue grabber 2407 may comprise an angled surface 2436 may be located at the proximal end 2406 (which may alternatively be referred to as the back end) of the tissue grabbing region 2403 that is opposite the front opening 2409, and located adjacent the window 2433. In some variations, a surface of the solid inner core 2435 within the lumen of the tubular structure (e.g., aligned with or otherwise positioned under the central sidewall 2418) may form the angled surface 2436. The angled surface 2436 may form an oblique angle with respect to the longitudinal axis of the channel or lumen of the tubular structure 2408, and the oblique angle may function to guide (e.g., redirect) the trabecular meshwork in the tissue grabbing region 2403 towards the window 2433. As the tissue grabber 2407 is advanced within and relative to Schlemm's canal, trabecular meshwork tissue may be directed into the tissue grabbing region 2403 by the tubular nature of the device (e.g., by the distal and/or central sidewalls 2419, 2418 of the tubular structure). Then, when the tissue encounters the angled surface 2436, the force generated by the advancement of the tissue grabber that directs the tissue towards the proximal end of the tissue grabbing region redirects the tissue towards the window 2433. In some variations, the angled surface 2436 and the window 2433 may be configured to direct the trabecular meshwork through and out of, rather than be accumulate in, tissue grabbing region 2403. For example, in some variations, the tissue may be directed through the window 2433 and out of the tubular structure 2408.

Figure 23A:
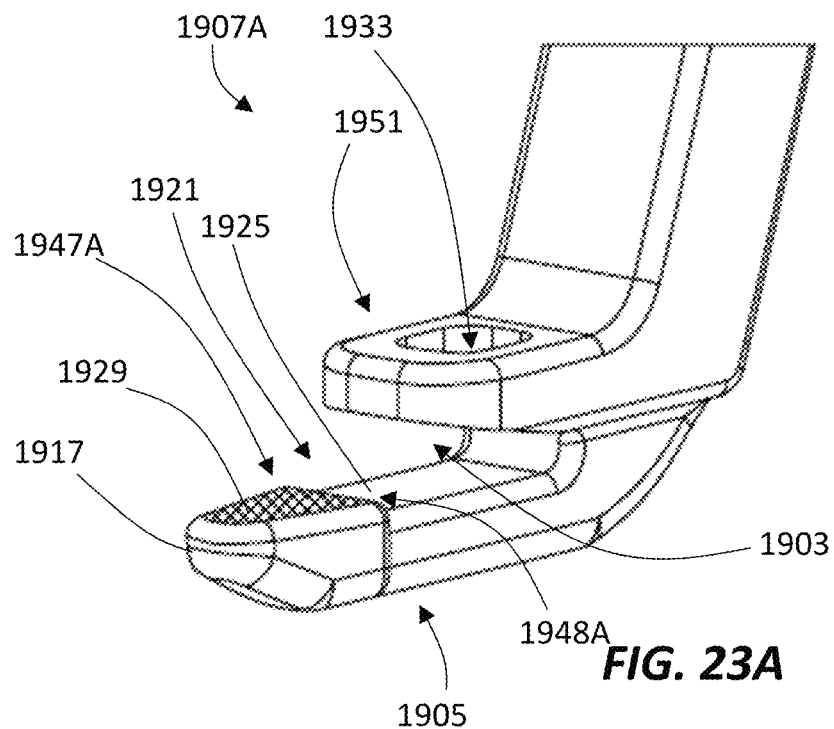
FIGS. 23A-23B show variations of a tissue grabber having a roughened surface on the dorsal surface of the guide foot.
Figure 23B:
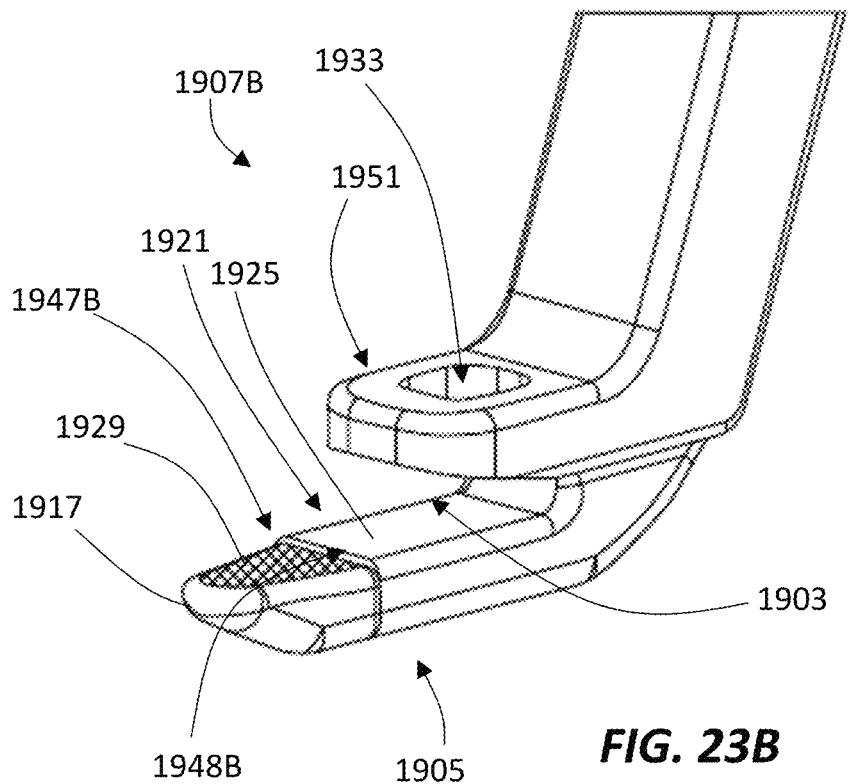

As described herein above by way of example with respect to FIGS. 18A-18C, in some variations, the upper tissue grabbing surface and/or the lower tissue grabbing surface, or a portion thereof, may have a roughened surface compared to other surfaces of the upper foot and the guide foot. For example, FIGS. 23A and 23B depict variations of a tissue grabber 1907A, 1907B having a roughened surface 1947A, 1947B. The tissue grabber comprises an upper foot 1951 comprising a window 1933 and a guide foot 1905, with a tissue grabbing region 1903 disposed therebetween. A portion of a lower tissue grabbing surface 1925 on the dorsal surface 1921 of the guide foot 1905 may comprise the roughened surface 1947A, 1947B. In some variations, the roughened surface may comprise a plurality of microcraters 1929. As described elsewhere throughout, the microcraters may be formed in any suitable way, have any suitable geometry, and be of any suitable size. In some variations, the roughened surface 1947A, 1974B may be positioned at or adjacent to the tip 1917 of the guide foot 1905. In some variations, the roughened surface 1947A, 1974B may be located on the guide foot 1905 past, or aligned with, the distal edge of the upper foot 1951. In some variations, the roughened surface maybe raised or lowered related to the non-roughened surface. In the variation shown in FIG. 23A, the roughened surface 1947A is raised relative to the rest of the dorsal surface 1921 of the guide foot 1905 (i.e., the non-roughened surface of the guide foot 1905 is lower than the roughened surface), such that a step 1948A is formed between the non-roughened and roughened surfaces. In the variation shown in FIG. 23B, the non-roughened dorsal surface 1921 of the guide foot 1905 is raised relative to the roughened surface 1947B (i.e., the roughened surface is lower than the rest of the dorsal surface 1921 of the guide foot 1905) such that a step 1948B is formed between the non-roughened and roughened surfaces.

Figure 23C:
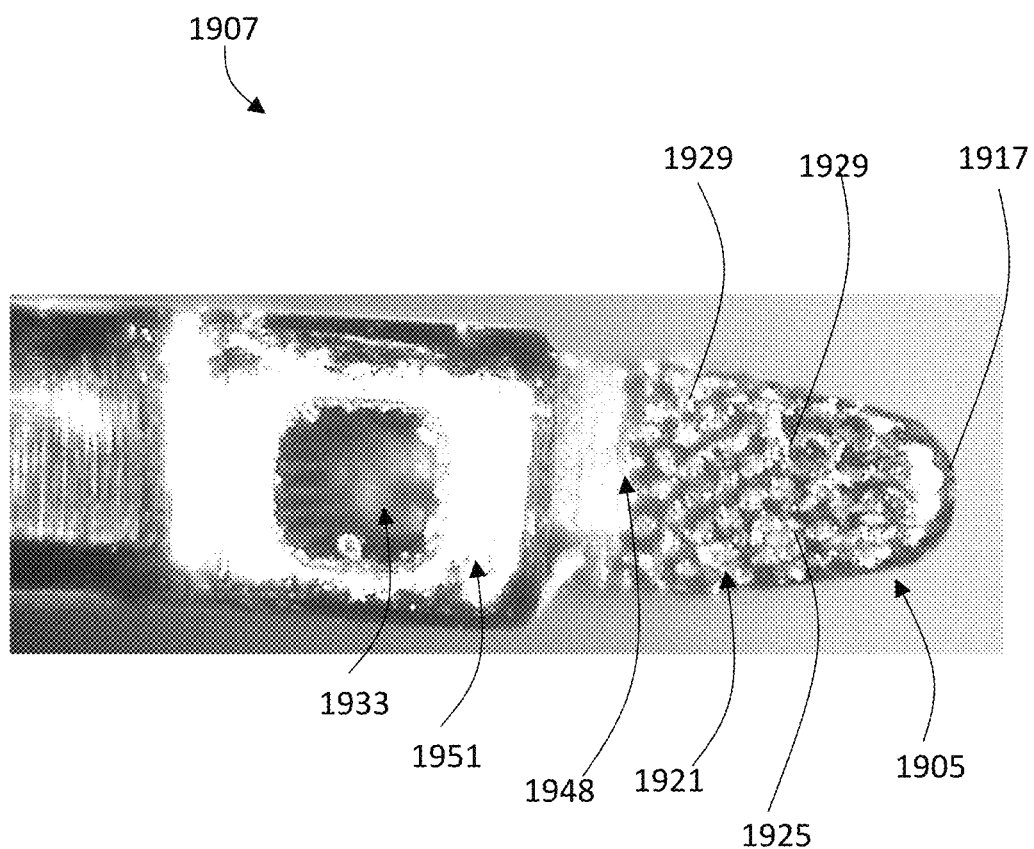
FIG. 23C shows a close-up photograph of a manufactured example of a tissue grabber comprising a roughened surface on the dorsal surface of the guide foot.

FIG. 23C is a magnified photograph of a variation of a tissue grabber 1907C. As shown there, the tissue grabber 1907C may comprise an upper foot 1951 comprising a window 1933 and a guide foot 1905, with the tissue grabbing region 1903 situated therebetween. A portion of a lower tissue grabbing surface 1925 on the dorsal surface 1921 of the guide foot 1905 comprises the roughened surface 1947. The roughened surface 1947 is situated towards the tip 1917 of the guide foot 1905, and the roughened and non-roughened surfaces are separated by a step 1948. In this variation, the roughened surface comprises a plurality of microcraters 1929. In the example shown in FIG. 23C, the microcraters 1929 are about 25 microns in diameter, and have been created using femtosecond laser pulses.

In some variations, the tissue grabber may comprise one or more movable portions or components. For example, the upper foot, or another portion of the tissue grabber may be movably attached to proximal portion or shaft, so that the upper tissue grabbing surface of the tissue grabber is movable relative to the lower tissue grabbing surface. In this way, the distance between the upper and lower tissue grabbing surfaces may be adjustable to control the depth grabbed tissue.

Figure 20A:
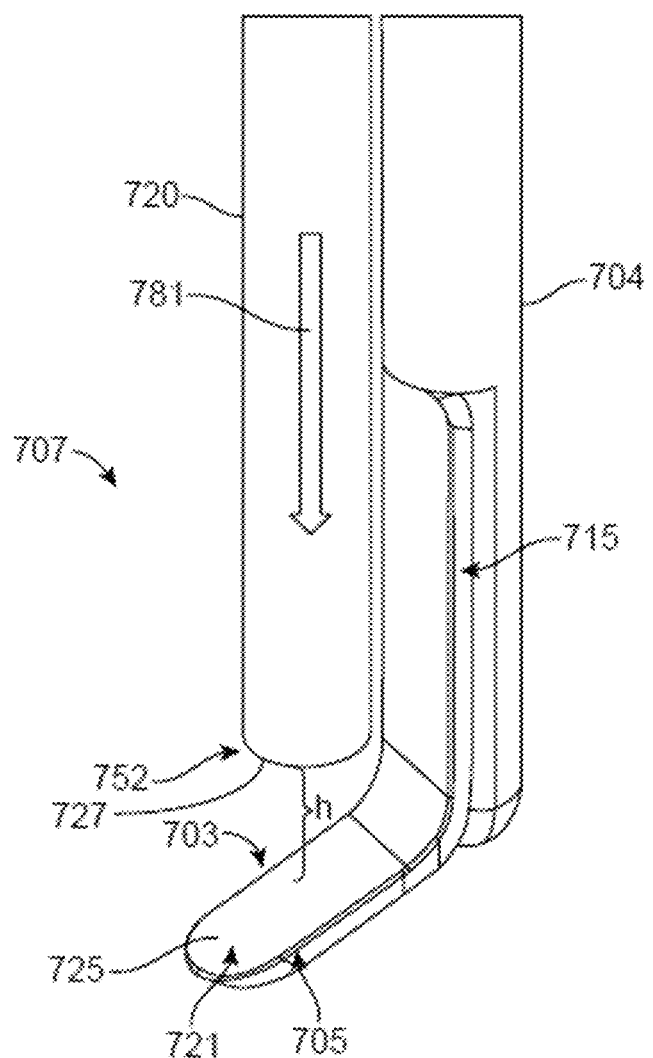
FIGS. 20A-20C show variations of a tissue grabber having a movable piston that can be toggled between an open position and a closed position.
Figure 20B:
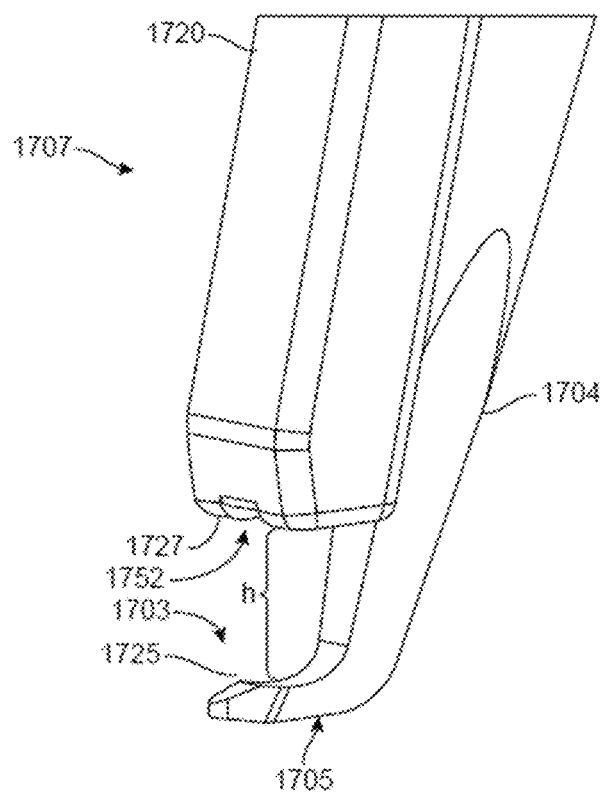
Figure 20C:
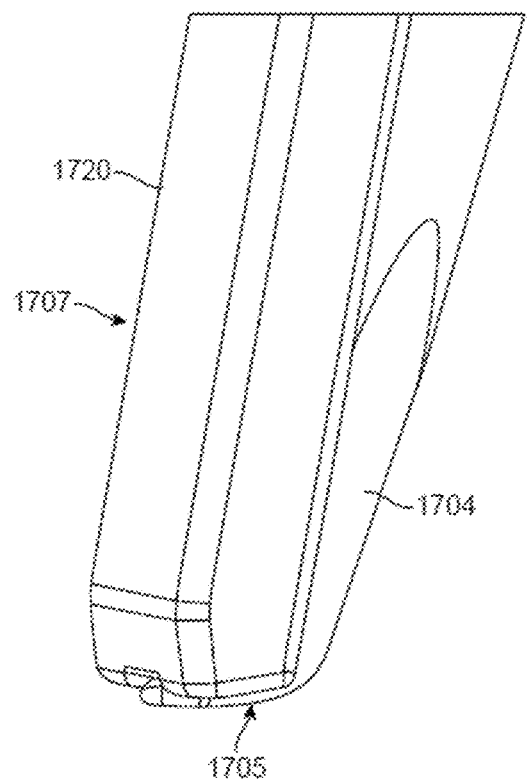

One example of a tissue grabber having one or more movable components is shown in FIG. 20A. Shown there is tissue grabber 707, comprising a proximal region 704, a guide foot 705 connected to the proximal region optionally through a connecting flange 715, and a movable piston 720. The plantar surface 752 of the piston 720 serves as upper tissue grabbing surface 727, and the dorsal surface 721 of the guide foot 705 serves as a lower tissue grabbing surface 725, forming the tissue grabbing region 703 therebetween. As schematically indicated by block arrow 781, the piston 720 is movable along a longitudinal axis of the piston, so that the height h of the tissue grabbing region 703 is adjustable and can further toggle between a completely open position and a completely closed position. FIGS. 20B-20C show an alternative variation of a tissue grabber 1707 comprising a proximal region 1704, a guide foot 1705, and a moveable piston 1702. FIG. 20B shows the tissue grabber with the tissue grabbing region 1703 in an open position, and FIG. 20C shows the same tissue grabber with the tissue grabbing region in a closed position, after the piston 1720 has been actuated. The plantar surface 1752 of the piston 1720 serves as upper tissue grabbing surface 1727, and the dorsal surface 1721 of the guide foot 1705 serves as a lower tissue grabbing surface 1725, forming the tissue grabbing region 1703 therebetween.

Figure 13:
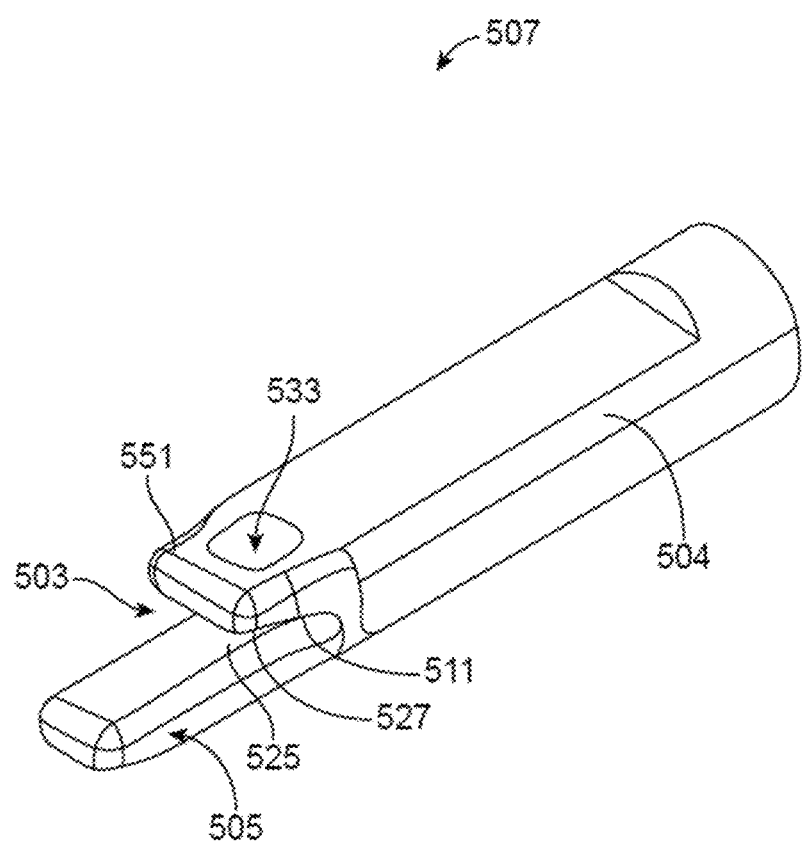
FIG. 13 show a variation of a tissue grabber with a tissue grabbing region located between an upper foot and a lower guide foot.

In some variations, the guide foot and/or upper foot of a tissue grabber may have a central longitudinal axis that is parallel to a longitudinal axis of the proximal portion of the tissue grabber. FIG. 13 shows, by way of example, a tissue grabber 507 that, like the tissue grabber 407 shown in FIGS. 12A-12B and the tissue grabber 207 shown in FIG. 10, may comprise an upper foot 551 and a guide foot 505, with a tissue grabbing region 503 formed between a plantar surface of the upper foot 551 and a dorsal surface of the guide foot 505. As can be seen in FIG. 13, the upper foot 551 may comprise a window 553. Similarly to the tissue grabber depicted in FIGS. 12A-12B, the upper foot 551 may be wider than the guide foot 505. However, unlike the tissue grabber 407 or the tissue grabber 207, both the upper foot 551 and the guide foot 505 of tissue gabber 507 extend along an axis that is parallel to that of the proximal portion 504.

The tissue grabber 507 comprises a proximal portion 504 that acts as an intermediary component to connect directly or indirectly the rest of the tissue grabber 507 to a distal portion of a shaft (not shown). The length of proximal portion 504 may be between about 1 mm and 1.2 mm and its width may be between about 380 microns and about 420 microns. The proximal portion 504 may be sufficiently wide to function as a base for both the upper foot 551 and the guide foot 505. All corners of the proximal portion 504 may be rounded. By way of example, in this variation, the rounded portions have radius of curvature of about 2 microns. In this variation, the respective longitudinal axes of the proximal portion 504, the guide foot 505, and the upper foot 551 are parallel to one another. However, it will be appreciated that the upper foot and guide foot may be in other, non-parallel orientations as well, as described herein above.

The proximal portion 504 may be coupled to the distal end of the shaft (not shown), and may be positioned to have its longitudinal axis at any desired angle relative to the longitudinal axis of the shaft, including coaxially and at an angle, which may be between about 80 degrees and about 140 degrees, including any values and sub-ranges therein, In some variations, the angle between longitudinal axis of the proximal portion 504 and the longitudinal axis of the shaft may be between about 85 degrees and 95 degrees, about 80 and about 100 degrees, about 80 degrees and about 95 degrees, about 90 degrees and about 100 degrees, about 90 degrees and about 120 degrees, about 100 degrees and about 130 degrees, and about 120 degrees and about 140 degrees.

The tissue grabbing region 503 may provide an opening where tissue (such as a trabecular meshwork) may be inserted for pulling and removal through tearing, stripping, ripping, or avulsion. The tissue grabbing region may comprise by an upper tissue grabbing surface 527 and a lower tissue grabbing surface 525 that connect at a closed back 511. The upper gripping surface 527 may be coextensive with the plantar surface of the upper foot and the lower gripping surface 525 may be coextensive with at least a portion of the dorsal surface of the guide foot 505. The tissue grabbing region 503 may be formed as a groove configured to receive, grip, trap and/or collect tissue therein. In this manner, the tissue grabber 507 may be configured to receive, trap, hold, or otherwise maintain a portion of tissue (e.g., trabecular meshwork) within or on the tissue grabbing region 503. When used in a goniotomy, the upper tissue grabbing surface 527 may be configured to be positioned above the trabecular meshwork and the lower tissue grabbing surface 525 may be configured to be positioned in Schlemm's canal and thus below the trabecular meshwork. The tissue grabbing region 503 may comprise one or a combination of two or more tissue grabbing mechanisms such as a variable height of the tissue grabbing region, tissue collection openings, and tissue grabbing protrusions as described herein above. In this variation, the tissue grabbing region 503 is shaped to have a variable height and a window 533 comprise in upper foot 551 that may function as a tissue collection opening. The upper tissue grabbing surface 527 and the lower tissue grabbing surface 525 may have a roughened surface compared to other surfaces of the upper foot 551 and the guide foot 505.

The length of upper foot 551 may be between about 260 microns and about 300 microns and its width may be between about 280 and about 320 microns. The upper foot may be sufficiently wide so that it cannot enter Schlemm's canal and instead presses on the top of the trabecular meshwork when used for performing goniotomy. All corners of the upper foot 551 may be rounded. By way of example in this variation, the rounded portions may have a radius of curvature of about 2 microns. The upper foot 551 may tapered, at a tapering angle in this variation by way of example being between about 8 degrees and about 14 degrees with respect to the longitudinal axis of the upper foot. The entire surface of the upper foot 551 may be rounded and atraumatic.

By way of example as shown in FIG. 13, the length of the guide foot 505 may be between about 620 microns and about 660 microns and its width may be between about 200 microns and about 240 microns. The guide foot may be sufficiently narrow that it can readily enter Schlemm's canal. All corners of the guide foot 505 may be rounded. By way of example in this variation the rounded portions may have a radius of curvature of about 2 microns. The tip of the guide foot 505 may be tapered at a tapering angle in this variation by way of example being 16 degrees with respect to the longitudinal axis of the guide foot 505.

It can be seen in FIG. 13 that upper foot 551 is wider than guide foot 505. When used for performing goniotomy, guide foot 505 is configured to be readily inserted into Schlemm's canal, and upper foot 551 is too wide to fit inside the canal. Guide foot 505, but not the upper foot 551, is inserted into Schlemm's canal of a subject's eye for the procedure. As a result, a portion of the trabecular meshwork is fed into the tissue grabbing region 503, with the upper grabbing surface 527 above the trabecular meshwork and the lower grabbing surface 525 below the trabecular meshwork. In certain variations, the tissue grabbing region 503 may comprise a first side and a second side, wherein the first and second sides are open, so that an initially intact trabecular meshwork may be fed into the tissue grabbing region.

The height of the tissue grabbing region 503 is variable so that the height decreases from the front opening 509 to the closed back 511. The closed back does not end in a sharp corner, but rather has a rounded shape, and all nearby corners have been machined or polished to be rounded. In the context of the device being use for tearing goniotomy, the trabecular meshwork fed into the tissue grabbing region 403 does not encounter any sharp edges or cutting mechanisms. The height of the groove-shape tissue grabbing region 503 at the front opening is about between about 70 and about 75 microns. The closed back 2 may have a rounded shape with a radius of curvature of between about 10 microns and about 15 microns, so that the height of the tissue grabbing region 503 at the closed back 411 is between about 20 microns and about 30 microns. In some variations, the height of the closed back may be between about 0.25% and about 0.45% of the height of the front opening.

When the tissue grabber 507 is advanced along Schlemm's canal, the portion of trabecular meshwork that enters the tissue grabbing region 503 through the open front becomes compressed as it approaches closed back 511. Moreover, the upper foot 551 is sufficiently wide to prevent the compressed trabecular meshwork tissue from escaping out of tissue grabbing region 503. Moreover, the lateral portions (such as the roots) of the trabecular meshwork that enters the tissue grabbing region 403 gets pulled as the tissue grabber 407 is advanced, resulting in the lateral portions getting stretched and eventually torn or avulsed. As a result, as more of the trabecular meshwork gets pulled and detached from the eye, the detached trabecular meshwork tissue gets stuck within the tissue grabbing region 503.

During a tearing goniotomy procedure, window 553 may serves as a release valve for the compressed trabecular meshwork that is being collected. In this variation, window 553 is located in upper foot 551, and is a rectangular window that is dimensioned to have a width of between about 120 microns and about 180 microns and a length of between about 160 microns and about 200 microns. In some variations, the internal corners of the window may be rounded with a radius of curvature of about 2 microns. Therefore, as the tissue grabber 507 is advanced along Schlemm's canal, and the tissue grabbing region 403 continues to fill up with the detached, compressed trabecular meshwork tissue, some of the tissue gets forced into window 553, thereby further enmeshing the detached trabecular meshwork tissue within and around the tissue grabbing region 503.

Methods

Described herein are also methods for performing a controlled tearing of a small piece of tissue in the body of a subject. The small piece of tissue may be any piece of soft, non-bone tissue that has a thickness of about 200 microns or less, about 150 microns or less, or about 100 microns or less, and has a width of about 2000 microns or less, about 1500 microns or less, about 1000 microns or less, or about 750 microns or less. In some variations, the tissue is an intraocular tissue, such as trabecular meshwork.

The method may make use of any one of the variations of the tissue manipulation and/or tearing device described herein. It will be appreciated that a variety of tissue manipulation and/or tearing devices with selected differences in dimensions and designs may be provided, and that a trained user of the device may select a device that is most suited for the size of the tissue being manipulated and/or torn. Generally, the tissue manipulation and/or tearing devices may comprise a tissue grabber at a distal end of a shaft, and the tissue grabber may comprise a guide foot (optionally in addition a second, upper foot) and a tissue grabbing region. The tissue grabbing region may comprise a front opening, an upper grabbing surface, a lower grabbing surface (that may be coextensive with a surface of the guide foot), and a closed back, and may be configured to receive and hold tissue (such as the trabecular meshwork) inserted therein. The tissue grabbing regions may comprise a groove, mouth, crevice, cavity, indentation, gap, open space, notch, or other shape that is configured to receive a portion of tissue. In the context of tearing and removing trabecular meshwork from an eye of a subject, the device may be referred to as a goniotomy device, and the method described herein may be referred to as a "tearing goniotomy".

A tearing goniotomy may comprise: (a) advancing a tissue grabber to Schlemm's canal of the eye; (b) advancing a tip of the guide foot of the tissue grabber through the trabecular meshwork at an insertion point and into Schlemm's canal, and (c) advancing the guide foot within and relative to Schlemm's canal, wherein as the guide foot is advanced, a first central portion of the trabecular meshwork becomes trapped in the tissue grabbing region and a second, lateral portion of the trabecular meshwork is detached from surrounding tissue. The method may further comprise withdrawing the tissue grabber to remove the trapped trabecular meshwork.

Methods for tearing the trabecular meshwork will be described in further detail with reference to FIGS. 14A-14E. These figures show a side view (FIGS. 14A-14D) or top view (FIG. 14E) of Schlemm's canal, as well as an exemplary tissue grabber 607 of a tissue manipulation and tearing device with respect to the various tissues comprised in or around Schlemm's canal 661 while performing an exemplary tearing goniotomy. The tissue grabber 607 as shown in FIGS. 14A-14E comprises a guide foot 605 and an upper foot 651, and the space or groove between the guide foot and the upper foot forms a tissue grabbing region 603. The tissue grabbing region comprises a front opening 609, an upper grabbing surface 627 coextensive with a plantar surface of the upper foot 651, a lower grabbing surface 625 partially coextensive with a dorsal surface of the guide foot 605, and a closed back 611. The tissue grabber 607 may comprise a tissue collection opening, which may be a window 633 (shown in FIG. 14E) formed in the upper foot 651. As shown in FIGS. 14A-14D, Schlemm's canal 661 comprises a lumen bounded in part by the trabecular meshwork 663 located on the dorsal side of the canal and an outer wall 664 located on the ventral side of the canal 661. FIGS. 14E-14E show a top view of Schlemm's canal 661, the trabecular meshwork 663, and relevant portions of the tissue grabber 607 inside or near the canal 661 and/or meshwork 663. As shown in these figures, the trabecular meshwork 663 is attached on its anterior side to Schwalbe's line and on its posterior side to the scleral spur. The lateral portion of the trabecular meshwork that attaches to Schwalbe's line may be referred to as the trabecular meshwork's anterior attachments or roots, and lateral portion of the trabecular meshwork that attaches to the scleral spur may be referred to as the trabecular meshwork's posterior attachments or roots. The anterior attachments or roots and posterior attachments or roots may, in the aggregate, be referred to herein as roots or lateral roots.

A) Advancing a Tissue Grabber to Schlemm's Canal of the Eye

Referring now to FIG. 14A, in some variations, the goniotomy device may be inserted into the eye and advanced to Schlemm's canal through one or various surgical access routes, including a trans-corneal, a trans-scleral, and a trans-limbal route. In a trans-corneal or trans-limbal route, the tissue grabber 607 may be advanced to Schlemm's canal 661, and/or to the trabecular meshwork 663 located above and covering Schlemm's canal 661, through the eye's anterior chamber 665 (ab interno). An exemplary trans-corneal advancing of a tissue grabber comprised in the goniotomy device from an incision made in temporal cornea, through the anterior chamber, towards a portion of Schlemm's canal in the nasal region of the eye is shown by way of example in FIG. 2B.

By way of example, a temporal-to-nasal trans-corneal advancement of the goniotomy device may be performed as follows: A corneal paracentesis wound may be created, and the anterior chamber may be filled with a viscoelastic fluid, by way of example hyaluronic acid, chondroitin sulfate, cellulose, or salts, derivatives, or mixtures thereof. After the anterior chamber is filled with viscoelastic fluid, a 1 mm to 3 mm incision may be made in the temporal cornea, and a Swan Jacob gonioprism may be coupled to a patient's cornea with viscoelastic fluid. Under direct microscopic and gonioscopic visualization, the tissue grabber may be inserted through the incision into the anterior chamber and may be advanced across the anterior chamber towards the nasal angle, until the trabecular meshwork is reached. FIG. 14A shows, by way of example, tissue grabber 607 as it reaches the trabecular meshwork 663 through the anterior chamber 665.

B) Advancing the Tissue Grabber into Schlemm's Canal

Figure 21A:
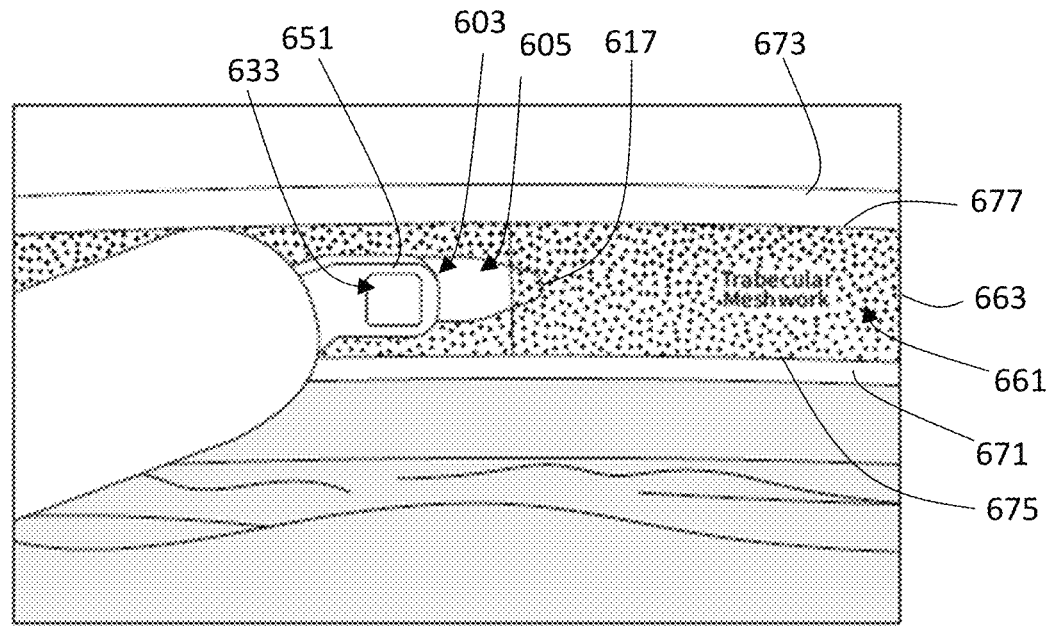
FIGS. 21A-21C show alternative views of various steps of a tearing goniotomy procedure performed with a tissue manipulation and/or tissue tearing device.

Turning to FIGS. 14B-14C, once the tissue grabber 607 reaches the trabecular meshwork 663, the tissue grabber may be inserted into Schlemm's canal 661 by advancing a tip 617 of the guide foot 605 through an insertion point in the trabecular network 663 and into the canal 661. In some variations, the guide foot 605 may be configured to puncture the trabecular meshwork 663 and enter Schlemm's canal 661. For example, in some variations, the tip 617 of the guide foot 605 may be sharpened and/or the guide foot 605 may be tapered in a manner that assists with puncturing the trabecular meshwork 663 (goniopuncture) but does not otherwise cut the meshwork or surrounding tissue. An alternative view of a goniopuncture and entrance of guide foot 605 through an insertion point in the trabecular network 663 and into Schlemm's canal 661 is shown in FIG. 21A.

The tissue grabbing region 603 may be configured so that the act of inserting the guide foot 605 into Schlemm's canal 661 results in a nearby portion of the trabecular meshwork 663 being fed into or otherwise received in the tissue grabbing region. In some variations, where the tissue grabber 607 comprises a window 633 (e.g., on the upper foot such as the variation shown in FIG. 21B), the window 633 may help provide a visual indication of trabecular meshwork entry into the tissue grabbing region to a user. In this way, visual control and device manipulation of the tissue grabber 607 may be enhanced. In some variations, after insertion of the guide foot 605 into the canal 661, an upper grabbing surface 627 of the tissue grabbing region may be positioned above and pressing on the trabecular meshwork 663, and a lower grabbing surface 625 of the tissue grabbing region 603 may be positioned below the trabecular meshwork 663. In some variations, after the guide foot 605 is inserted into, and is thus positioned within, the canal 661, the upper and lower grabbing surfaces 627, 625 may sandwich the trabecular meshwork 663. For example, the upper grabbing surface 625 may be adjacent to and/or in contact the top (dorsal) surface of the trabecular meshwork 663 and the lower grabbing surface 627 may be adjacent to and/or in contact with the bottom (ventral) surface of the trabecular meshwork 663. In some variations, the upper grabbing surface 627 may be movable or adjustable relative to the lower grabbing surface 625 (for example as shown in FIGS. 20A-20C).

C) Advancing the Guide Foot within and Relative to Schlemm's Canal

Figure 14D:
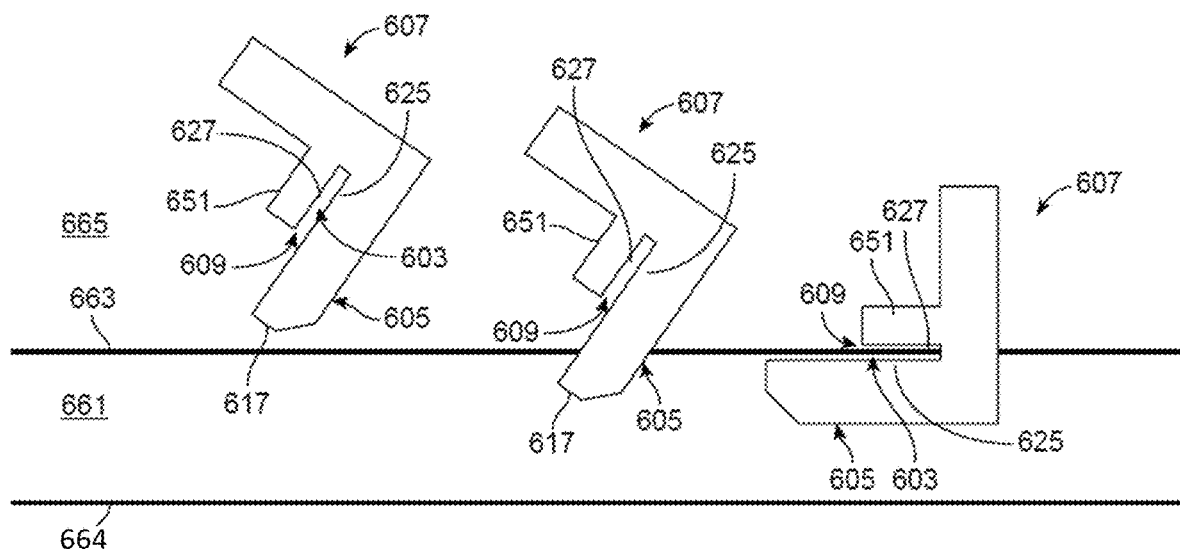
Figure 14D:
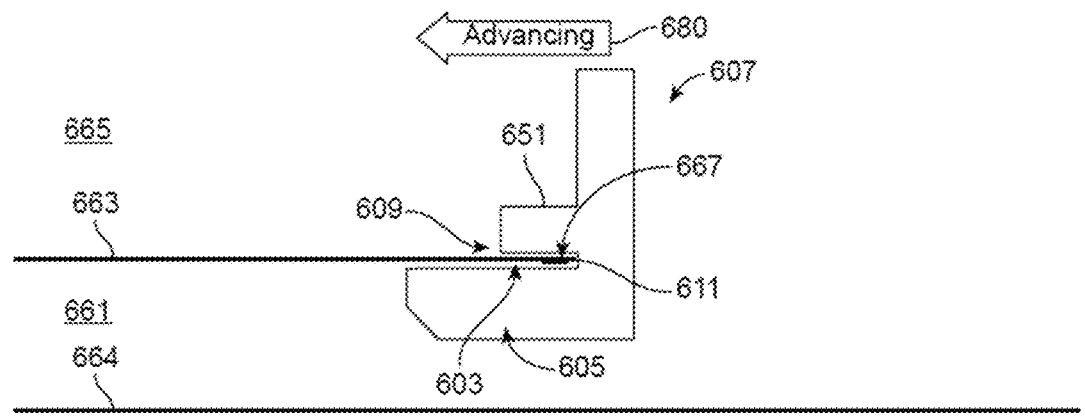
Figure 14E:
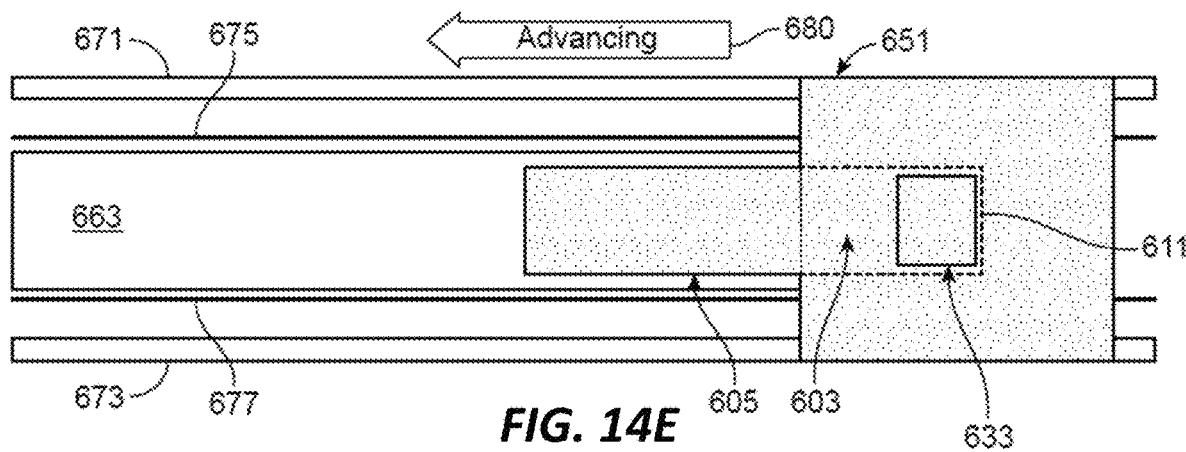

Turing now to FIGS. 14D-14E, the guide foot 605 may be advanced, as schematically shown by block arrow 680, within and relative to Schlemm's canal 663. When this occurs, a portion of the trabecular meshwork (e.g., a central portion) may enter the tissue grabbing region 603 through the front opening 609 of the tissue grabbing region 603. As the tissue grabber 607 is continued to be advanced, this portion of the trabecular meshwork 663 may approach and contact the closed back 611 of the tissue grabbing region 603, and form an accumulation 667 of the trabecular meshwork 663. Moreover, as shown in the top view of FIG. 14E, in some variations, the upper foot 651 and/or the upper grabbing surface 627 (shown here as provided by the upper foot 651) may be sufficiently wide to cover Schwalbe's line 671 and the scleral spur 673. In some instances, this may be advantageous as it may assist in preventing the trabecular meshwork tissue from escaping from the tissue grabbing region 603. The portion of the trabecular meshwork 663 received within the tissue grabbing region 603 may get compressed as it approaches the closed back 611. In some variations, the closed back may have a rounded, atraumatic shape, and all nearby corners and edges may be machined or polished to be rounded and smooth. As a result, the trabecular meshwork 663 fed into or received in the tissue grabbing region may not encounter any sharp edges or cutting mechanisms, and therefore may remain uncut.

Figure 21B:
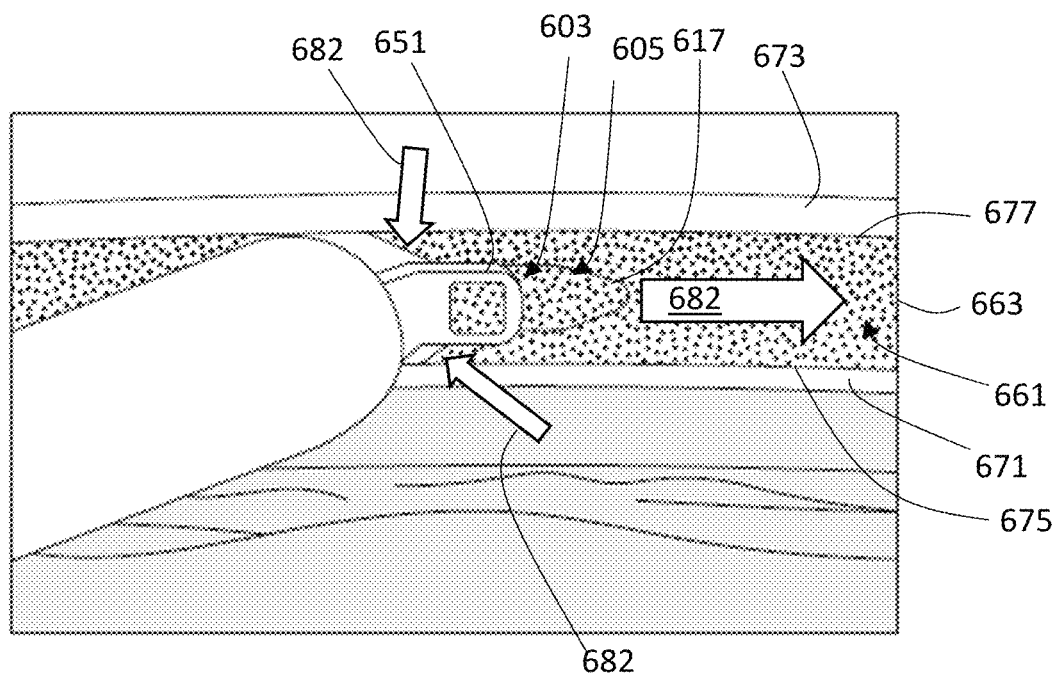
Figure 21C:
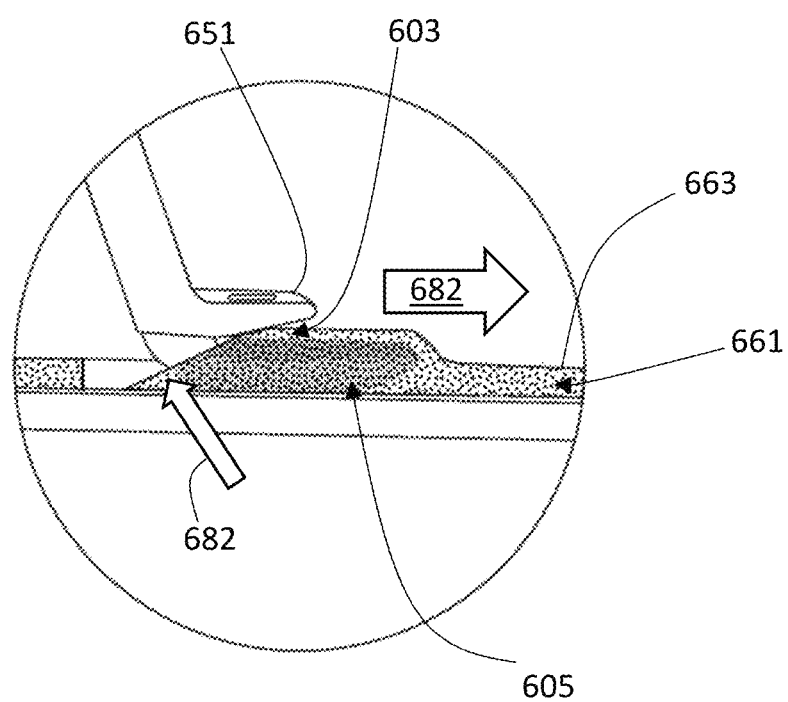

As shown in FIG. 21A (top view) and FIG. 21B (side view), the tissue grabbing region 603 may be configured to receive, grab, and/or trap a central portion of the trabecular meshwork 663, while at least a lateral portion of the trabecular meshwork 663 (e.g., the lateral roots) may remain outside of the tissue grabbing region 603. As the guide foot 605 continues to be advanced, as schematically shown by block arrow 680, within and relative to Schlemm's canal 661, the trapped central portion of the trabecular meshwork 661 within the tissue grabbing region 603 may also be advanced relative to the surrounding ocular tissue, including Schwalbe's line and the scleral spur. As a result, the lateral portion of the trabecular meshwork 663 (e.g., lateral roots, portion of meshwork outside of and directly adjacent to the portion within the tissue grabbing region) located outside of the tissue grabbing region 603 and connecting the trapped trabecular meshwork to the surrounding ocular tissue may be stretched, then torn and/or avulsed. For example, in some variations, the anterior side 675 of the trabecular meshwork 663 may be torn and/or avulsed from Schwalbe's line 671 and the posterior side 677 of the trabecular meshwork 662 may be torn and/or avulsed from the scleral spur 673. As a result of the tearing/avulsion, the trapped central portion of the trabecular meshwork 663 becomes detached from the surrounding tissue. The stretching of a portion of the anterior side 675 of the trabecular meshwork 663 away from the scleral spur 673, as well as the stretching of a portion of the posterior side 677 of the trabecular meshwork 663 are schematically indicated with block arrows 682.

Due to the stretching of the lateral portions of the trabecular meshwork (e.g., in some variations, the lateral roots of the trabecular meshwork) during the advancement of the tissue grabber 607, it will be appreciated that the tearing of the lateral tissue (e.g., lateral roots) may occur at the portion of the lateral tissue located behind or trailing the closed back 611 of the tissue grabber 607, thus resulting in the stripping off on an intact meshwork tissue from the surrounding tissue. Some conventional goniotomies result merely in making an incision or incisions through the trabecular meshwork, or removing a relatively narrow strip of meshwork tissue. It will be appreciated that removal of a strip of trabecular meshwork tissue with the tearing goniotomy described herein provides may result in removal of a wider strip of meshwork tissue, thus providing improved reduction in intraocular pressure compared to conventional, incision-based goniotomies. It is also noted that pieces of attached trabecular meshwork may be left behind as residual leaflets in conventional, incision-based goniotomies. Such residual leaflets may anneal over time and reduce efficacy of the goniotomy over time. By contrast, the tearing goniotomy described herein may result in fewer and/or smaller residual leaflets, thus resulting in longer-lasting treatment of intraocular pressure.

Figure 17A:
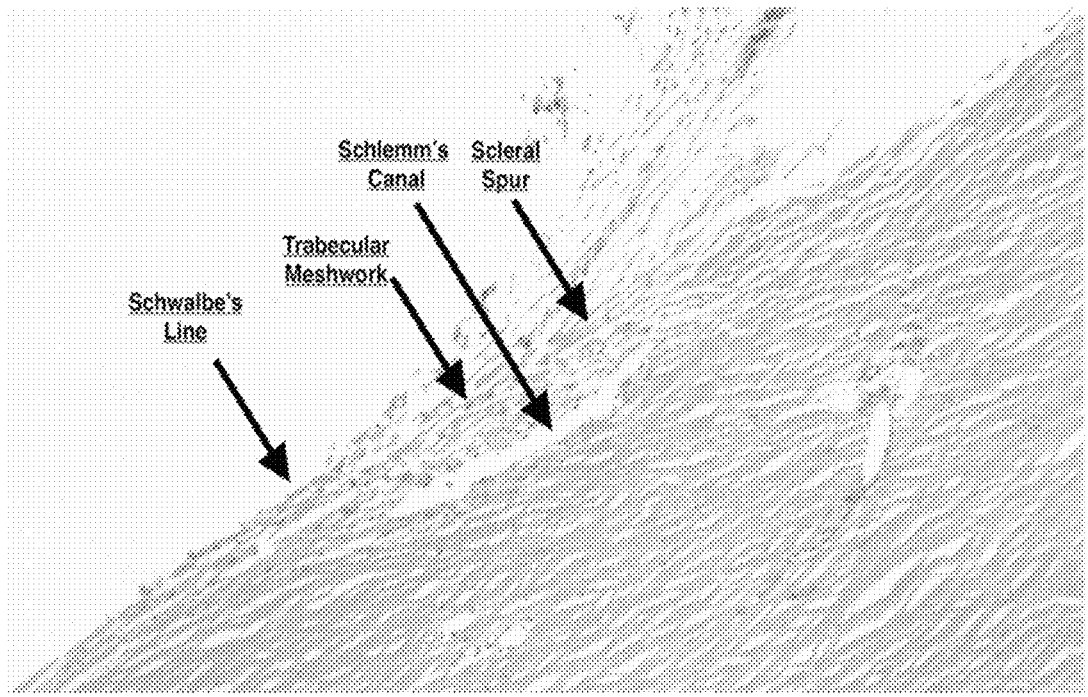
FIGS. 17A and 17B show an image of tissue section from a cadaverous eye before and after treatment with a tearing goniotomy performed with a tissue manipulation and/or tearing device.
Figure 17B:
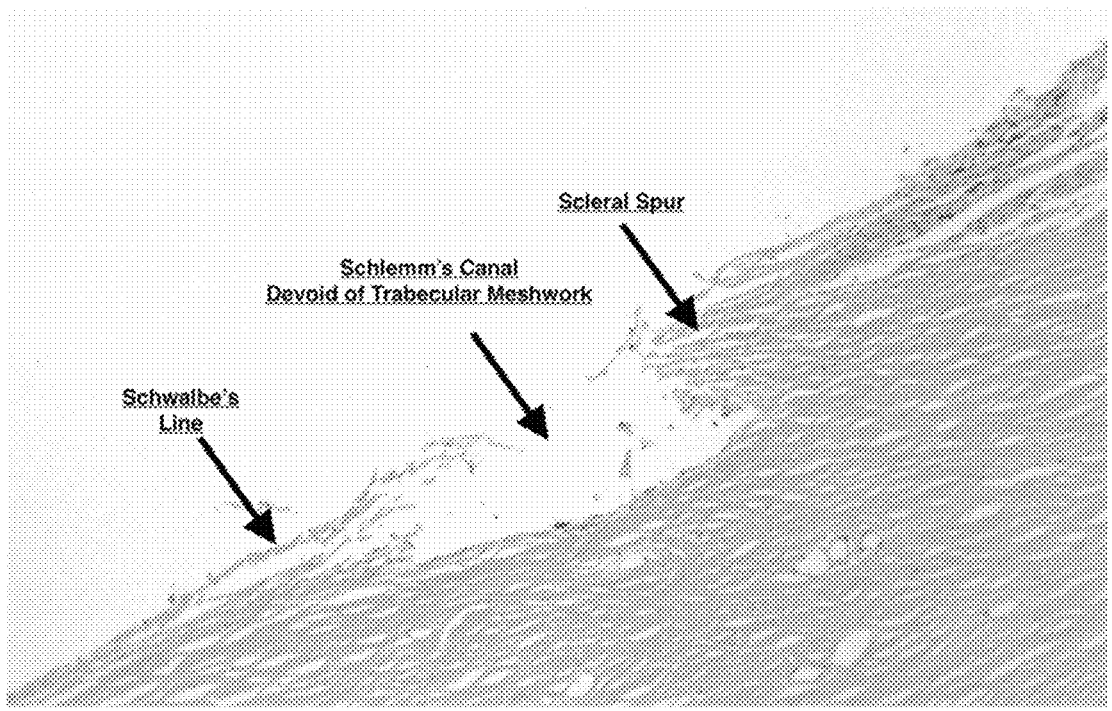

FIGS. 17A and 17B show an image of tissue section from a cadaverous human eye before and after treatment with a tearing goniotomy procedure as described herein. FIG. 17A is control image showing an untreated portion of Schlemm's canal, with an intact trabecular meshwork covering the dorsal side of Schlemm's canal. By contrast, after a tearing goniotomy is performed, as shown in FIG. 17B, the trabecular meshwork is stripped off, and the lumen of Schlemm's canal is fully exposed to the anterior chamber.

In some variations, the tissue grabbing region 603 may comprise one or a combination of two or more tissue grabbing mechanisms configured to promote the inserted tissue getting stuck within the tissue grabbing region. Tissue grabbing mechanisms include, for example: a variable height of the tissue grabbing region, tissue collection openings, and tissue grabbing protrusions as described herein above. By way of example, all or a portion of the upper grabbing surface 627, the lower grabbing surface 625, and/or the closed back 611 may be a roughened or non-polished surface. In some variations, all or a portion of the upper grabbing surface 627, the lower grabbing surface 625, and the/or the closed back 611 may comprise microscopic grabbing protrusions. In some variations, the height of the tissue grabbing region may be variable such that the height decreases from the front opening to the closed back of the tissue grabbing region. Use of a tissue grabber with a variable height may assist in the trabecular meshwork becoming compressed, and thereby trapped, within tissue grabbing region 603.

Generally, when the methods described herein are performed by a user, the user views the tissue grabber in the proximal-to-distal direction as shown by way of example in the top view provided in FIGS. 21A-21B. As depicted in the variation shown there, the upper foot 651 may be shorter than the guide foot 605. As a result, at least the tip 617 of the guide foot may extend beyond the tip of the upper foot 651. In variations of the device with a single foot, by way of example with a guide foot but without an upper foot, the tip of guide foot may be sufficiently long to extend beyond the upper grabbing surface. In this manner, at least the tip 617 of the guide foot may be seen by the user while performing the methods described herein, such as a tearing goniotomy. In some instances, the ability of a user to visualize the tip 617 of the guide foot without the tip being obscured by other components of the device while performing tissue manipulation and/or tearing, may improve visual control of the device for keeping the guide foot within the canal during advancement.

It was found that, advantageously and surprisingly, the tearing of tissue using the tissue manipulation and tearing devices described herein was controlled and limited to the lateral portion of the trabecular meshwork. In other words, tearing the trabecular meshwork with devices comprising the tissue grabbers described herein did not result in unwanted tearing or shredding of the central portion of the trabecular meshwork trapped within the tissue grabbing region or of the surrounding tissue, such as Schwalbe's line and the scleral spur, as well as other nearby tissues such as the cornea, sclera, or iris. Instead, the tearing goniotomy method resulted in a surprisingly effective and thorough removal of trabecular meshwork with minimal trauma to adjacent tissues.

As advancement relative to Schlemm's canal and tearing of the lateral portion of the trabecular meshwork continues, the central portion of the trabecular meshwork may continue to be collected and trapped within the tissue grabbing region 603. After torn from the lateral portion of the trabecular meshwork, this central portion of the trabecular meshwork is detached from the surrounding tissue but may remain attached to a portion of the trabecular meshwork in front of, or along the direction of advancement of, the tissue grabber 607. Collection and trapping of the central portion of the trabecular meshwork may continue until advancement of the tissue grabber 607 within and relative to Schlemm's canal is stopped.

The tissue grabber may be advanced along a variety of arc lengths of the circumference of Schlemm's canal to tear the trabecular meshwork. In certain variations, tissue grabber may be advanced along between about 20 degrees and about 140 degrees, between about 30 degrees and about 120 degrees, between about 40 degrees and about 100 degrees, about 20 degrees, about 30 degrees, about 40 degrees, about 50 degrees, about 60 degrees, about 70 degrees, about 900 degrees, about 90 degrees, about 100 degrees, about 120 degrees, and about 140 degrees around the circumference of Schlemm's canal to tear the trabecular meshwork.

D) Withdrawing the Tissue Grabber from Schlemm's Canal

As noted above, while the central portion of the trabecular meshwork may have been torn, detached or otherwise disassociated with the lateral portion of the trabecular meshwork during advancement of the tissue grabber relative to Schlemm's canal, the central portion of the trabecular meshwork may remain attached to untreated trabecular meshwork at its leading edge. This remaining connection of the detached trabecular meshwork stuck and collected within the tissue grabbing region 602 to the still-intact trabecular meshwork may be severed when the tissue grabber 607 is withdrawn from Schlemm's canal and the trabecular meshwork. Due to being stuck within the tissue grabbing region 203, the detached portion of the trabecular meshwork may be efficiently removed from the eye upon removal of the tissue grabber, without requiring any cutting or additional collection steps. Removal of the detached portion of the trabecular meshwork from the eye may be performed by the same device (e.g., device comprising the tissue grabber) that detached the tissue, which advantageously obviates the need for separately advancing a second device, such as micro forceps, to remove the detached portion of the tissue. Therefore, the tearing goniotomy method reduces the number of steps to perform goniotomy, and it minimizes the introduction and manipulation of instruments in the eye. As a consequence, intraoperative complications and iatrogenic injuries are reduced. While it may be advantageous to remove the detached portion of tissue using the devices described herein, it should be appreciated that the methods described herein may additional comprise advancing a separate tissue collection device, such as, for example, a forceps, to sever the leading edge of the tissue and/or remove the detached portion of tissue.

Upon withdrawal of the tissue grabber from Schlemm's canal and the trabecular meshwork, some of the torn and detached trabecular meshwork may escape from the tissue grabbing region 603. Alternatively or in addition, some of the remaining trabecular meshwork that was severed upon withdrawal of the tissue grabber from Schlemm's canal and the trabecular meshwork may not have been fed into the tissue grabbing region 603. However, such escaped or severed tissue remains attached to the trapped tissue stuck and collected within the tissue grabbing region 603 and may form a trailing ribbon of tissue indirectly attached to and trailing the tissue grabber 607. Therefore, such tissue that was detached but becomes located outside of the tissue grabbing region may nevertheless be removed from the eye along with the tissue grabber and the trapped tissue.

In some variations, methods of tearing tissue may further comprise techniques to assist in removing the detached but non-trapped portion of tissue. For example, in some variations, methods of tearing tissue may further comprise rotating the device along the longitudinal axis of the shaft, in order to wrap any detached but non-trapped tissue around a portion of the tissue grabber (e.g., a proximal portion) and/or the shaft. In certain variations, upon withdrawal of the tissue grabber from Schlemm's canal or the trabecular meshwork, the device may be rotated along the longitudinal axis of the shaft to a degree sufficient to wrap the detached but non-trapped tissue around a portion of the tissue grabber (e.g., a proximal portion) and/or the shaft, by way of example for more than 180 degrees, more than 360 degrees, more than 720 degrees, more than 1080 degrees, between about 180 degrees and about 1080 degrees. The rotation along the longitudinal axis of the shaft may be perform while the tissue grabber is within the anterior chamber, soon or immediately after the tissue grabber withdrawn from Schlemm's canal or the trabecular meshwork while still inside the anterior chamber of the eye, and before the tissue grabber is removed from the eye. The one or more feet comprised in the tissue grabber may be sufficient short so that the rotation along the longitudinal axis of the shaft can be performed while the tissue grabber is within the anterior chamber without inadvertently contacting nearby ocular tissue.

After the tissue grabber 607 is withdrawn from Schlemm's canal, the device 600 can be fully removed from the eye, taking the torn and detached trabecular meshwork along with it. In certain variations, after the tissue grabber 607 is withdrawn from Schlemm's canal to remove the detached tissue, the user may perform a second tearing goniotomy in a different portion of the trabecular meshwork in the same eye. In certain variations, the user may advance the tissue grabber to a different portion of the trabecular meshwork, re-insert the guide foot through the trabecular meshwork and into Schlemm's canal, and repeat the tearing goniotomy. In certain variations, the user may rotate the device inside the eye about 180 degrees so that the tissue grabber is pointed in the second direction opposite the direction of the first advancement within and relative to Schlemm's canal, return the tissue grabber to the original point of insertion into the trabecular meshwork for the previous tearing goniotomy, and perform a second tearing goniotomy in the same eye in the second direction within and relative to Schlemm's canal. In certain variations, the user may remove the previously trapped tissue collected in the first tearing goniotomy, by way of example with a separate pair of forceps before continuing with the second tearing goniotomy. In other variations, the user may go directly from the first to the second tearing goniotomy without removing the previously collected tissue from the tissue grabber.

After completion of tissue tearing t and removal of the device (along with the torn and detached trabecular meshwork) from the eye, viscoelastic fluid and blood may be rinsed from the eye using irrigation. The surgeon may further preform any of the following further steps: gently pressurize the eye with balanced salt solution (BSS); hydrate the wound with BSS to prevent a wound leak; use viscoelastic fluid to tamponade any blood reflux; apply a miotic to constrict the pupil; place a suture to prevent a wound leak; elevate the patient's head to reduce reflux of blood into eye.

Other Aspects of the Tearing Trabeculectomy Method

The tissue tearing methods described here may be performed in order to reduce, and may result in reduction in, intraocular pressure (IOP) or a reduced need for IOP-lowering medications in a subject suffering therefrom. In some variations, the methods may be performed on a subject suffering from glaucoma. The tissue tearing methods described herein may be performed in conjunction with, preceded by, for followed by administration of a therapeutic amount of IOP-lowering medication, to the subject. The IOP-lowering medication may be: a prostaglandin analog such as latanoprost, bimatoprost, travoprost, tafluprost, or latanoprostene bunod; a beta blocker such as timolol; an alpha agonist such as brimonidine; or a carbonic anhydrase inhibitor (CAI) such as dorzolamide, brinzolamide, acetazolamide, or methazolamide; a Rho kinase inhibitor such as netarsudil, or combinations thereof.

The above-described tearing goniotomy may be performed as a standalone surgical procedure, or may be performed in combination with other ocular surgical procedures, such as, for example, cataract surgery, canaloplasty, or viscodilation of Schlemm's canal.

The above-described tearing goniotomy may be performed on a subject suffering from glaucoma in combination with any other glaucoma-treating procedure, including but not limited to: placement of trabecular microbypass stents or scaffolds; placement of suprachoroidal shunts, placement of sustained release glaucoma pharmaceutical implants, endoscopic cyclophotocoagulation, and others.

The invention claimed is:

1. A method of tearing trabecular meshwork of an eye of a subject, the method comprising:
  advancing a tissue grabber at a distal end of a shaft to Schlemm's canal of the eye, wherein the tissue grabber comprises a lower foot, an upper foot, and a groove formed between the lower foot and the upper foot;
  advancing a tip of the lower foot through the trabecular meshwork and into Schlemm's canal; and
  advancing the lower foot within and relative to Schlemm's canal such that a portion of the trabecular meshwork is trapped in the groove, wherein the portion of the trabecular meshwork trapped in the groove is initially connected to the surrounding tissue by lateral roots of the trabecular meshwork, and as the lower foot is advanced, the lateral roots are torn behind a closed back of the groove.

2. The method of claim 1, wherein the lower foot is positioned below the trabecular meshwork and the upper foot is positioned above the trabecular meshwork.

3. The method of claim 1, wherein the groove is defined by an upper surface at least partially coextensive with a plantar surface of the upper foot and a lower surface at least partially coextensive with a dorsal surface of the lower foot.

4. The method of claim 3, wherein the upper surface and the lower surface connect at the closed back of the groove.

5. The method of claim 3, wherein at least a portion of the upper surface or the lower surface is roughened.

6. The method of claim 1, wherein the closed back has a rounded shape.

7. The method of claim 6, wherein a radius of curvature of the closed back of the groove is at least 10 microns, at least 15 microns, at least 20 microns, about 10 microns, about 15 microns, or about 20 microns.

8. The method of claim 1, wherein the upper foot comprises a window that traverses a portion of the upper foot.

9. The method of claim 1, wherein the groove has a variable height.

10. The method of claim 1, wherein a length of the lower foot is greater than a length of the upper foot.

11. The method of claim 1, wherein a maximum width of the upper foot is greater than a maximum width of the lower foot.

12. The method of claim 11, wherein the upper foot presses on and covers the trabecular meshwork as the lower foot is advanced.

13. The method of claim 1, wherein the tissue grabber is bladeless.

14. The method of claim 1, wherein the lower foot comprises a central longitudinal axis that is transverse to a longitudinal axis of the shaft.

15. The method of claim 1, wherein the lower foot is advanced within and relative to Schlemm's canal for between about 30 degrees and about 120 degrees around a circumference of the canal in a first direction.

16. The method of claim 15 further comprising removing the lower foot from the canal, rotating the device along a longitudinal axis of the shaft about 180 degrees so that the lower foot is pointed in an opposite direction, re-entering the canal, and advancing the lower foot within and relative to Schlemm's canal in a second, opposite direction.

17. The method of claim 16, wherein the lower foot is advanced within and relative to Schlemm's canal for between about 30 degrees and about 120 degrees around the circumference of the canal in the second direction.

18. The method of claim 1, wherein the subject is suffering from high intraocular pressure.

19. The method of claim 18, wherein the high intraocular pressure is caused by glaucoma.

20. The method of claim 1, wherein the method is performed as a standalone procedure.

21. The method of claim 1, wherein the method is performed in conjunction with cataract removal, canaloplasty, or another glaucoma treatment procedure.

22. The method of claim 21, wherein the glaucoma treatment procedure is selected from the group consisting of: deployment of a trabecular microbypass stent or scaffold, deployment of a suprachoroidal shunt, placement of a sustained release glaucoma pharmaceutical implant, and endoscopic cyclophotocoagulation.

23. A method of tearing trabecular meshwork of an eye of a subject, the method comprising:
  advancing a tissue grabber at a distal end of a shaft to Schlemm's canal of the eye, wherein the tissue grabber comprises a lower foot, an upper foot, and a groove formed between the lower foot and the upper foot;
  advancing a tip of the lower foot through the trabecular meshwork and into Schlemm's canal; and
  advancing the lower foot within and relative to Schlemm's canal such that a portion of the trabecular meshwork is trapped in the groove, wherein the upper foot comprises a window that traverses a portion of the upper foot.

24. The method of claim 23, wherein the lower foot is positioned below the trabecular meshwork and the upper foot is positioned above the trabecular meshwork.

25. The method of claim 23, wherein as the lower foot is advanced within and relative to Schlemm's canal, at least the portion of the trabecular meshwork is detached from surrounding tissue of the eye.

26. The method of claim 23, wherein the groove is defined by an upper surface at least partially coextensive with a plantar surface of the upper foot and a lower surface at least partially coextensive with a dorsal surface of the lower foot.

27. The method of claim 26, wherein the upper surface and the lower surface connect at a closed back of the groove.

28. The method of claim 26, wherein at least a portion of the upper surface or the lower surface is roughened.

29. The method of claim 27, wherein the closed back has a rounded shape.

30. The method of claim 29, wherein a radius of curvature of the closed back of the groove is at least 10 microns, at least 15 microns, at least 20 microns, about 10 microns, about 15 microns, or about 20 microns.

31. The method of claim 23, wherein the groove has a variable height.

32. The method of claim 23, wherein a length of the lower foot is greater than a length of the upper foot.

33. The method of claim 32, wherein a maximum width of the upper foot is greater than a maximum width of the lower foot.

34. The method of claim 33, wherein the upper foot presses on and covers the trabecular meshwork as the lower foot is advanced.

35. The method of claim 23, wherein the tissue grabber is bladeless.

36. The method of claim 23, wherein the lower foot comprises a central longitudinal axis that is transverse to a longitudinal axis of the shaft.

37. The method of claim 23, wherein the lower foot is advanced within and relative to Schlemm's canal for between about 30 degrees and about 120 degrees around a circumference of the canal in a first direction.

38. The method of claim 37 further comprising removing the lower foot from the canal, rotating the device along a longitudinal axis of the shaft about 180 degrees so that the lower foot is pointed in an opposite direction, re-entering the canal, and advancing the lower foot within and relative to Schlemm's canal in a second, opposite direction.

39. The method of claim 38, wherein the lower foot is advanced within and relative to Schlemm's canal for between about 30 degrees and about 120 degrees around the circumference of the canal in the second direction.

40. The method of claim 23, wherein the subject is suffering from high intraocular pressure.

41. The method of claim 40, wherein the high intraocular pressure is caused by glaucoma.

42. The method of claim 23, wherein the method is performed as a standalone procedure.

43. The method of claim 23, wherein the method is performed in conjunction with cataract removal, canaloplasty, or another glaucoma treatment procedure.

44. The method of claim 43, wherein the glaucoma treatment procedure is selected from the group consisting of: deployment of a trabecular microbypass stent or scaffold, deployment of a suprachoroidal shunt, placement of a sustained release glaucoma pharmaceutical implant, and endoscopic cyclophotocoagulation.

* * * * *